(12) United States Patent
Song et al.

(10) Patent No.: US 8,349,873 B2
(45) Date of Patent: *Jan. 8, 2013

(54) FACTOR XA INHIBITORS

(75) Inventors: Yonghong Song, Foster City, CA (US); Zhaozhong J. Jia, San Mateo, CA (US); Anjali Pandey, Fremont, CA (US); Robert M. Scarborough, Half Moon Bay, CA (US); Carroll Scarborough, legal representative, Half Moon Bay, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/270,170

(22) Filed: Oct. 10, 2011

(65) Prior Publication Data

US 2012/0088795 A1    Apr. 12, 2012

Related U.S. Application Data

(63) Continuation of application No. 12/777,956, filed on May 11, 2010, now Pat. No. 8,063,077, which is a continuation of application No. 11/744,735, filed on May 4, 2007, now Pat. No. 7,763,608.

(60) Provisional application No. 60/883,667, filed on Jan. 5, 2007, provisional application No. 60/797,954, filed on May 5, 2006.

(51) Int. Cl.
*A61K 31/4412*    (2006.01)
(52) U.S. Cl. ..................................... 514/341
(58) Field of Classification Search ............. 514/341
See application file for complete search history.

(56) References Cited

U.S. PATENT DOCUMENTS

| | | | |
|---|---|---|---|
| 6,376,515 B2 | 4/2002 | Zhu et al. | |
| 6,423,713 B1 | 7/2002 | Anantanarayan et al. | |
| 6,835,739 B2 | 12/2004 | Zhu et al. | |
| 6,844,367 B1 | 1/2005 | Zhu et al. | |
| 6,906,063 B2 | 6/2005 | Scarborough et al. | |
| 7,022,695 B2 | 4/2006 | Zhu et al. | |
| 7,157,456 B2 | 1/2007 | Straub et al. | |
| 7,285,565 B2 | 10/2007 | Zhu et al. | |
| 7,312,235 B2 | 12/2007 | Zhu et al. | |
| 7,314,874 B2 | 1/2008 | Zhu et al. | |
| 7,342,013 B2 | 3/2008 | Zhu et al. | |
| 7,521,470 B2 | 4/2009 | Zhu et al. | |
| 7,598,276 B2 | 10/2009 | Grant et al. | |
| 7,696,352 B2 | 4/2010 | Zhu et al. | |
| 7,727,981 B2 | 6/2010 | Zhu et al. | |
| 7,727,982 B2 | 6/2010 | Zhu et al. | |
| 7,763,608 B2 | 7/2010 | Song et al. | |
| 7,767,697 B2 | 8/2010 | Song et al. | |
| 8,063,077 B2 | 11/2011 | Song et al. | |
| 2003/0162690 A1 | 8/2003 | Zhu et al. | |
| 2005/0171358 A1 | 8/2005 | Shimozono et al. | |
| 2006/0100193 A1 | 5/2006 | Zhu et al. | |
| 2007/0066615 A1 | 3/2007 | Gerdes et al. | |
| 2007/0112039 A1 | 5/2007 | Grant et al. | |
| 2007/0185092 A1 | 8/2007 | Zhu et al. | |
| 2007/0259924 A1 | 11/2007 | Song et al. | |
| 2008/0051578 A1 | 2/2008 | Dahmann et al. | |
| 2008/0153876 A1 | 6/2008 | Sinha et al. | |
| 2008/0241233 A1 | 10/2008 | Sims et al. | |
| 2008/0254036 A1 | 10/2008 | Sinha et al. | |
| 2008/0279845 A1 | 11/2008 | Conley et al. | |
| 2008/0293704 A1 | 11/2008 | Jia et al. | |
| 2009/0098119 A1 | 4/2009 | Lu et al. | |
| 2009/0186810 A1 | 7/2009 | Zwaal et al. | |
| 2009/0298806 A1 | 12/2009 | Zhu et al. | |
| 2010/0063113 A1 | 3/2010 | Grant et al. | |
| 2010/0125052 A1 | 5/2010 | Lu et al. | |
| 2010/0197929 A1 | 8/2010 | Scarborough et al. | |
| 2010/0234352 A1 | 9/2010 | Zhu et al. | |
| 2010/0255000 A1 | 10/2010 | Sinha et al. | |
| 2010/0298284 A1 | 11/2010 | Zhu et al. | |
| 2011/0015128 A1 | 1/2011 | Sinha et al. | |

FOREIGN PATENT DOCUMENTS

| | | |
|---|---|---|
| CA | 2 453 846 | 1/2003 |
| CA | 2 653 666 | 12/2007 |
| DE | 10322469 | 12/2004 |
| WO | WO 99/07379 | 2/1999 |
| WO | WO 99/28317 | 6/1999 |
| WO | WO 01/19788 | 3/2001 |
| WO | WO 01/21160 | 3/2001 |
| WO | WO 01/47919 | 7/2001 |
| WO | WO 01/64642 | 9/2001 |
| WO | WO 01/64643 | 9/2001 |
| WO | WO 01/91558 | 12/2001 |
| WO | WO 02/00651 | 1/2002 |
| WO | WO 02/079145 | 10/2002 |
| WO | WO 03/008395 | 1/2003 |
| WO | WO 03/059894 | 7/2003 |
| WO | WO 2004/101531 | 11/2004 |
| WO | WO 2004/101557 | 11/2004 |
| WO | WO 2004/106329 | 12/2004 |

(Continued)

OTHER PUBLICATIONS

U.S. Appl. No. 13/213,927, filed Aug. 19, 2011, Zhu et al.
Ostrovsky et al., "Analysis of Activity for Factory Xa Inhibitors Based on Monte Carlo Simulations", *J. Med. Chem.*, 46, 5691-5699 (2003).
Roehrig et al., "Discovery of the Novel Antithrombotic Agent 5-Chloro-N-(((5S)-2-oxo-3[4-(3-oxomorpholin-4-yl)phenyl]-1,3-oxazol idin-5-yl)methyl)thiophene 2-carboxamide (BAY 59/7939): An Oral, Direct Factor Xa Inhibitor", *J. Med. Chem.*, 48, 5900-5908 (2005).
US 7,479,487, 01/2009, Zhu et al. (withdrawn)

*Primary Examiner* — Taofiq A Solola
(74) *Attorney, Agent, or Firm* — Foley & Lardner LLP

(57) ABSTRACT

The present invention is directed to compounds of formula (I) and pharmaceutically acceptable salts, esters, and prodrugs thereof which are inhibitors of Factor Xa. The present invention is also directed to intermediates used in making such compounds, pharmaceutical compositions containing such a compound, methods to prevent or treat a number of conditions characterized by undesired thrombosis and methods of inhibiting the coagulation of a blood sample.

14 Claims, 3 Drawing Sheets

FOREIGN PATENT DOCUMENTS

| | | |
|---|---|---|
| WO | WO 2005/032468 | 4/2005 |
| WO | WO 2005/034867 | 4/2005 |
| WO | WO 2005/035528 | 4/2005 |
| WO | WO 2005/082892 | 9/2005 |
| WO | WO 2006/002099 | 1/2006 |
| WO | WO 2007/007588 | 1/2007 |
| WO | WO 2007/025940 | 3/2007 |
| WO | WO 2007/056219 | 5/2007 |
| WO | WO 2007/112367 | 10/2007 |
| WO | WO 2007/131179 | 11/2007 |
| WO | WO 2007/137791 | 12/2007 |
| WO | WO 2008/057972 | 5/2008 |
| WO | WO 2008/073670 | 6/2008 |
| WO | WO 2008/086188 | 7/2008 |
| WO | WO 2008/086226 | 7/2008 |
| WO | WO 2008/121721 | 10/2008 |
| WO | WO 2008/127682 | 10/2008 |
| WO | WO 2008/137787 | 11/2008 |
| WO | WO 2009/042962 | 4/2009 |
| WO | WO 2010/056765 | 5/2010 |
| WO | WO/2010/117729 | 10/2010 |
| WO | WO/2011/008885 | 1/2011 |

FACTOR XA INHIBITORS

CROSS REFERENCE TO RELATED APPLICATION

This application is a continuation of U.S. patent application Ser. No. 12/777,956, filed May 11, 2010, now U.S. Pat. No. 8,063,077, which is a continuation of U.S. patent application Ser. No. 11/744,735, filed May 4, 2007, now U.S. Pat. No. 7,763,608, which claims the benefit under 35 U.S.C. §119 (e) of U.S. Provisional Application Ser. No. 60/883,667, filed Jan. 5, 2007, and U.S. Provisional Application Ser. No. 60/797,954, filed May 5, 2006, all of which are hereby incorporated by reference in their entirety.

BACKGROUND OF THE INVENTION

1. Field of the Invention

This invention is directed to substituted imidazole compounds which act as inhibitors of Factor Xa. This invention is also directed to pharmaceutical compositions containing the substituted imidazole compounds and methods of using the compounds or compositions to treat a condition characterized by undesired thrombosis. The invention is also directed to methods of making the compounds described herein.

2. State of the Art

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in restoring hemostasis and in thrombotic diseases, certain components of the coagulation cascade are primarily responsible for the amplification and acceleration of the processes involved in platelet aggregation and fibrin deposition which are major events in thrombosis and hemostasis.

Clot formation involves the conversion of fibrinogen to fibrin which polymerizes into a network to restore hemostasis after injury. A similar process results in occluded blood vessels in thrombotic diseases. The conversion of fibrinogen to fibrin is catalyzed by thrombin, the end product of a series of reactions in the blood coagulation cascade. Thrombin is also a key player in activating platelets, thereby contributing to thrombosis under conditions of both arterial and venous blood flow. For these reasons, it has been postulated that efficient regulation of thrombin can lead to efficient regulation of thrombosis. Several classes of currently used anticoagulants directly or indirectly affect thrombin (i.e. unfractionated heparins, low-molecular weight heparins, heparin-like compounds, pentasaccharide and warfarin). Direct or indirect inhibition of thrombin activity has also been the focus of a variety of anticoagulants in clinical development (reviewed by Eriksson and Quinlan, *Drugs* 11: 1411-1429, 2006).

Prothrombin, the precursor for thrombin, is converted to the active enzyme by factor Xa. Localized activation of tissue factor/factor VIIa mediated factor Xa generation is amplified by the factor IXa/factor VIIIa complex and leads to prothrombinase assembly on activated platelets. Factor Xa, as a part of the prothrombinase complex, is the sole enzyme responsible for sustained thrombin formation in the vasculature. Factor Xa is a serine protease, the activated form of its precursor Factor X, and a member of the calcium ion binding, gamma carboxyglutamic acid (GLA)-containing, vitamin K dependent, blood coagulation factors. Unlike thrombin, which acts on a variety of protein substrates including fibrinogen and the PAR receptors (Protease activated receptors, Coughlin, *J Thrombosis Haemostasis* 3: 1800-1814, 2005), factor Xa appears to have a single physiologic substrate, namely prothrombin. Since one molecule of factor Xa may be able to generate greater than 1000 molecules of thrombin (Mann, et al., *J. Thrombosis. Haemostasis* 1: 1504-1514, 2003), direct inhibition of factor Xa as a way of indirectly inhibiting the formation of thrombin may be an efficient anticoagulant strategy. This assertion is based on the key role of prothrombinase in thrombin synthesis and on the fact that inhibition of prothrombinase will have a pronounced effect on the overall platelet aggregation and clotting pathways.

Activated proteases such as factor VIIa, factor IXa or factor Xa have poor proteolytic activity on their own. However, their assembly into cofactor-dependent, membrane-bound complexes significantly enhances their catalytic efficiencies. This effect is most dramatic for factor Xa, where the efficiency is increased by a factor of $10^5$ (Mann, et al., *Blood* 76(1):1-16, 1990). Due to the higher concentration of the zymogens present in blood (1.4 micromolar prothrombin versus 150 nanomolar factor X) and the kinetics of activation, a smaller amount of factor Xa than thrombin needs to be inhibited to achieve an anticoagulant effect. Indirect proof of the hypothesis of superiority of factor Xa as a therapeutic target compared to thrombin can also be found in clinical trials for the prevention of deep vein thrombosis. Fondaparinux, an antithrombin III dependent factor Xa inhibitor, was proven to be superior to enoxaparin (a low molecular weight heparin that inhibits both thrombin and factor Xa) in four trials of orthopedic surgery (Turpie, et al., *Archives Internal Medicine* 162 (16): 1833-1840, 2002). Therefore, it has been suggested that compounds which selectively inhibit factor Xa may be useful as in vitro diagnostic agents, or for therapeutic administration in certain thrombotic disorders, see e.g., WO 94/13693.

Several Factor Xa inhibitors have been reported as polypeptides derived from hematophagous organisms, as well as compounds which are not large polypeptide-type inhibitors. Additional Factor Xa inhibitors include small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal C(=NH)—NH$_2$ group; WO 97/21437 describes benzimidazole compounds substituted by a basic radical which are connected to a naphthyl group via a straight or branched chain alkylene, —C(=O) or —S(=O)$_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

BRIEF SUMMARY OF THE INVENTION

In one aspect, the present invention provides compounds having the following formula:

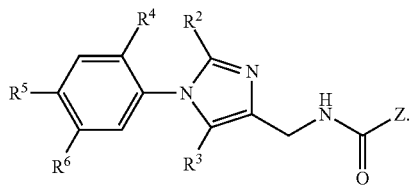
(I)

In formula (I), the symbol Z is selected from the group consisting of:

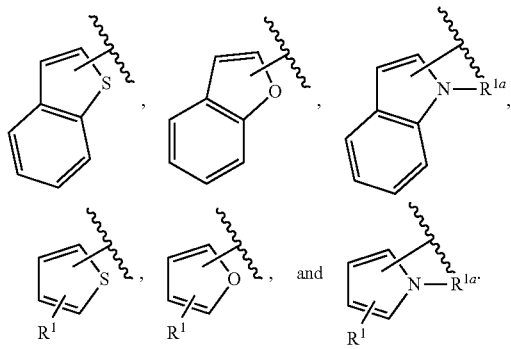

The symbol $R^1$ is selected from the group consisting of halogen, $C_{1-8}$ alkyl, $C_{2-8}$ alkenyl, and $C_{2-8}$ alkynyl. The symbol $R^{1a}$ is hydrogen or $C_{1-4}$ alkyl.

The symbol $R^2$ and $R^3$ are independently selected from the group consisting of hydrogen, halogen, $C_{1-4}$ alkyl, $SR^{4a}$, $S(O)R^{4a}$, $S(O)_2R^{4a}$, $COR^{4a}$, $CO_2R^{4a}$, $CONR^{4a}R^{4b}$, CN, and $S(O)_2NR^{4a}R^{4b}$.

The symbol $R^4$ represents a moiety independently selected from the group consisting of) hydrogen, halogen, $OR^{4a}$, $SR^{4a}$, $S(O)R^{4a}$, $S(O)_2R^{4a}$, $NR^{4a}R^{4b}$, $CO_2R^{4a}$,

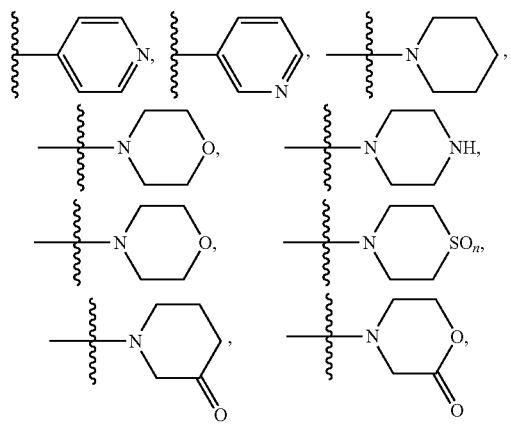

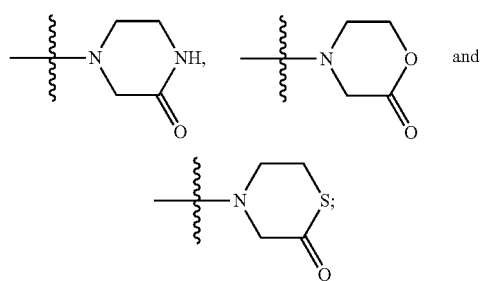

wherein each of these ring systems is optionally substituted with from 1 to 3 substituents independently selected from the group consisting of halogen, amino, oxo, $C_{1-8}$ alkyl, $C_{1-8}$ haloalkyl, hydroxy, $C_{1-8}$ alkoxy, heterocycloalkyl, heteroaryl, and heteroaryl-$C_{1-4}$ alkyl.

The symbols $R^{4a}$ or $R^{4b}$ are independently hydrogen or $C_{1-4}$ alkyl, optionally substituted with from 1 to 2 substituents independently selected from the group consisting of halogen, hydroxyl, alkoxy, heterocyclyl, oxo, amino, and carboxyl. The subscript n is an integer from 0 to 2.

The symbol $R^5$ is selected from the group consisting of:

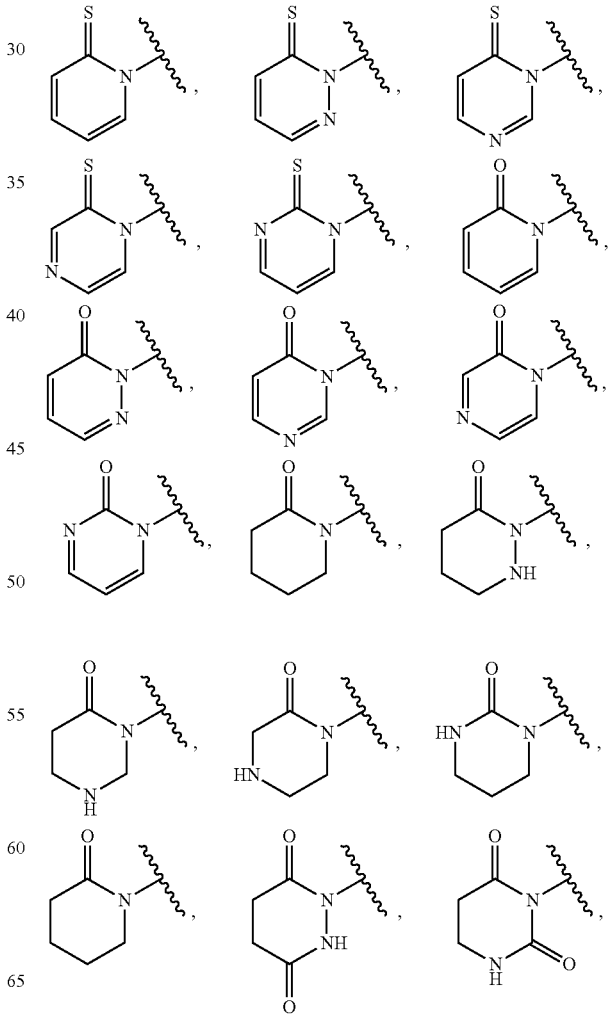

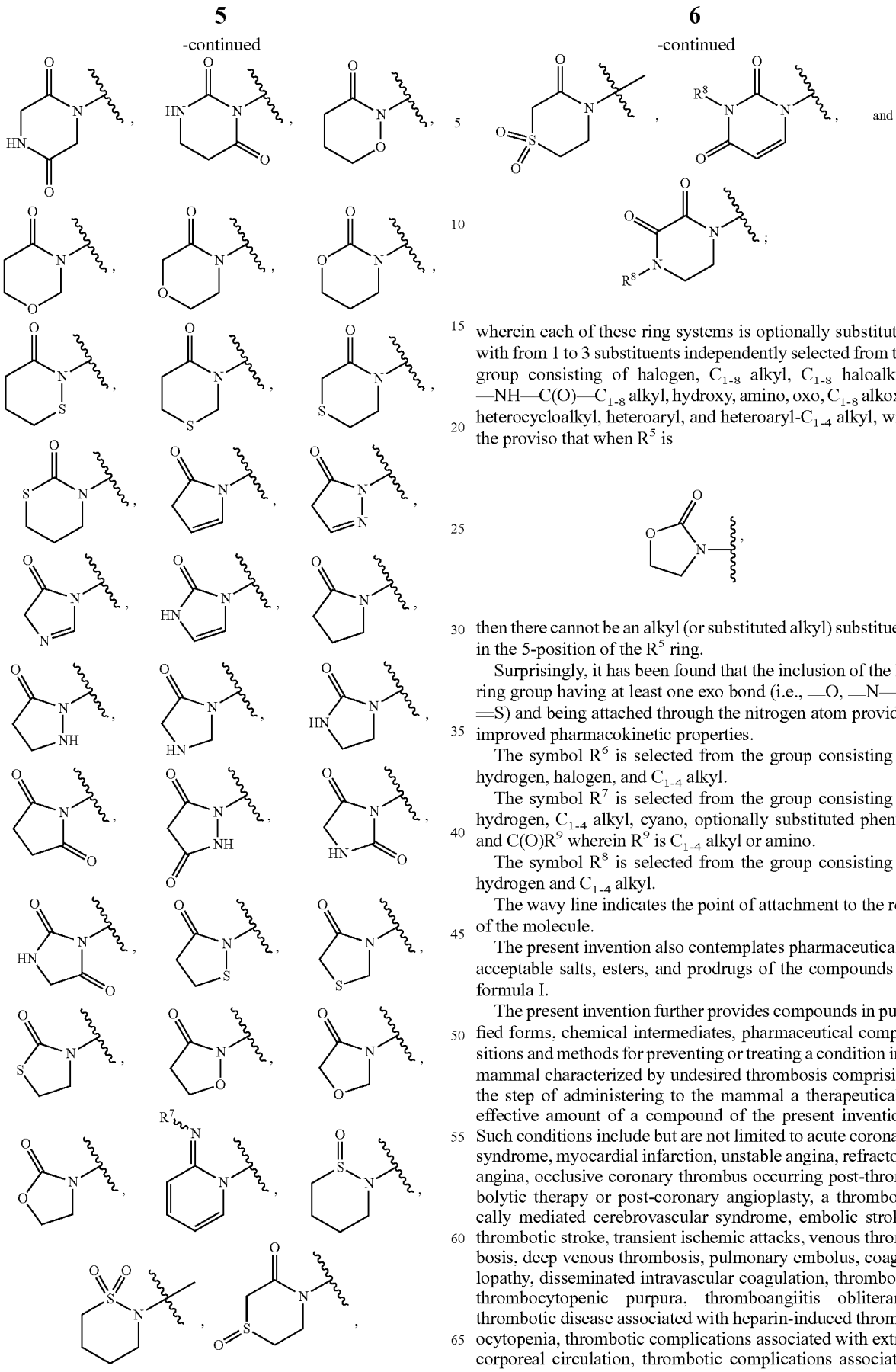

wherein each of these ring systems is optionally substituted with from 1 to 3 substituents independently selected from the group consisting of halogen, $C_{1-8}$ alkyl, $C_{1-8}$ haloalkyl, —NH—C(O)—$C_{1-8}$ alkyl, hydroxy, amino, oxo, $C_{1-8}$ alkoxy, heterocycloalkyl, heteroaryl, and heteroaryl-$C_{1-4}$ alkyl, with the proviso that when $R^5$ is then there cannot be an alkyl (or substituted alkyl) substituent in the 5-position of the $R^5$ ring.

Surprisingly, it has been found that the inclusion of the $R^5$ ring group having at least one exo bond (i.e., =O, =N—R, =S) and being attached through the nitrogen atom provides improved pharmacokinetic properties.

The symbol $R^6$ is selected from the group consisting of hydrogen, halogen, and $C_{1-4}$ alkyl.

The symbol $R^7$ is selected from the group consisting of hydrogen, $C_{1-4}$ alkyl, cyano, optionally substituted phenyl, and C(O)$R^9$ wherein $R^9$ is $C_{1-4}$ alkyl or amino.

The symbol $R^8$ is selected from the group consisting of hydrogen and $C_{1-4}$ alkyl.

The wavy line indicates the point of attachment to the rest of the molecule.

The present invention also contemplates pharmaceutically acceptable salts, esters, and prodrugs of the compounds of formula I.

The present invention further provides compounds in purified forms, chemical intermediates, pharmaceutical compositions and methods for preventing or treating a condition in a mammal characterized by undesired thrombosis comprising the step of administering to the mammal a therapeutically effective amount of a compound of the present invention. Such conditions include but are not limited to acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

The present invention further provides methods for inhibiting the coagulation of a blood sample comprising contacting the sample with a compound of the present invention.

DETAILED DESCRIPTION OF THE INVENTION

1. Abbreviations and Definitions

Figure 1:
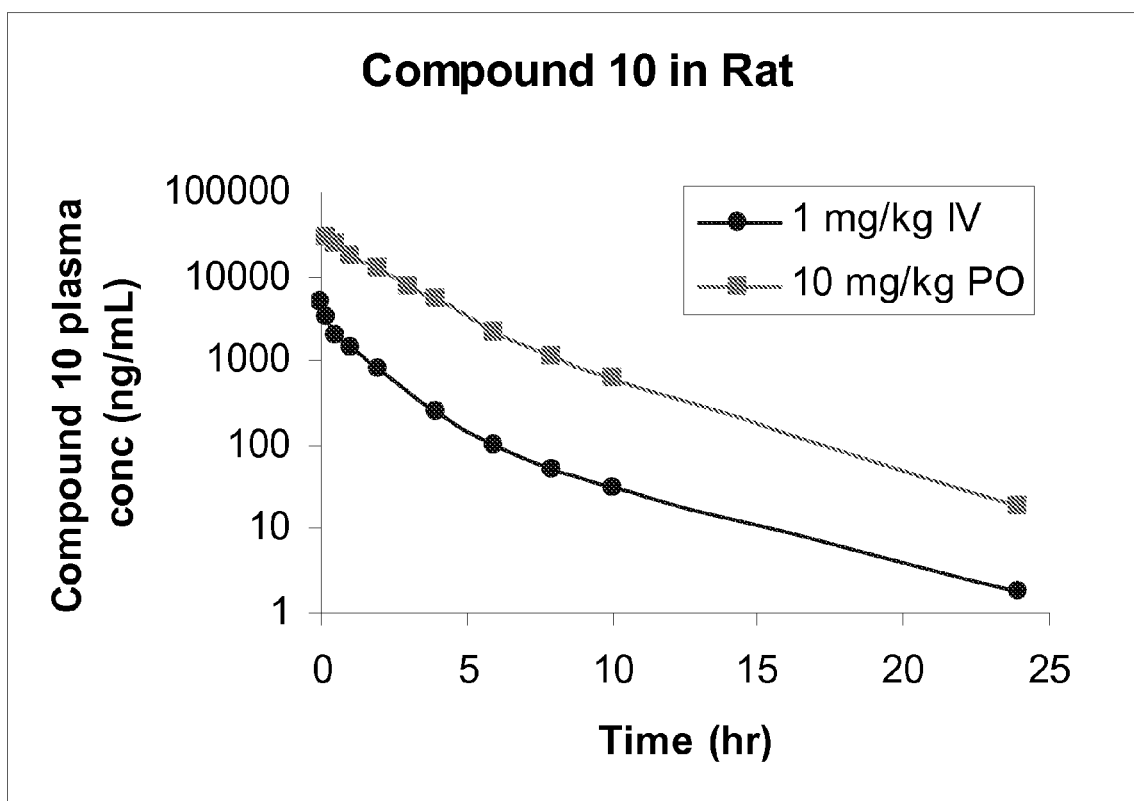
FIG. 1. Shows mean plasma concentration-time profiles of compound 10 in male Sprague-Dawley rats after 1 mg/kg intravenous (●) and 10 mg/kg oral (■) administration (n=3/group). Plasma samples were measured using LC/MS/MS.
Figure 2:
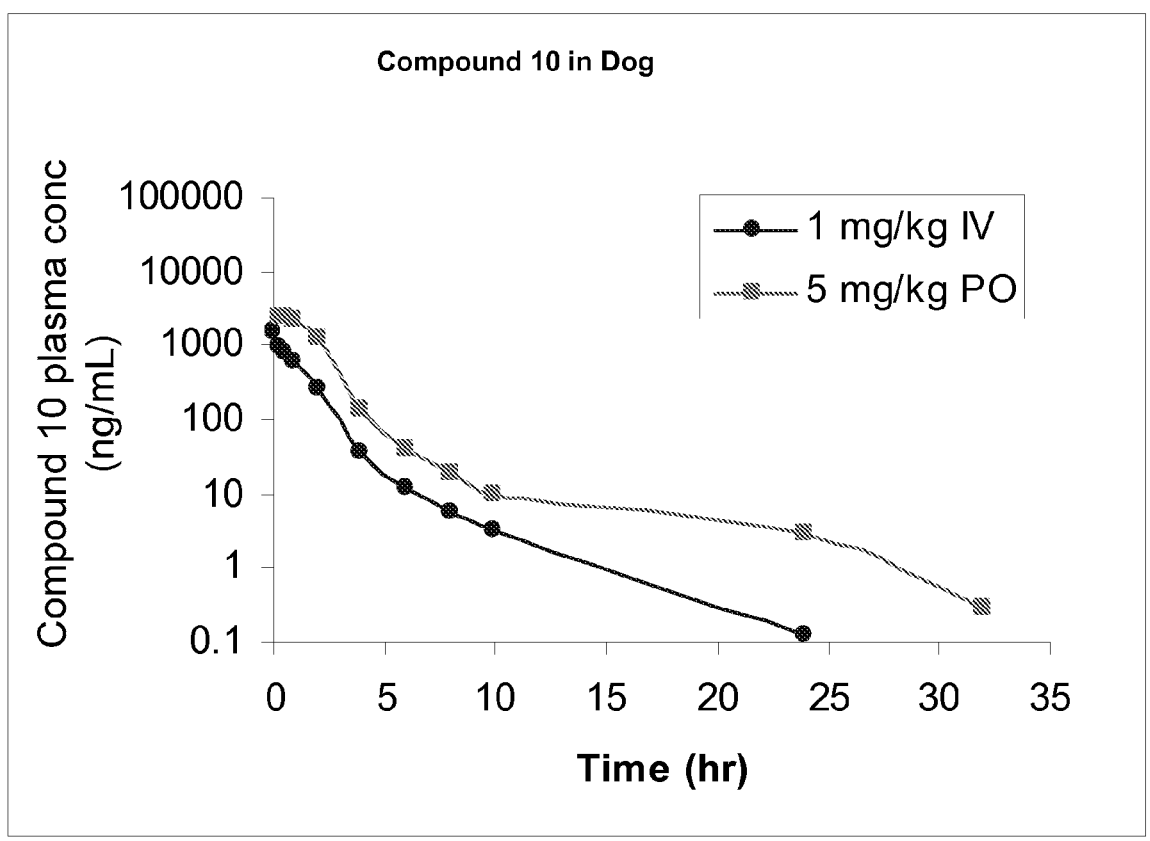
FIG. 2. Mean plasma concentration-time profiles of compound 10 in male beagle dogs after 1 mg/kg intravenous (●) and 5 mg/kg oral (■) administration (n=3/group). Plasma samples were measured using LC/MS/MS.
Figure 3:
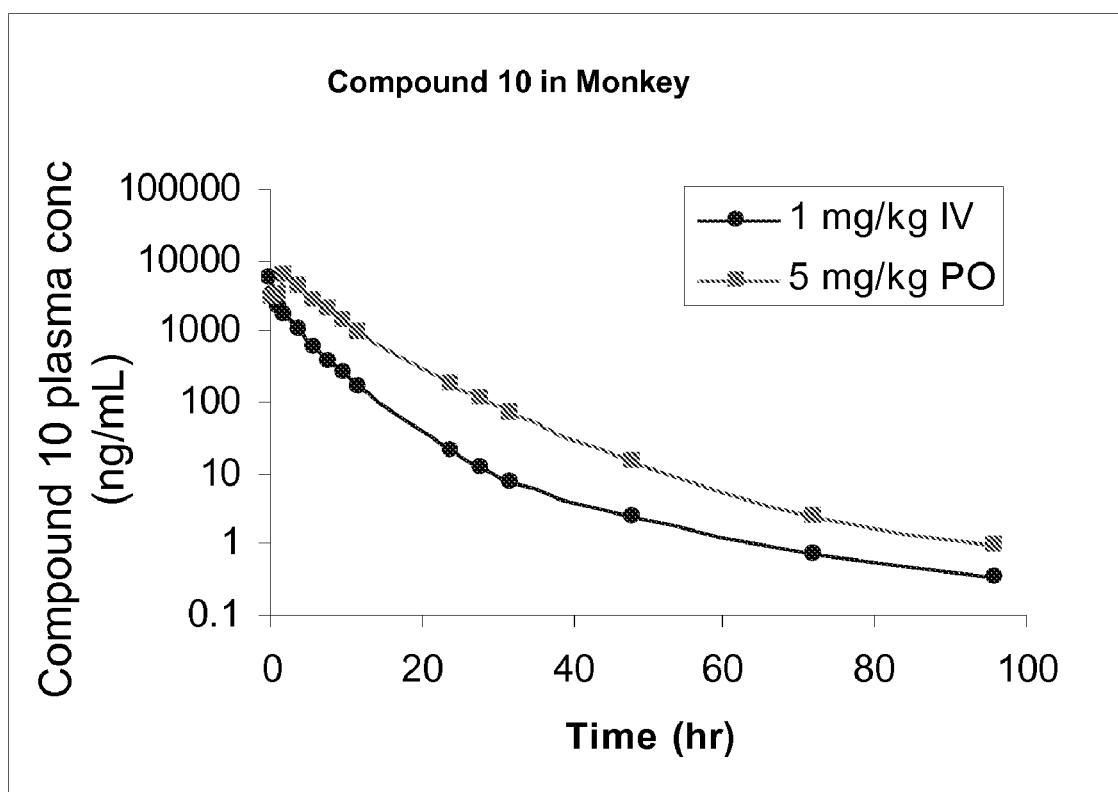
FIG. 3. Shows mean plasma concentration-time profiles of compound 10 in male rhesus monkeys after 1 mg/kg intravenous (●) and 5 mg/kg oral (■) administration (n=3/group). Plasma samples were measured using LC/MS/MS.

The term "alkyl," by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group is one having one or more, preferably 1 to 3, double bonds. Similarly, the term "alkynyl" refers to an unsaturated alkyl group having one or more, preferably 1 to 3, triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$ cycloalkyl) and being fully saturated between ring vertices. The term "cycloalkenyl" refers to a cycloalkyl group that has at least one point of alkenyl unsaturation between the ring vertices. The term "cycloalkynyl" refers to a cycloalkyl group that has at least one point of alkynyl unsaturation between the ring vertices. When "cycloalkyl" is used in combination with "alkyl," as in $C_{3-5}$ cycloalkyl-alkyl, the cycloalkyl portion is meant to have the stated number of carbon atoms (e.g., from three to five carbon atoms), while the alkyl portion is an alkylene moiety having from one to three carbon atoms (e.g., —CH$_2$—, —CH$_2$CH$_2$— or —CH$_2$CH$_2$CH$_2$—).

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

Unless stated otherwise, alkyl, alkoxy, alkenyl, alkynyl, cycloalkyl, cycloalkenyl, cycloalkynyl, and alkylene refer to both substituted and unsubstituted groups in which 1 or more, such as 1 to 5, hydrogen atoms is replaced by a substituent independently selected from the group consisting of =O, =S, acyl (—C(O)—R), acyloxy (—O—C(O)—R), alkoxy, alkoxyamino (—NH—O-alkyl), hydroxyamino (—NH—OH), amino, substituted amino such as —NH$_2$ where one or more of the hydrogens may be optionally replaced by another suitable group, such as alkylamino and dialkylamino, or wherein the amino group may be a cyclic amine, aryl, heterocyclyl, azido (—N$_3$), carboxyl (—C(O)OH), alkoxycarbonyl (—C(O)—O-alkyl), amido (—C(O)-amino), cyano (—CN), cycloalkyl, cycloalkenyl, halogen, hydroxyl, nitro, sulfonylamino (—N(R)—S(O)$_2$—OR), aminosulfonyl (—S(O)$_2$-amino), sulfanyl (—S—R), sulfinyl (—S(O)—R), sulfonyl (—S(O)$_2$—R), and sulfonic acid (—S(O)$_2$—OH), wherein each R may independently be hydrogen, alkyl, cycloalkyl, aryl, heteroaryl, and heterocycle.

The terms "alkoxy," "alkylamino," and "alkylthio" (or thioalkoxy) are used in their conventional sense, and refer to those alkyl groups attached to the remainder of the molecule via an oxygen atom (—O-alkyl), an amino group, or a sulfur atom (—S-alkyl), respectively. Additionally, for dialkylamino groups (typically provided as —NR$^a$R$^b$ or a variant thereof, where R$^a$ and R$^b$ are independently alkyl or substituted alkyl), the alkyl portions can be the same or different and can also be combined to form a 3-7 membered ring with the nitrogen atom to which each is attached. Accordingly, a group represented as —NR$^a$R$^b$ is meant to include a cyclic aminie having 3 to 6 carbon atoms and optionally additional heteroatoms, such as O, S, and N, including but not limited to piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl up to the maximum number of halogens permitted. For example, the term "$C_{1-8}$ haloalkyl" is meant to include trifluoromethyl, 2,2,2-trifluoroethyl, 4-chlorobutyl, 3-bromopropyl, and the like.

The term "hydroxy" or "hydroxyl" refers to the group —OH.

The term "aryl" means, unless otherwise stated, a polyunsaturated, aromatic, hydrocarbon group containing from 6 to 14 carbon atoms, which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom and can contain 5 to 10 carbon atoms. Non-limiting examples of aryl groups include phenyl, naphthyl and biphenyl, while non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. If not specifically stated, substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The term "heterocycle" or "heterocyclyl" or "hetreocyclic" refers to a saturated or unsaturated non-aromatic cyclic group containing at least one sulfur, nitrogen or oxygen heteroatom. Each heterocycle can be attached at any available ring carbon or heteroatom. Each heterocycle may have one or more rings. When multiple rings are present, they can be fused together or linked covalently. Each heterocycle must contain at least one heteroatom (typically 1 to 5 heteroatoms) selected from nitrogen, oxygen or sulfur. Preferably, these groups contain 1-10 carbon atoms, 0-5 nitrogen atoms, 0-2 sulfur atoms and 0-2 oxygen atoms. More preferably, these groups contain 0-3 nitrogen atoms, 0-1 sulfur atoms and 0-1 oxygen atoms.

Non-limiting examples of heterocycle and heteroaryl groups include pyridine, pyridimidine, pyrazine, morpholin-3-one, piperazine-2-one, pyridine-2-one, piperidine, morpholine, piperazine, isoxazole, isothiazole, pyrazole, imidazole, oxazole, thiazole, isoxazoline, pyrazoline, imidazoline, 1,2,3-triazole, 1,2,4-triazole, 1,3,4-oxadiazole, 1,3,4-thiadiazole, 1,2,4-oxadiazole, 1,2,4-thiadiazole, pyrazol-5-one, pyrrolidine-2,5-dione, imidazolidine-2,4-dione, pyrrolidine, pyrrole, furan, thiophene, and the like.

The term "heterocycloalkyl" refers to the group alkylene-heterocycle, wherein both heterocycle and alkylene are as defined above.

The above terms (e.g., "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below.

Substituents for the aryl, heteroaryl, and heterocycle groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C (NH$_2$)=NR', —S(O)R', —S(O)$_2$R', —S(O)$_2$NR'R", —NR'S (O)$_2$R", —N$_3$, perfluoro(C$_1$-C$_4$)alkoxy, and perfluoro(C$_1$-C$_4$)alkyl, in a number ranging from zero to the total number of open valences on the ring system; and where R', R" and R'" are independently selected from hydrogen, C$_{1-8}$ alkyl, C$_{3-6}$ cycloalkyl, C$_{2-8}$ alkenyl, C$_{2-8}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms. This group of substituents is also used to describe the substituents for optionally substituted phenyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

"Amino" refers to the group —NH$_2$ and unless otherwise specificied, also refers to "substituted amino."

"Substituted amino" refers to the group —NR'R" where R' and R" are independently selected from the group consisting of hydrogen, alkyl, alkenyl, alkynyl, aryl, cycloalkyl, cycloalkenyl, heteroaryl, heterocyclic, —SO$_2$-alkyl, —SO$_2$-alkenyl, —SO$_2$-cycloalkyl, —SO$_2$-cycloalkenyl, —SO$_2$-aryl, —SO$_2$-heteroaryl, and —SO$_2$-heterocyclic, and wherein R' and R" are optionally joined, together with the nitrogen bound thereto to form a heterocyclic or substituted heterocyclic group, provided that R' and R" are both not hydrogen, and wherein alkyl, alkenyl, alkynyl, cycloalkyl, cycloalkenyl, aryl, heteroaryl, and heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Carbonyl" refers to the divalent group —C(O)— which is equivalent to —C(=O)—.

"Cyano" refers to the group —CN.

"Oxo" refers to the atom (=O) or (—O$^-$).

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a ester form. For example, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. The invention includes those esters and acyl groups known in the art for modifying the solubility or hydrolysis characteristics for use as sustained-release or prodrug formulations.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

2. Embodiments of the Invention a. Compounds

In one aspect, the present invention provides compounds having the following formula:

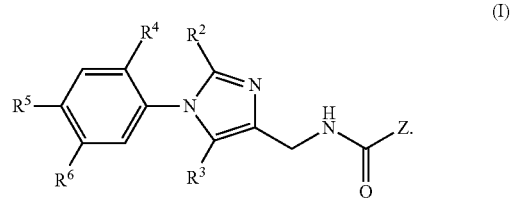

In formula (I), the symbol Z is selected from the group consisting of:

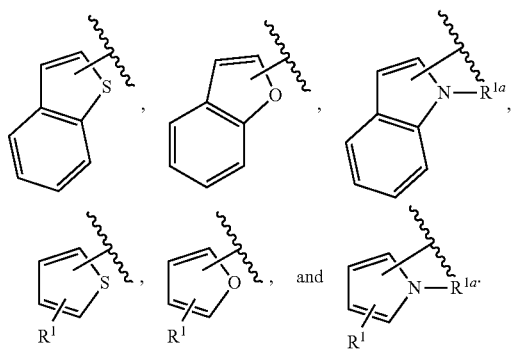

The symbol $R^1$ is selected from the group consisting of halogen, $C_{1-8}$ alkyl, $C_{2-8}$ alkenyl, and $C_{2-8}$ alkynyl. The symbol $R^{1a}$ is hydrogen or $C_{1-4}$ alkyl.

The symbol $R^2$ and $R^3$ are independently selected from the group consisting of hydrogen, halogen, $C_{1-4}$ alkyl, $SR^{4a}$, $S(O)R^{4a}$, $S(O)_2R^{4a}$, $COR^{4a}$, $CO_2R^{4a}$, $CONR^{4a}R^{4b}$, CN, and $S(O)_2NR^{4a}R^{4b}$.

The symbol $R^4$ represents a moiety independently selected from the group consisting of) hydrogen, halogen, $OR^{4a}$, $SR^{4a}$, $S(O)R^{4a}$, $S(O)_2R^{4a}$, $NR^{4a}R^{4b}$, $CO_2R^{4a}$,

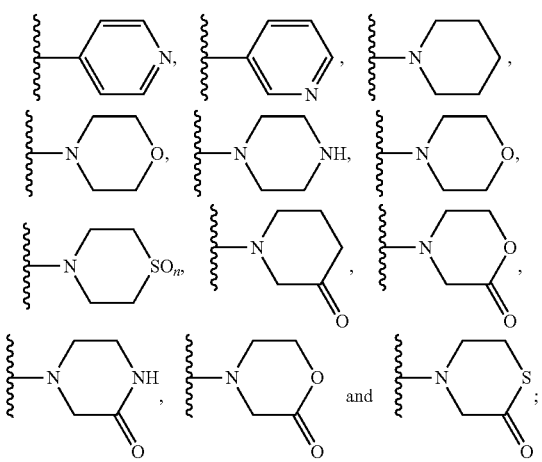

wherein each of these ring systems is optionally substituted with from 1 to 3 substituents independently selected from the group consisting of halogen, amino, oxo, $C_{1-8}$ alkyl, $C_{1-8}$ haloalkyl, hydroxy, $C_{1-8}$ alkoxy, heterocycloalkyl, heteroaryl, and heteroaryl-$C_{1-4}$ alkyl.

The symbols $R^{4a}$ or $R^{4b}$ are independently hydrogen or $C_{1-4}$ alkyl, optionally substituted with from 1 to 2 substituents independently selected from the group consisting of halogen, hydroxyl, alkoxy, heterocyclyl, oxo, amino, and carboxyl.

The subscript n is an integer from 0 to 2.

The symbol $R^5$ is selected from the group consisting of:

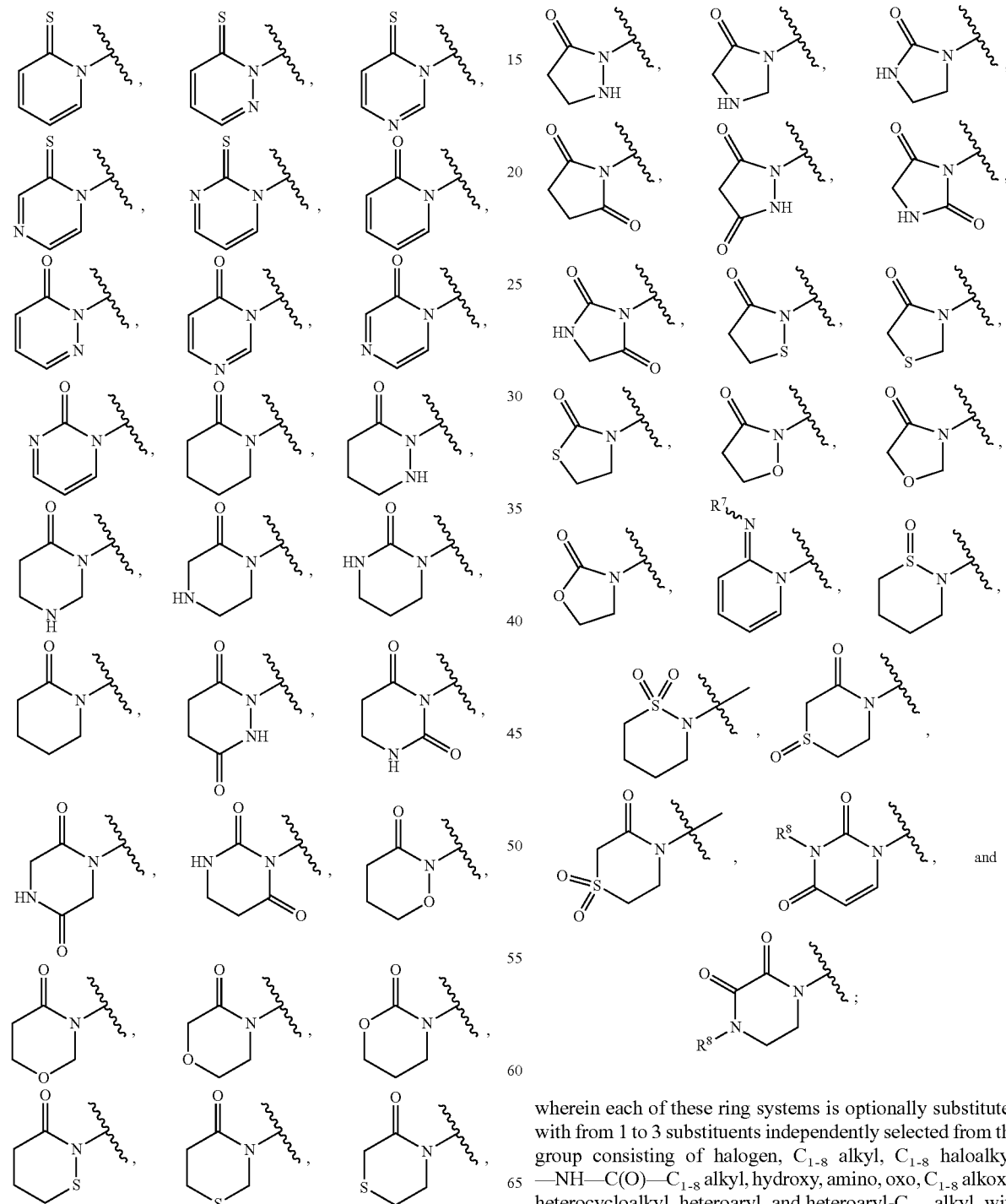

wherein each of these ring systems is optionally substituted with from 1 to 3 substituents independently selected from the group consisting of halogen, $C_{1-8}$ alkyl, $C_{1-8}$ haloalkyl, —NH—C(O)—$C_{1-8}$ alkyl, hydroxy, amino, oxo, $C_{1-8}$ alkoxy, heterocycloalkyl, heteroaryl, and heteroaryl-$C_{1-4}$ alkyl, with the proviso that when $R^5$ is

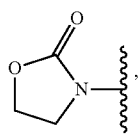

then there cannot be an alkyl (or substituted alkyl) substituent in the 5-position of the $R^5$ ring.

The structure shown above as:

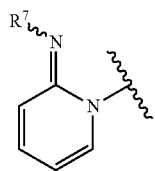

includes both the cis and trans isomers, i.e.,

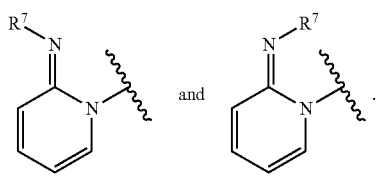

The symbol $R^6$ is selected from the group consisting of hydrogen, halogen, and $C_{1-4}$ alkyl.

The symbol $R^7$ is selected from the group consisting of hydrogen, $C_{1-4}$ alkyl, cyano, optionally substituted phenyl, and $C(O)R^9$ wherein $R^9$ is $C_{1-4}$ alkyl or amino.

The symbol $R^8$ is selected from the group consisting of hydrogen and $C_{1-4}$ alkyl.

The wavy line indicates the point of attachment to the rest of the molecule. The present invention also contemplates pharmaceutically acceptable salts, esters, and prodrugs of the compounds of formula (I).

With the above formula, are a number of specific embodiments of the invention. In one group of embodiments, $R^2$, $R^3$ and $R^6$ are hydrogen. In one group of embodiments, $R^2$ is selected from the group consisting of hydrogen, $C_{1-4}$ alkyl, $SR^{4a}$, $S(O)R^{4a}$, $S(O)_2R^{4a}$, $COR^{4a}$, $CO_2R^{4a}$, $CONR^{4a}R^{4b}$, CN, and $S(O)_2NR^{4a}R^{4b}$. In one group of embodiments, $R^2$ is selected from the group consisting of hydrogen, methyl, —S-methyl, —S(O)-methyl, and —S(O)$_2$-methyl. In one group of embodiments, $R^3$ is hydrogen or methyl. In one group of embodiments, $R^6$ is hydrogen or fluoro. In one group of embodiments, $R^4$ is selected from the group consisting of hydrogen, halogen, $OR^{4a}$, $S(O)R^{4a}$, $S(O)_2R^{4a}$, $NR^{4a}R^{4b}$, $CO_2R^{4a}$,

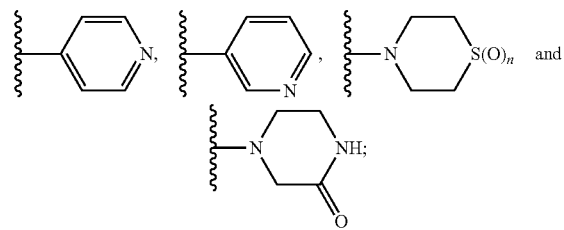

wherein each of these ring systems is optionally substituted with from 1 to 3 substituents independently selected from the group consisting of halogen, amino, oxo, $C_{1-8}$ alkyl, $C_{1-8}$ haloalkyl, hydroxy, $C_{1-8}$ alkoxy, heterocycloalkyl, heteroaryl, and heteroaryl-$C_{1-4}$ alkyl; and each $R^{4a}$ or $R^{4b}$ is independently hydrogen or $C_{1-4}$ alkyl, optionally substituted with hydroxyl, alkoxy, or heterocyclyl, and the wavy line indicates the point of attachment to the rest of the molecule. The superscript n is 0, 1, and 2.

In one embodiment, $R^4$ is selected from the group consisting of hydrogen, hydroxyl, fluoro, $S(O)CH_3$, $S(O)_2CH_3$, $NH(CH_2)_2OH$, —$C(O)_2CH_3$, —$O(CH_2)_2OCH_3$, —$OCH_2CH(OH)CH_2OH$,

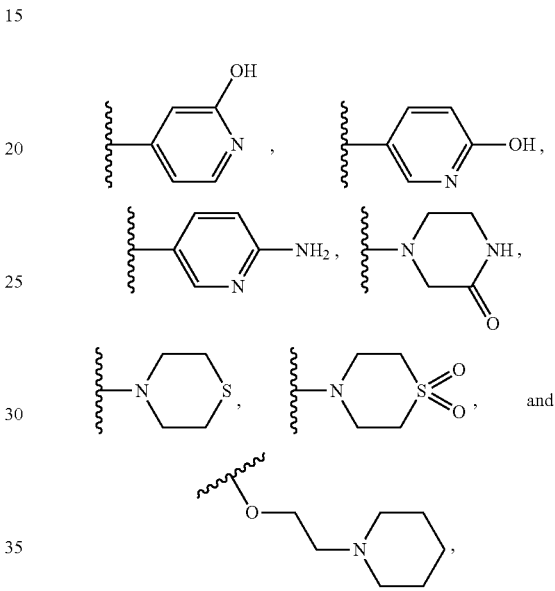

In another group of embodiments, $R^5$ is

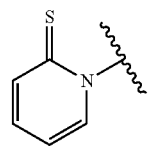 [SMILES: *n1ccccc1=S]

optionally substituted with from 1 to 3 substituents independently selected from the group consisting of halogen, amino, $C_{1-8}$ alkyl, $C_{1-8}$ haloalkyl, hydroxy, $C_{1-8}$ alkoxy, heterocycloalkyl, heteroaryl and heteroaryl-$C_{1-4}$ alkyl.

In another embodiment, the invention contemplates a compound having the formula:

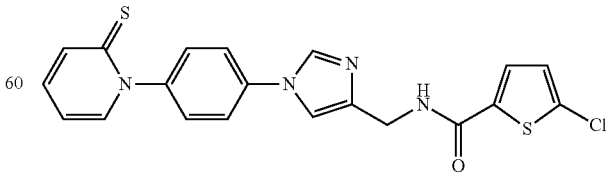

and pharmaceutically acceptable salts, esters and prodrugs thereof.

In another group of embodiments, R⁵ is

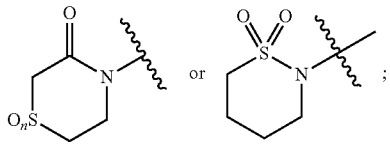

optionally substituted with from 1 to 3 substituents independently selected from the group consisting of halogen, amino, $C_{1-8}$ alkyl, $C_{1-8}$ haloalkyl, hydroxy, $C_{1-8}$ alkoxy, heterocycloalkyl, heteroaryl and heteroaryl-$C_{1-4}$ alkyl; and the subscript n is 0, 1, or 2.

In another embodiment, the invention contemplates compounds having the formulas:

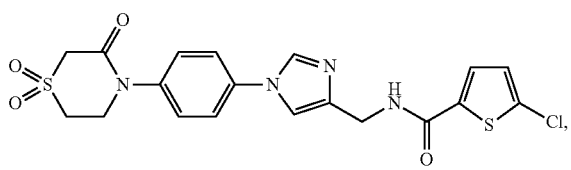

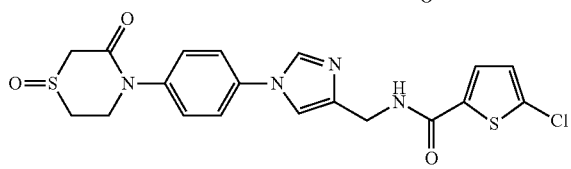

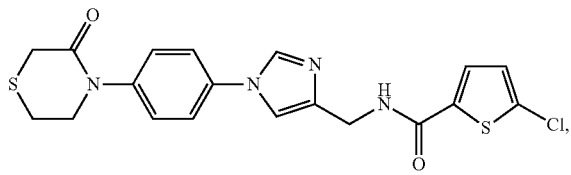

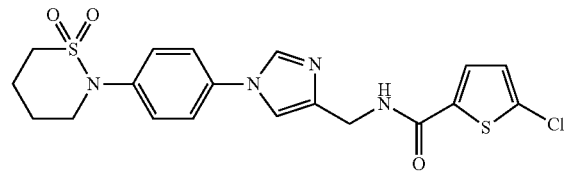

and pharmaceutically acceptable salts, esters and prodrugs thereof.

In another group of embodiments, R⁵ is selected from the group consisting of

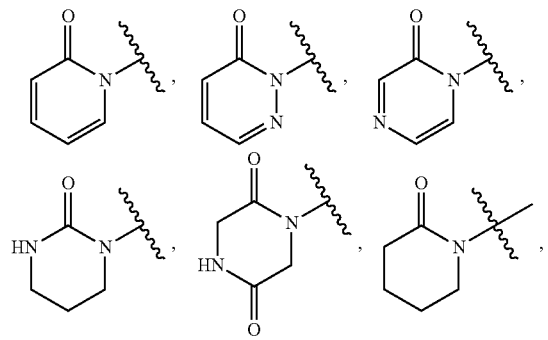

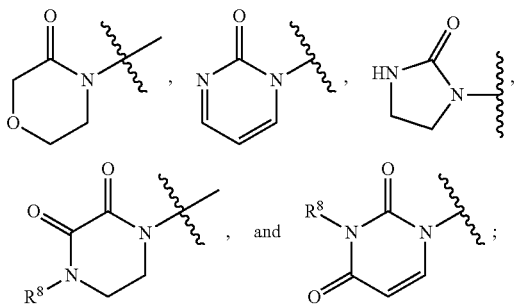

wherein each of these ring systems is optionally substituted with from 1 to 3 substituents independently selected from the group consisting of halogen, $C_{1-8}$ alkyl, —NH—C(O)—$C_{1-8}$ alkyl, $C_{1-8}$ haloalkyl, hydroxy, amino, oxo, $C_{1-8}$ alkoxy, heterocycloalkyl, heteroaryl and heteroaryl-$C_{1-4}$ alkyl and R⁸ is hydrogen or $C_{1-4}$ alkyl.

In another embodiment, the invention contemplates compounds having the formula selected from the group consisting of:

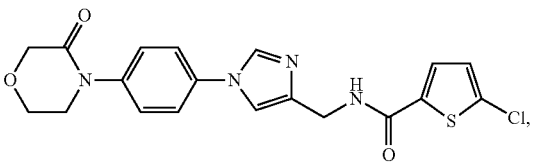

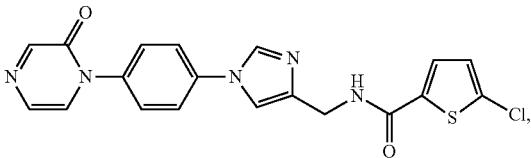

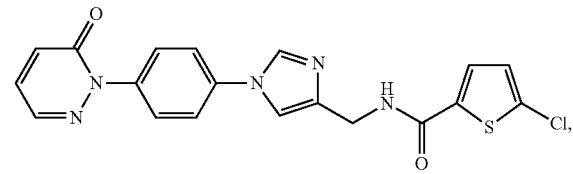

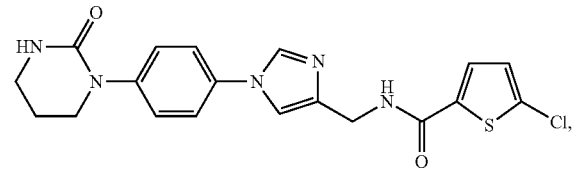

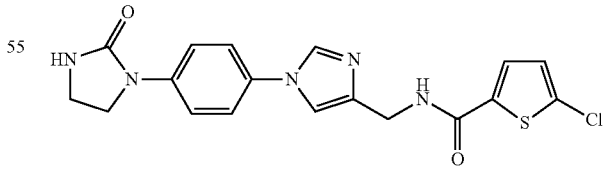

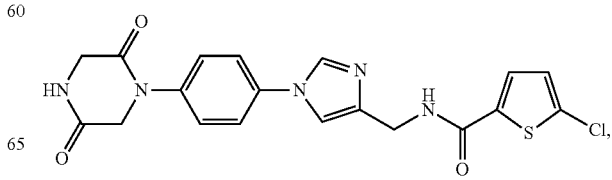

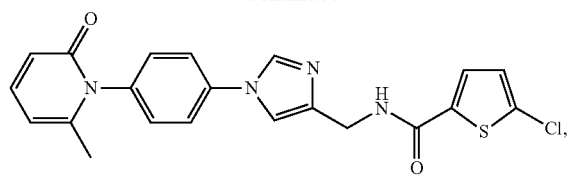
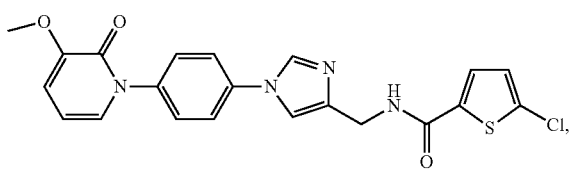
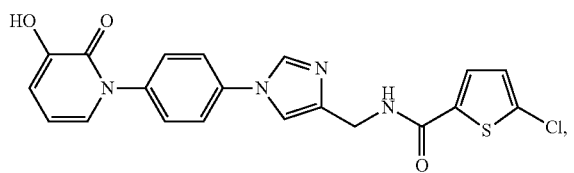
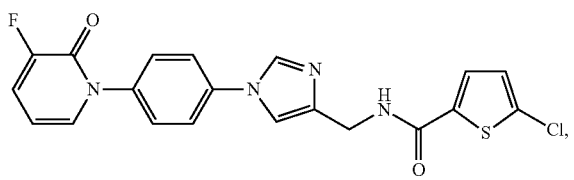
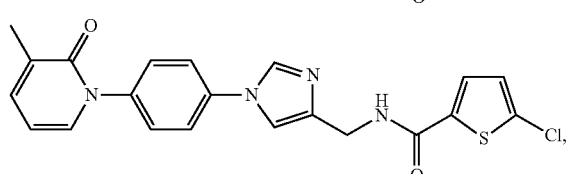
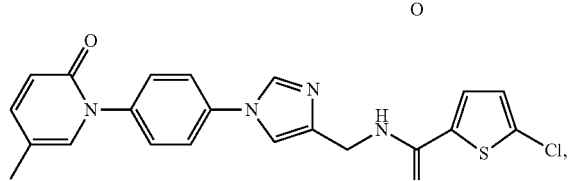
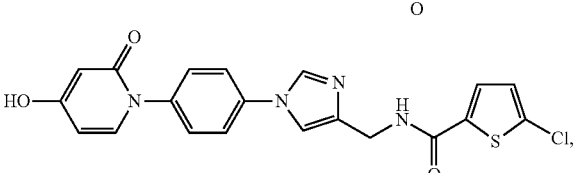
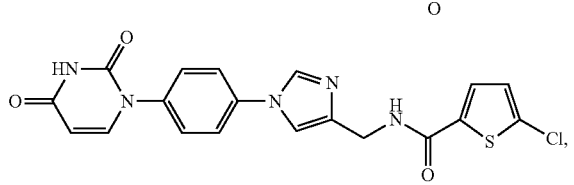
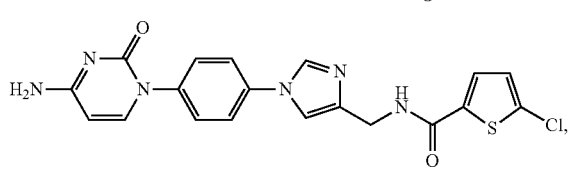
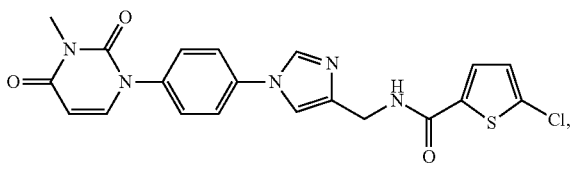
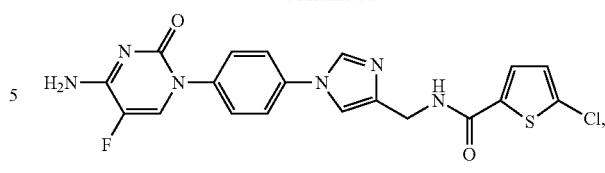
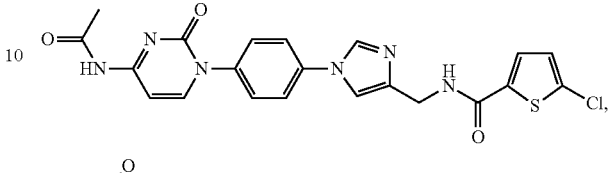
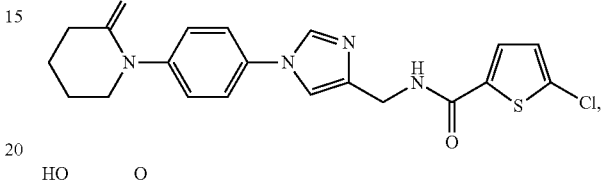
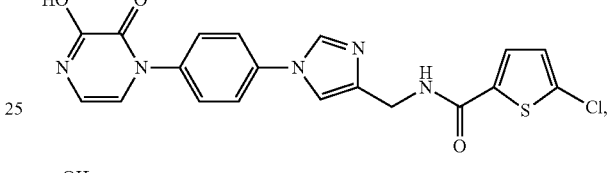
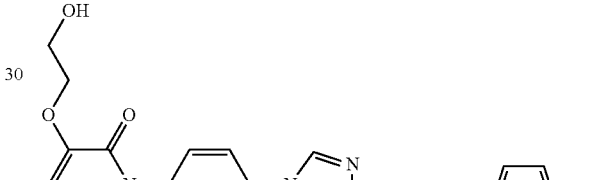
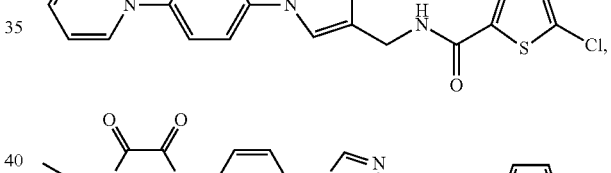
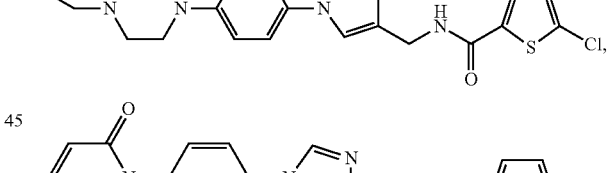
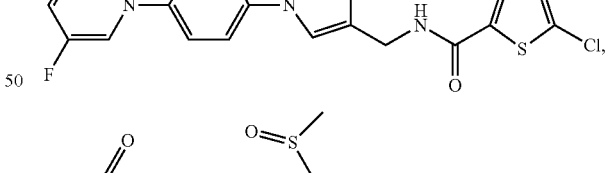
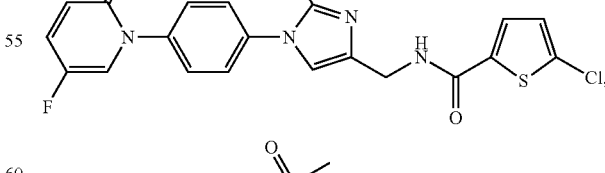
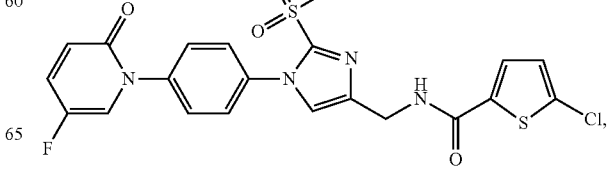

-continued

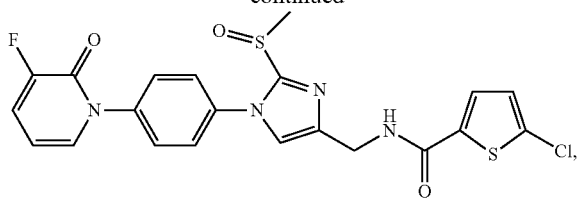

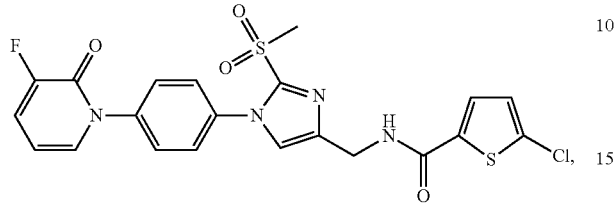

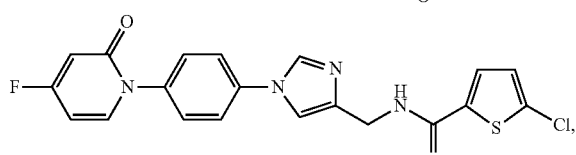

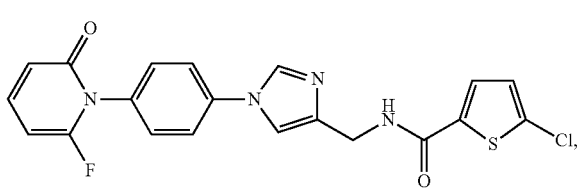

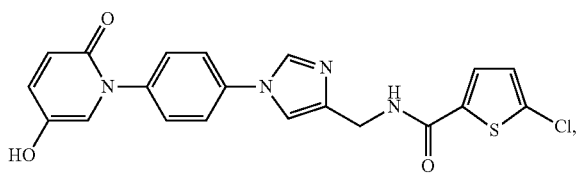

and pharmaceutically acceptable salts, esters and prodrugs thereof.

In one group of embodiments, $R^5$ is

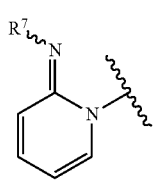

wherein $R^7$ is selected from the group consisting of hydrogen, $C_{1-4}$ alkyl, cyano, optionally substituted phenyl, and $C(O)R^9$. $R^9$ is $C_{1-4}$ alkyl or amino.

In those embodiments, the invention includes compounds selected from:

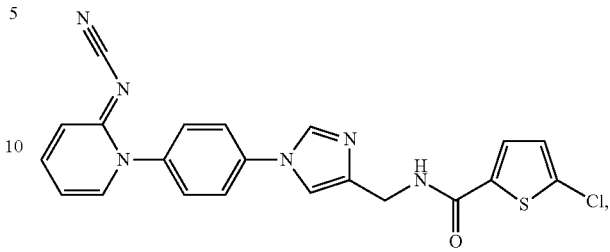

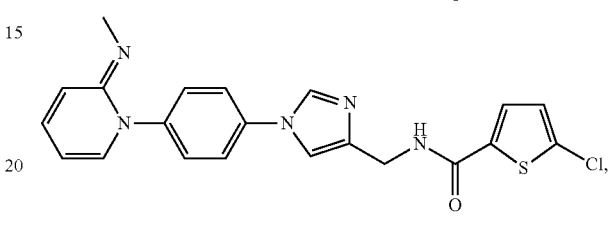

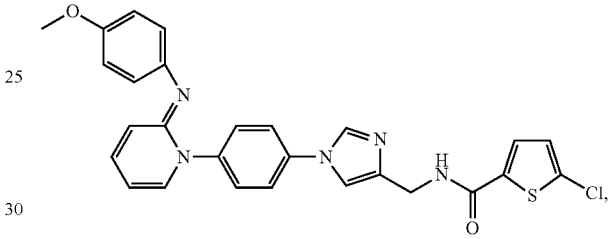

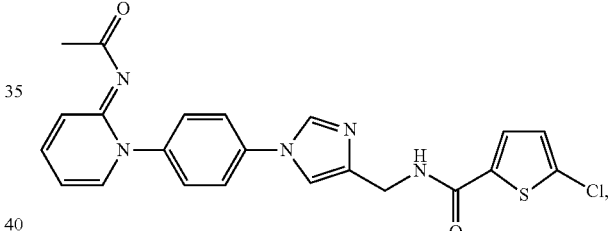

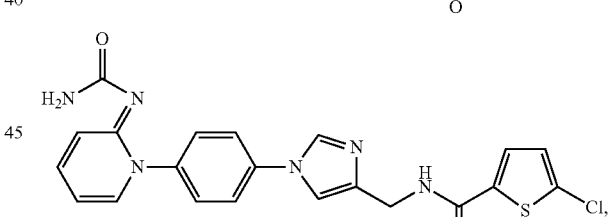

and pharmaceutically acceptable salts, esters and prodrugs thereof.

In one group of embodiments, Z is selected from the group consisting of:

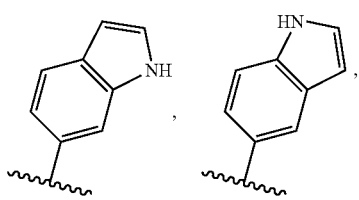

-continued

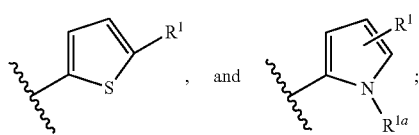

and $R^1$ is halogen or $C_{2-8}$ alkynyl and $R^{1a}$ is hydrogen or methyl.

In another group of embodiments, Z is:

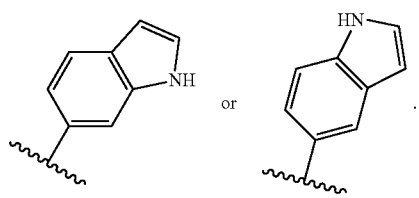 [SMILES: *c1ccc2cc[nH]c2c1 ; *c1ccc2[nH]ccc2c1]

In another embodiment, the invention contemplates compounds having the formula:

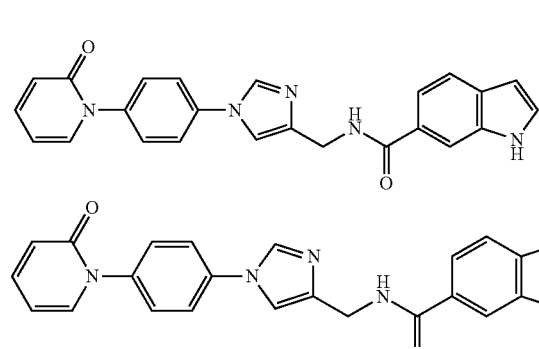

and pharmaceutically acceptable salts, esters and prodrugs thereof.

In another group of embodiments, Z is:

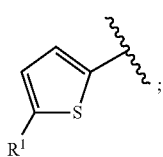

and $R^1$ is halogen or $C_{2-8}$ alkynyl.

In another group of embodiments, Z is:

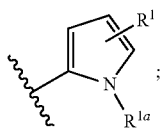

where $R^1$ is halogen or $C_{2-8}$ alkynyl and $R^{1a}$ is hydrogen or methyl.

The invention contemplates compounds having the formula:

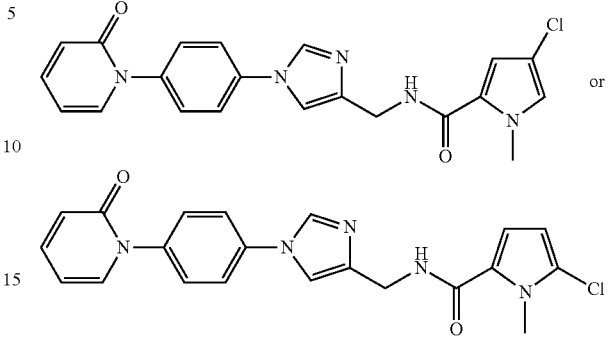

and pharmaceutically acceptable salts, esters and prodrugs thereof.

In another group of embodiments, the compound has the following formula:

(II)

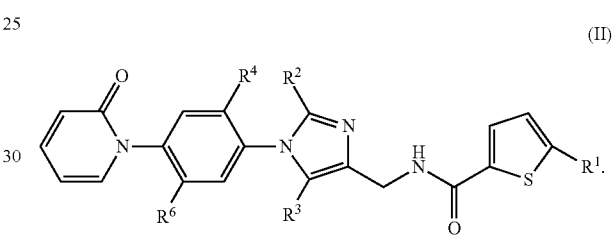

With reference to formula (II), $R^1$ is selected from the group consisting of halogen, $C_{1-8}$ alkyl, $C_{2-8}$ alkenyl, and $C_{2-8}$ alkynyl; $R^2$ and $R^3$ are independently selected from the group consisting of hydrogen, halogen, $C_{1-4}$ alkyl, $SR^{4a}$, $S(O)R^{4a}$, and $S(O)_2R^{4a}$; and $R^4$ is selected from the group consisting of hydrogen, halogen, $OR^{4a}$, $SR^{4a}$, $S(O)R^{4a}$, $S(O)_2R^{4a}$, $NR^{4a}R^{4b}$, $CO_2R^{4a}$,

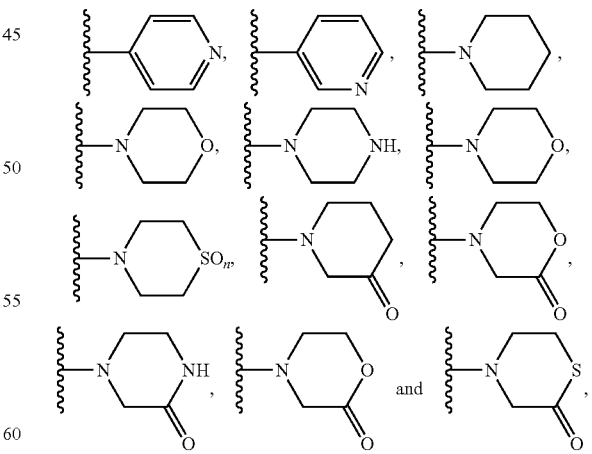

wherein each of these ring systems is optionally substituted with from 1 to 3 substituents independently selected from the group consisting of halogen, amino, oxo, $C_{1-8}$ alkyl, $C_{1-8}$ haloalkyl, hydroxy, $C_{1-8}$ alkoxy, heterocycloalkyl, heteroaryl, and heteroaryl-$C_{1-4}$ alkyl;

each $R^{4a}$ or $R^{4b}$ is independently hydrogen or $C_{1-4}$ alkyl, optionally substituted with from 1 to 2 substituents independently selected from the group consisting of halogen, hydroxyl, alkoxy, heterocyclyl, oxo, amino and carboxyl;

$R^6$ is selected from the group consisting of hydrogen, halogen, and $C_{1-4}$ alkyl;

the subscript n is an integer from 0 to 2;

the wavy line indicates the point of attachment to the rest of the molecule;

and pharmaceutically acceptable salts, esters and prodrugs thereof.

In another group of embodiments, the $R^1$ is $C_{2-8}$ alkynyl.

In another embodiment, the compound has the formula:

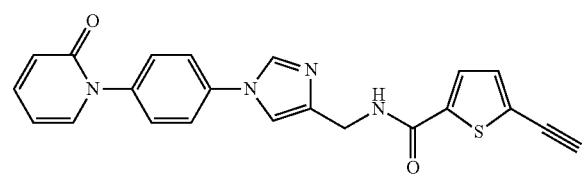 [SMILES: C#Cc1ccc(C(=O)NCc2cn(-c3ccc(-n4ccccc4=O)cc3)cn2)s1]

and the invention contemplates pharmaceutically acceptable salts, esters and prodrugs thereof.

In another group of embodiments, $R^1$ is halogen.

In another embodiment, the compound is selected from the group consisting of:

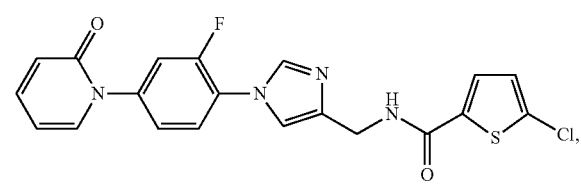

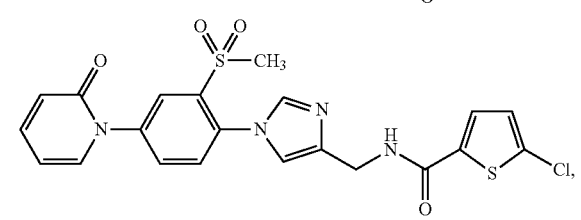

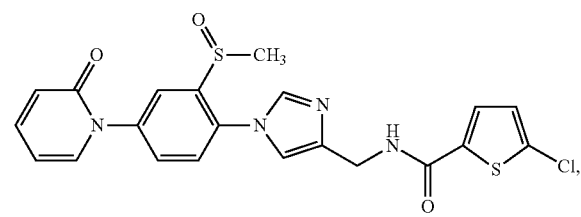

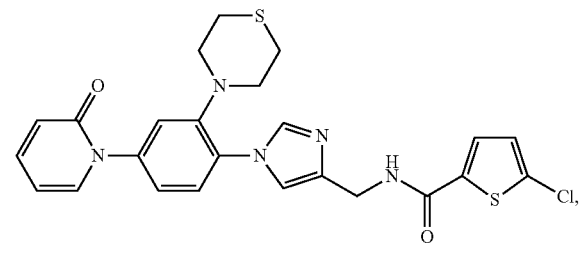

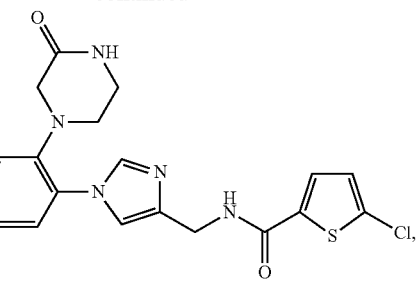

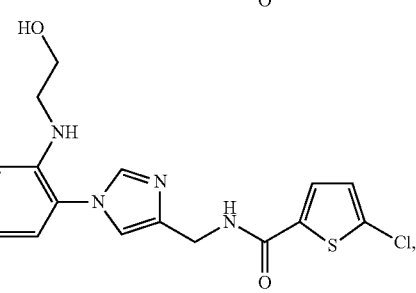

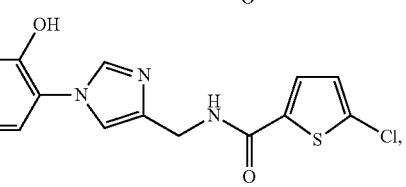

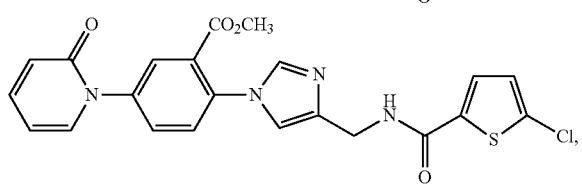

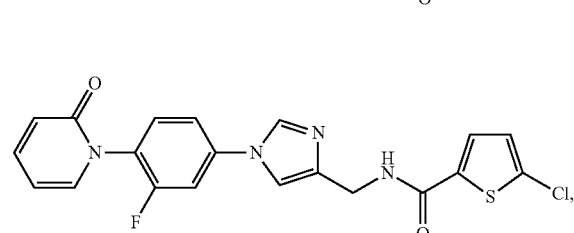

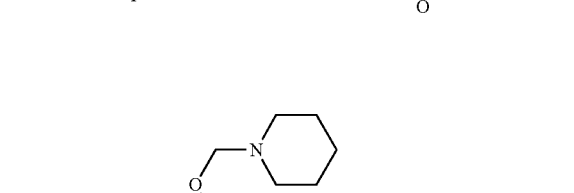

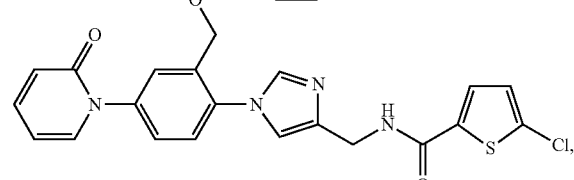

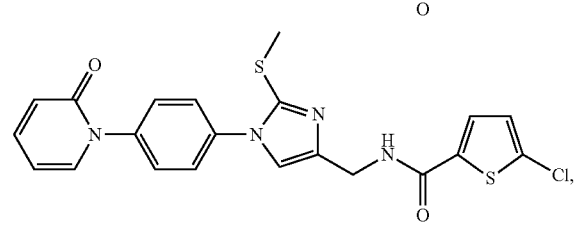

-continued

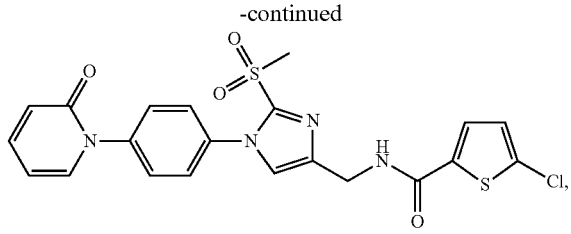
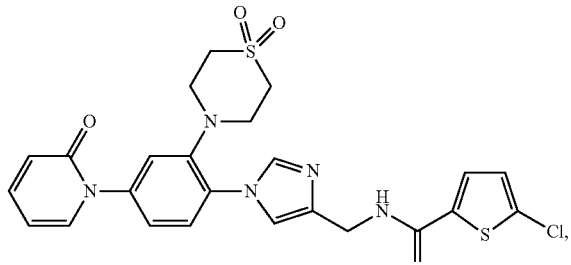
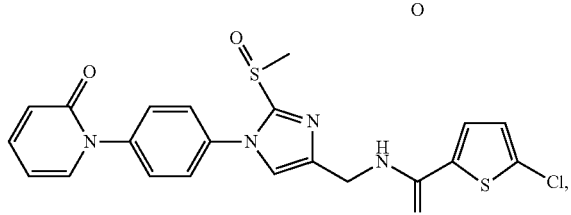
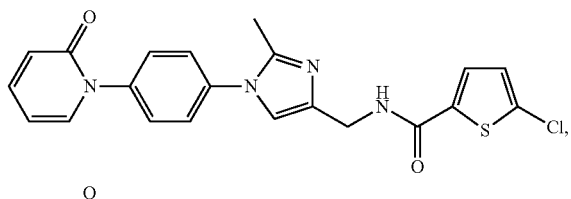
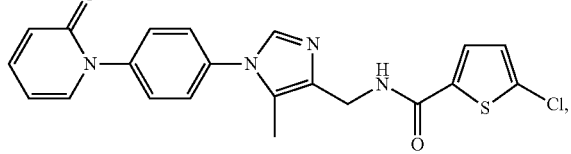
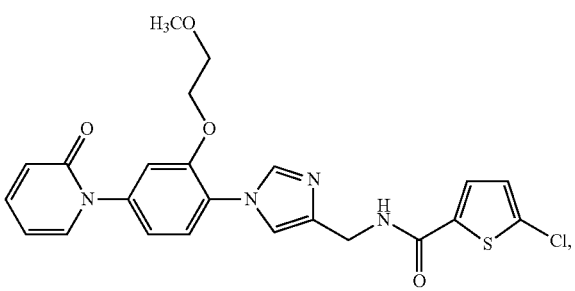
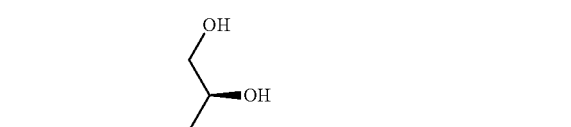
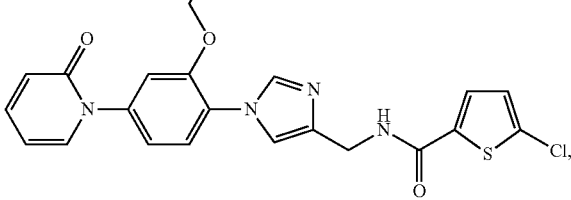

-continued

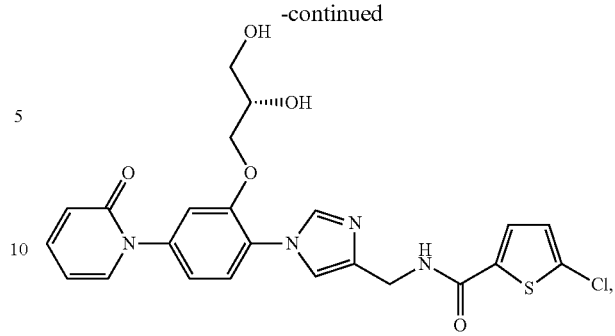
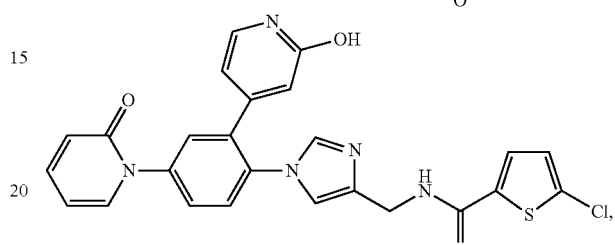
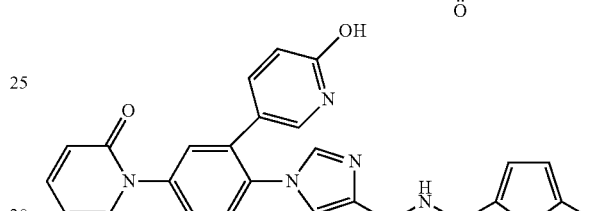
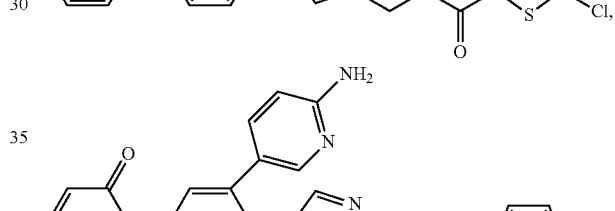

and pharmaceutically acceptable salts, esters and prodrugs thereof.

In another group of embodiments, $R^4$ is hydrogen.

In another embodiment, the compound has the formula:

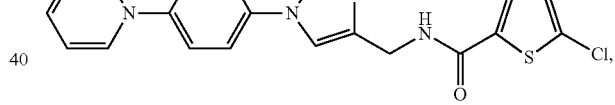

and pharmaceutically acceptable salts, esters and prodrugs thereof.

In another group of embodiments, the compound of the invention is in an isolated and purified form.

Within the present invention, the compounds provided in the examples below are each preferred embodiments, along with their pharmaceutically acceptable salts, esters and prodrugs thereof. Preferred examples of compounds of formula (I) include:

5-Chloro-N-((1-(4-(2-oxopyridin-1(2H)-yl)phenyl)-1H-imidazol-4-yl)methyl)thiophene-2-carboxamide;
5-Chloro-N-((1-(4-(3-oxomorpholino)phenyl)-1H-imidazol-4-yl)methyl)thiophene-2-carboxamide;
5-Chloro-N-((1-(4-(2-oxopyrazin-1(2H)-yl)phenyl)-1H-imidazol-4-yl)methyl)thiophene-2-carboxamide;
5-Chloro-N-((1-(4-(6-oxopyridazin-1(6H)-yl)phenyl)-1H-imidazol-4-yl)methyl)thiophene-2-carboxamide;
5-Chloro-N-((1-(4-(2-oxo-6-methylpyridin-1(2H)-yl)phenyl)-1H-imidazol-4-yl)methyl)thiophene-2-carboxamide;
5-Chloro-N-((1-(4-(3-oxothiomorpholino)phenyl)-1H-imidazol-4-yl)methyl)thiophene-2-carboxamide;
5-Chloro-N-((1-(4-(1,1-dioxo-3-oxothiomorpholino)phenyl)-1H-imidazol-4-yl)methyl)thiophene-2-carboxamide;
5-Chloro-N-((1-(4-(1,3-dioxothiomorpholino)phenyl)-1H-imidazol-4-yl)methyl)thiophene-2-carboxamide;
5-Chloro-N-((1-(4-(2-oxo-tetrahydropyrimidin-1(2H)-yl)phenyl)-1H-imidazol-4-yl)methyl)thiophene-2-carboxamide;
5-Chloro-N-((1-(4-(2-oxoimidazolidin-1-yl)phenyl)-1H-imidazol-4-yl)methyl)thiophene-2-carboxamide;
5-Chloro-N-((1-(4-(2,5-dioxopiperazin-1-yl)phenyl)-1H-imidazol-4-yl)methyl)thiophene-2-carboxamide;
5-Chloro-N-((1-(2-fluoro-4-(2-oxopyridin-1(2H)-yl)phenyl)-1H-imidazol-4-yl)methyl)thiophene-2-carboxamide;
5-Chloro-N-((1-(2-(methylsulfonyl)-4-(2-oxopyridin-1(2H)-yl)phenyl)-1H-imidazol-4-yl)methyl)thiophene-2-carboxamide;
5-chloro-N-((1-(2-(methylsulfinyl)-4-(2-oxopyridin-1(2H)-yl)phenyl)-1H-imidazol-4-yl)methyl)thiophene-2-carboxamide;
5-Chloro-N-((1-(4-(2-oxopyridin-1(2H)-yl)-2-thiomorpholinophenyl)-1H-imidazol-4-yl)methyl)thiophene-2-carboxamide;
5-Chloro-N-((1-(4-(2-oxopyridin-1(2H)-yl)-2-(1,1-dioxothiomorpholin-4-yl)phenyl)-1H-imidazol-4-yl)methyl)thiophene-2-carboxamide;
5-Chloro-N-((1-(2-(3-oxopiperazin-1-yl)-4-(2-oxopyridin-1(2H)-yl)phenyl)-1H-imidazol-4-yl)methyl)thiophene-2-carboxamide;
5-Chloro-N-((1-(2-(2-hydroxyethylamino)-4-(2-oxopyridin-1(2H)-yl)phenyl)-1H-imidazol-4-yl)methyl)thiophene-2-carboxamide;
5-Chloro-N-((1-(2-hydroxy-4-(2-oxopyridin-1(2H)-yl)phenyl)-1H-imidazol-4-yl)methyl)thiophene-2-carboxamide;
5-Chloro-N-((1-(2-methoxycarbonyl-4-(2-oxopyridin-1(2H)-yl)phenyl)-1H-imidazol-4-yl)methyl)thiophene-2-carboxamide;
5-Chloro-N-((1-(4-(2-thioxopyridin-1(2H)-yl)phenyl)-1H-imidazol-4-yl)methyl)thiophene-2-carboxamide;
N-((1-(4-(2-oxopyridin-1(2H)-yl)phenyl)-1H-imidazol-4-yl)methyl)-1H-indole-6-carboxamide;
5-Ethynyl-N-((1-(4-(2-oxopyridin-1(2H)-yl)phenyl)-1H-imidazol-4-yl)methyl)thiophene-2-carboxamide;
5-Chloro-N-((1-(4-(2-(cyanoimino)pyridin-1(2H)-yl)phenyl)-1H-imidazol-4-yl)methyl)thiophene-2-carboxamide;
5-Chloro-N-((1-(4-(2-(methylimino)pyridin-1(2H)-yl)phenyl)-1H-imidazol-4-yl)methyl)thiophene-2-carboxamide;
5-Chloro-N-((1-(4-(2-(4-methoxyphenylimino)pyridin-1(2H)-yl)phenyl)-1H-imidazol-4-yl)methyl)thiophene-2-carboxamide;
N-((1-(4-(2-(acetylimino)pyridin-1(2H)-yl)phenyl)-1H-imidazol-4-yl)methyl)-5-chlorothiophene-2-carboxamide;
4-Chloro-1-methyl-N-((1-(4-(2-oxopyridin-1(2H)-yl)phenyl)-1H-imidazol-4-yl)methyl)-1H-pyrrole-2-carboxamide;
5-Chloro-1-methyl-N-((1-(4-(2-oxopyridin-1(2H)-yl)phenyl)-1H-imidazol-4-yl)methyl)-1H-pyrrole-2-carboxamide;
5-Chloro-N-((1-(4-(1,1-dioxothiomorpholino)phenyl)-1H-imidazol-4-yl)methyl)thiophene-2-carboxamide;
5-Chloro-N-((1-(3-fluoro-4-(2-oxopyridin-1(2H)-yl)phenyl)-1H-imidazol-4-yl)methyl)thiophene-2-carboxamide;
5-Chloro-N-((1-(4-(3-methoxy-2-oxopyridin-1(2H)-yl)phenyl)-1H-imidazol-4-yl)methyl)thiophene-2-carboxamide;
5-Chloro-N-((1-(4-(3-hydroxy-2-oxopyridin-1(2H)-yl)phenyl)-1H-imidazol-4-yl)methyl)thiophene-2-carboxamide;
5-Chloro-N-((1-(4-(3-fluoro-2-oxopyridin-1(2H)-yl)phenyl)-1H-imidazol-4-yl)methyl)thiophene-2-carboxamide;
5-Chloro-N-((1-(4-(3-methyl-2-oxopyridin-1(2H)-yl)phenyl)-1H-imidazol-4-yl)methyl)thiophene-2-carboxamide;
5-Chloro-N-((1-(4-(5-methyl-2-oxopyridin-1(2H)-yl)phenyl)-1H-imidazol-4-yl)methyl)thiophene-2-carboxamide;
5-Chloro-N-((1-(4-(4-hydroxy-2-oxopyridin-1(2H)-yl)phenyl)-1H-imidazol-4-yl)methyl)thiophene-2-carboxamide;
5-Chloro-N-((1-(4-(2,4-dioxo-3,4-dihydropyrimidin-1(2H)-yl)phenyl)-1H-imidazol-4-yl)methyl)thiophene-2-carboxamide
N-((1-(4-(4-amino-2-oxopyrimidin-1(2H)-yl)phenyl)-1H-imidazol-4-yl)methyl)-5-chlorothiophene-2-carboxamide;
5-Chloro-N-((1-(4-(3-methyl-2,4-dioxo-3,4-dihydropyrimidin-1(2H)-yl)phenyl)-1H-imidazol-4-yl)methyl)thiophene-2-carboxamide;
N-((1-(4-(4-amino-5-fluoro-2-oxopyrimidin-1(2H)-yl)phenyl)-1H-imidazol-4-yl)methyl)-5-chlorothiophene-2-carboxamide;
N-((1-(4-(4-acetamido-2-oxopyrimidin-1(2H)-yl)phenyl)-1H-imidazol-4-yl)methyl)-5-chlorothiophene-2-carboxamide;
5-Chloro-N-((1-(4-(2-oxopiperidin-1-yl)phenyl)-1H-imidazol-4-yl)methyl)thiophene-2-carboxamide;
5-Chloro-N-((1-(4-(2-oxopyridin-1(2H)-yl)-2-(2-(piperidin-1-yl)ethoxy)phenyl)-1H-imidazol-4-yl)methyl)thiophene-2-carboxamide;
N-((1-(4-(2-oxopyridin-1(2H)-yl)phenyl)-1H-imidazol-4-yl)methyl)-1H-indole-5-carboxamide;
5-Chloro-N-((2-(methylthio)-1-(4-(2-oxopyridin-1(2H)-yl)phenyl)-1H-imidazol-4-yl)methyl)thiophene-2-carboxamide;
5-Chloro-N-((2-(methylsulfonyl)-1-(4-(2-oxopyridin-1(2H)-yl)phenyl)-1H-imidazol-4-yl)methyl)thiophene-2-carboxamide;
5-Chloro-N-((2-(methylsulfinyl)-1-(4-(2-oxopyridin-1(2H)-yl)phenyl)-1H-imidazol-4-yl)methyl)thiophene-2-carboxamide;
5-Chloro-N-((1-(4-(3-hydroxy-2-oxopyrazin-1(2H)-yl)phenyl)-1H-imidazol-4-yl)methyl)thiophene-2-carboxamide;
5-Chloro-N-((1-(4-(3-(2-hydroxyethoxy)-2-oxopyridin-1(2H)-yl)phenyl)-1H-imidazol-4-yl)methyl)thiophene-2-carboxamide;
5-Chloro-N-((1-(4-(4-ethyl-2,3-dioxopiperazin-1-yl)phenyl)-1H-imidazol-4-yl)methyl)thiophene-2-carboxamide;
N-((1-(4-(2-(Carbamoylimino)pyridin-1(2H)-yl)phenyl)-1H-imidazol-4-yl)methyl)-5-chlorothiophene-2-carboxamide;
5-Chloro-N-((2-methyl-1-(4-(2-oxopyridin-1(2H)-yl)phenyl)-1H-imidazol-4-yl)methyl)thiophene-2-carboxamide;
5-Chloro-N-((5-methyl-1-(4-(2-oxopyridin-1(2H)-yl)phenyl)-1H-imidazol-4-yl)methyl)thiophene-2-carboxamide;
5-Chloro-N-((1-(4-(5-fluoro-2-oxopyridin-1(2H)-yl)phenyl)-2-(methylsulfinyl)-1H-imidazol-4-yl)methyl)thiophene-2-carboxamide;

5-Chloro-N-((1-(4-(5-fluoro-2-oxopyridin-1(2H)-yl)phenyl)-2-(methylsulfonyl)-1H-imidazol-4-yl)methyl)thiophene-2-carboxamide;
5-Chloro-N-((1-(4-(3-fluoro-2-oxopyridin-1(2H)-yl)phenyl)-2-(methylsulfinyl)-1H-imidazol-4-yl)methyl)thiophene-2-carboxamide;
5-Chloro-N-((1-(4-(3-fluoro-2-oxopyridin-1(2H)-yl)phenyl)-2-(methylsulfonyl)-1H-imidazol-4-yl)methyl)thiophene-2-carboxamide;
5-Chloro-N-((1-(4-(5-fluoro-2-oxopyridin-1(2H)-yl)phenyl)-1H-imidazol-4-yl)methyl)thiophene-2-carboxamide;
5-Chloro-N-((1-(2-(2-methoxyethoxy)-4-(2-oxopyridin-1(2H)-yl)phenyl)-1H-imidazol-4-yl)methyl)thiophene-2-carboxamide;
(R)-5-Chloro-N-((1-(2-(2,3-dihydroxypropoxy)-4-(2-oxopyridin-1(2H)-yl)phenyl)-1H-imidazol-4-yl)methyl)thiophene-2-carboxamide;
(S)-5-Chloro-N-((1-(2-(2,3-dihydroxypropoxy)-4-(2-oxopyridin-1(2H)-yl)phenyl)-1H-imidazol-4-yl)methyl)thiophene-2-carboxamide;
5-Chloro-N-((1-(2-(2-hydroxypyridin-4-yl)-4-(2-oxopyridin-1(2H)-yl)phenyl)-1H-imidazol-4-yl)methyl)thiophene-2-carboxamide;
5-Chloro-N-((1-(2-(6-hydroxypyridin-3-yl)-4-(2-oxopyridin-1(2H)-yl)phenyl)-1H-imidazol-4-yl)methyl)thiophene-2-carboxamide;
N-((1-(2-(6-Aminopyridin-3-yl)-4-(2-oxopyridin-1(2H)-yl)phenyl)-1H-imidazol-4-yl)methyl)-5-chlorothiophene-2-carboxamide;
5-Chloro-N-((1-(4-(4-fluoro-2-oxopyridin-1(2H)-yl)phenyl)-1H-imidazol-4-yl)methyl)thiophene-2-carboxamide;
5-Chloro-N-((1-(4-(6-fluoro-2-oxopyridin-1(2H)-yl)phenyl)-1H-imidazol-4-yl)methyl)thiophene-2-carboxamide;
5-Chloro-N-((1-(4-(5-hydroxy-2-oxopyridin-1(2H)-yl)phenyl)-1H-imidazol-4-yl)methyl)thiophene-2-carboxamide; and
5-Chloro-N-((1-(4-(6-hydroxy-2-oxopyridin-1(2H)-yl)phenyl)-1H-imidazol-4-yl)methyl)thiophene-2-carboxamide.

All of the preferred, more preferred, and most preferred compounds listed above are selective inhibitors of Factor Xa.

b. Compositions

The present invention further provides compositions comprising one or more compounds of formula (I) or a pharmaceutically acceptable salt, ester or prodrug thereof, and a pharmaceutically acceptable carrier. It will be appreciated that the compounds of formula (I) in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of formula (I), similar to metabolically labile esters or carbamates, which are capable of producing the parent compounds of formula (I) in vivo, are within the scope of this invention.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Furthermore, the basic nitrogen-containing groups may be quaternized with agents like lower alkyl halides, such as methyl, ethyl, propyl and butyl chlorides, bromides and iodides; dialkyl sulfates, such as dimethyl, diethyl, dibutyl and diamyl sulfates, long chain halides, such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system, etc.), increase oral availability, increase solubility to allow administration by injection, alter metabolism and alter rate of excretion.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

Pharmaceutically acceptable carriers that may be used in these compositions include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, or long-acting. Still further, compounds can be administered in a local rather than systemic means, such as administration (e.g., injection) as a sustained release formulation.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multidose containers.

The pharmaceutical compositions of this invention may be in any orally acceptable dosage form, including capsules, tablets, aqueous suspensions or solutions. In the case of tablets for oral use, carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative, such as benzylalkonium chloride. Alternatively, for ophthalmic uses, the pharmaceutical compositions may be formulated in an ointment, such as petrolatum.

The pharmaceutical compositions of this invention may also be administered by nasal aerosol or inhalation. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

Any of the above dosage forms containing effective amounts are within the bounds of routine experimentation and within the scope of the invention. A therapeutically effective dose may vary depending upon the route of administration and dosage form. The preferred compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Besides those representative dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

c. Methods of Use

The invention provides methods of inhibiting or decreasing Factor Xa activity as well as treating or ameliorating a Factor Xa associated state, symptom, disorder or disease in a patient in need thereof (e.g., human or non-human). In one embodiment, the invention provides methods for preventing or treating a condition in a mammal characterized by undesired thrombosis comprising the step of administering to the mammal a therapeutically effective amount of a compound of the present invention. Such conditions include, but are not limited, to acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

"Treating" within the context of the invention means an alleviation of symptoms associated with a disorder or disease, or halt of further progression or worsening of those symptoms, or prevention or prophylaxis of the disease or disorder.

The term "mammal" includes organisms which express Factor Xa. Examples of mammals include mice, rats, cows, sheep, pigs, goats, horses, bears, monkeys, dogs, cats and, preferably, humans. Transgenic organisms which express Factor Xa are also included in this definition.

The inventive methods comprise administering an effective amount of a compound or composition described herein to a mammal or non-human animal. As used herein, "effective amount" of a compound or composition of the invention includes those amounts that antagonize or inhibit Factor Xa. An amount which antagonizes or inhibits Factor Xa is detectable, for example, by any assay capable of determining Factor Xa activity, including the one described below as an illustrative testing method. Effective amounts may also include those amounts which alleviate symptoms of a Factor Xa associated disorder treatable by inhibiting Factor Xa. Accordingly, "antagonists of Factor Xa" include compounds which interact with the Factor Xa and modulate, e.g., inhibit or decrease, the ability of a second compound, e.g., another Factor Xa ligand, to interact with the Factor Xa. The Factor Xa binding compounds are preferably antagonists of Factor Xa. The language "Factor Xa binding compound" (e.g., exhibits binding affinity to the receptor) includes those compounds which interact with Factor Xa resulting in modulation of the activity of Factor Xa. Factor Xa binding compounds may be identified using an in vitro (e.g., cell and non-cell based) or in vivo method. A description of an in vitro method is provided below.

The amount of compound present in the methods and compositions described herein should be sufficient to cause a detectable decrease in the severity of the disorder, as measured by any of the assays described in the examples. The amount of Factor Xa modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt, ester or prodrug thereof according to the formula (I), another therapeutic agent (e.g., methotrexate) or a pharmaceutically acceptable salt, ester or prodrug thereof, and a pharmaceutically acceptable excipient or carrier.

The invention comprises a compound having the formula (I), a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases (e.g., inflammatory, autoimmune, neurological, neurodegenerative, oncology and cardiovascular), such as RA, osteoarthritis, irritable bowel disease IBD, asthma, chronic obstructive pulmonary disease COPD and MS. The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

d. Kits

Still another aspect of this invention is to provide a kit comprising separate containers in a single package, wherein the inventive pharmaceutical compounds, compositions and/or salts thereof are used in combination with pharmaceutically acceptable carriers to treat states, disorders, symptoms and diseases where Factor Xa plays a role.

EXAMPLES

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods, which are well known in the art.

The compounds and/or intermediates were characterized by high performance liquid chromatography (HPLC) using a Waters Alliance chromatography system with a 2695 Separation Module (Milford, Mass.). The analytical columns were C-18 SpeedROD RP-18E Columns from Merck KGaA (Darmstadt, Germany). Alternately, characterization was performed using a Waters Unity (HPLC) system with Waters Acquity HPLC BEH C-18 2.1 mm×15 mm columns. A gradient elution was used, typically starting with 5% acetonitrile/95% water and progressing to 95% acetonitrile over a period of 5 minutes for the Alliance system and 1 minute for the Acquity system. All solvents contained 0.1% trifluoroacetic acid (TFA). Compounds were detected by ultraviolet light (UV) absorption at either 220 or 254 nm. HPLC solvents were from EMD Chemicals, Inc. (Gibbstown, N.J.). In some instances, purity was assessed by thin layer chromatography (TLC) using glass backed silica gel plates, such as, for example, EMD Silica Gel 60 2.5 cm×7.5 cm plates. TLC results were readily detected visually under ultraviolet light, or by employing well known iodine vapor and other various staining techniques.

Mass spectrometric analysis was performed on one of two Agilent 1100 series LCMS instruments with acetonitrile/water as the mobile phase. One system using TFA as the modifier and measures in positive ion mode and the other uses either formic acid or ammonium acetate and measures in both positive and negative ion modes.

Nuclear magnetic resonance (NMR) analysis was performed on some of the compounds with a Varian 400 MHz NMR (Palo Alto, Calif.). The spectral reference was either TMS or the known chemical shift of the solvent.

The purity of some of the invention compounds may be assessed by elemental analysis (Robertson Microlit, Madison N.J.).

Melting points may be determined on a Laboratory Devices MeI-Temp apparatus (Holliston, Mass.).

Preparative separations were carried out using either an Sq16x or an Sg100c chromatography system and prepackaged silica gel columns all purchased from Teledyne Isco, (Lincoln, Nebr.). Alternately, compounds and intermediates were purified by flash column chromatography using silica gel (230-400 mesh) packing material, or by HPLC using a C-18 reversed phase column. Typical solvents employed for the Isco systems and flash column chromatography were dichloromethane, methanol, ethyl acetate, hexane, acetone, aqueous hydroxyamine and triethyl amine. Typical solvents employed for the reverse phase HPLC were varying concentrations of acetonitrile and water with 0.1% trifluoroacetic acid.

The following abbreviations are used throughout the Examples:
μL=microliter
μM=micromolar
aq.=aqueous
BOP=benzotriazol-1-yloxytris(dimethylamino)-phosphonium hexafluorophosphate
$CaCl_2$=calcium chloride
$CH_2Cl_2$=dichloromethane
$CH_3CN$=acetonitrile
CuI=copper iodide
DIEA=diisopropyl ethyl amine
DMF=dimethyl formamide
DMSO=dimethyl sulfoxide
EtOAc=ethyl acetate
g=gram
h=hour
HATU=2-(1H-7-Azabenzotriazol-1-yl)-1,1,3,3-tetramethyl uronium hexafluorophosphate
HPLC=high pressure liquid chromatography
$IC_{50}$=The concentration of an inhibitor that is required for 50% inhibition of an enzyme in vitro
IV=intravenous
$K_2CO_3$=potassium carbonate
$K_3PO_4$=Potassium phosphate
kg=kilogram
M=molar
m/z=mass to charge ratio
mCPBA=m-chloroperoxybenzoic acid
MeOH=methanol
mg=milligram
MHz=Mega Hertz
min=minute
mL=milliliter
mm=millimeter
mM=millimolar
mmol=millimole
mOD/min=millioptical density units per minute
MP-=Macroporour triethylammonium methylpolystyrene carbonate (0.5% carbonate inorganic antistatic agent)
MS=Mass Spec
N=Normal
NaCl=sodium chloride
NaH=sodium hydride
$NaHCO_3$=sodium bicarbonate
$NaN_3$=sodium azide
NaSMe=sodium methylthiolate
$NaSO_4$=sodium sulfate
nBuOH=n-butanol
ng=nanogram
nm=nanometer
nM=nanomolar
$Pd(PPh_3)_4$=tetrakis-(triphenylphosphan)-palladium
PEG=polyethylene glycol
pM=picomolar
PO=oral
$PPh_3$ or $Ph_3P$=triphenyl phosphine
Ra—Ni=Rainey Nickel
SOCl2=thionyl chloride
TEA=triethylamine
TSC=trisodium citrate General Methods The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

Scheme I

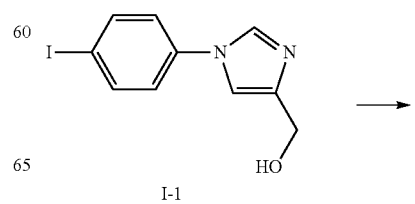

I-1

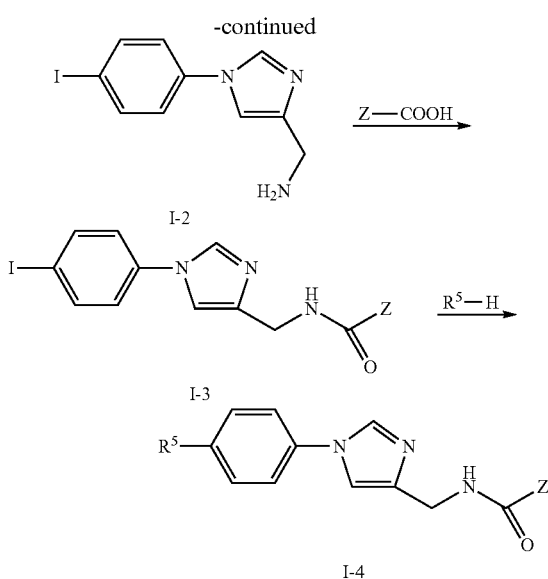

Scheme I represents the general synthetic method for preparing compounds having formula I-4. According to Scheme I, the alcohol I-1 is transformed to the amine I-2 via a three-step procedure: (1) halogenation such as with thionyl chloride, (2) displacement of the halide with an azide such as sodium azide, and (3) reduction of the azide to form the amine I-2 by catalytic hydrogenation. The amine I-2 is then coupled with the acid Z—COOH via conventional amide formation methods, such as using coupling reagents like BOP, to form compound I-3, wherein Z is as defined herein. Displacement of the iodo group of compound I-3 with the corresponding $R^5$ moiety, such as under basic conditions, such as with $K_2CO_3$, and in the presence of 8-hydroxyquinoline and CuI provides the desired compound I-4, wherein $R^5$ is as defined herein. Certain $R^5$ moieties of compound I-4 may undergo further modifications. For example, the thio group of Example 6 may be oxidized to form the corresponding sulfoxide and sulfone analogues. Compound I-1 may be obtained using either Scheme 1 or Scheme 2 below.

Scheme II

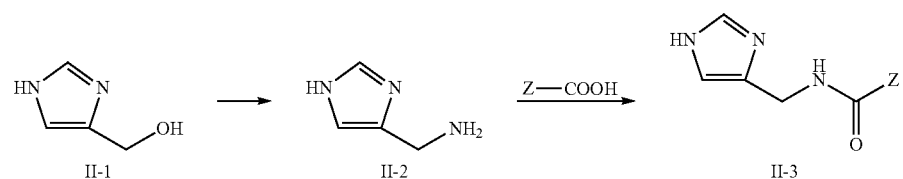

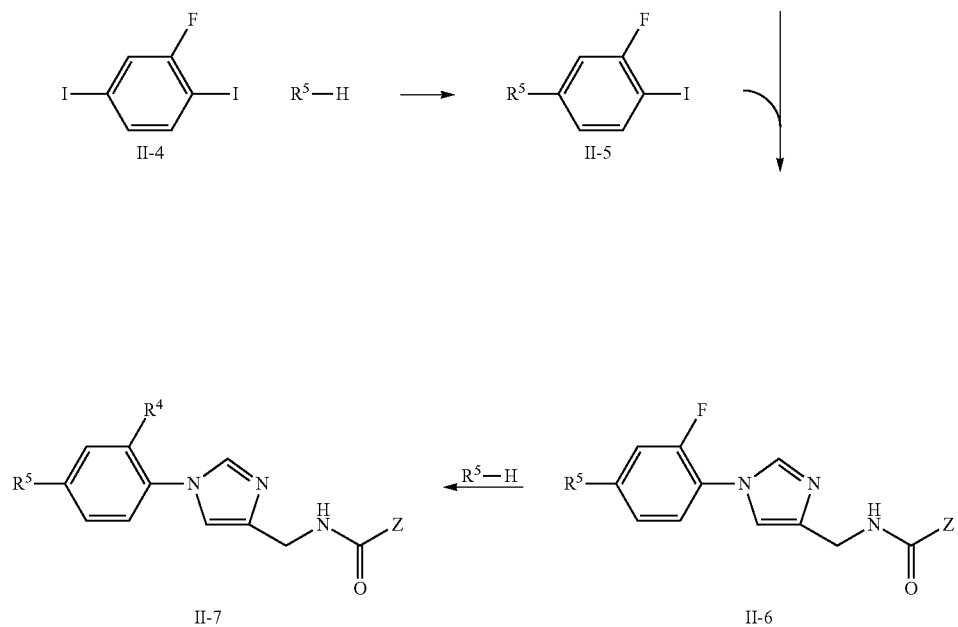

Compounds having formula II-7 may be prepared according to Scheme II. (1H-imidazol-4-yl)methanol II-1 is converted to (1H-imidazol-4-yl)methanamine II-2 via a three-step procedure and coupled with Z—COOH to form compound II-3 using conditions similar to that described above. Meanwhile, selective displacement of the 4-iodo group of 2-fluoro-1,4-diiodobenzene by $R^5$—H such as under basic conditions, such as with $K_2CO_3$, and in the presence of 8-hydroxyquinoline and CuI provides compound II-5. Subsequent displacement of the second iodo group with compound II-3 under similar conditions gives compound II-6. Compound II-6 may also be prepared through a linear route as exemplified by Scheme 4 below. Displacement of the fluoro group with $R^4$—H gives the desired product II-7, wherein $R^4$ is as defined herein.

Example 1

5-Chloro-N-((1-(4-(2-oxopyridin-1(2H)-yl)phenyl)-1H-imidazol-4-yl)methyl)thiophene-2-carboxamide (10)

Scheme 1 represents a synthetic method for the synthesis of compound 10. Scheme 2 represents an alternative method for the synthesis of compound I-1.

SCHEME 1

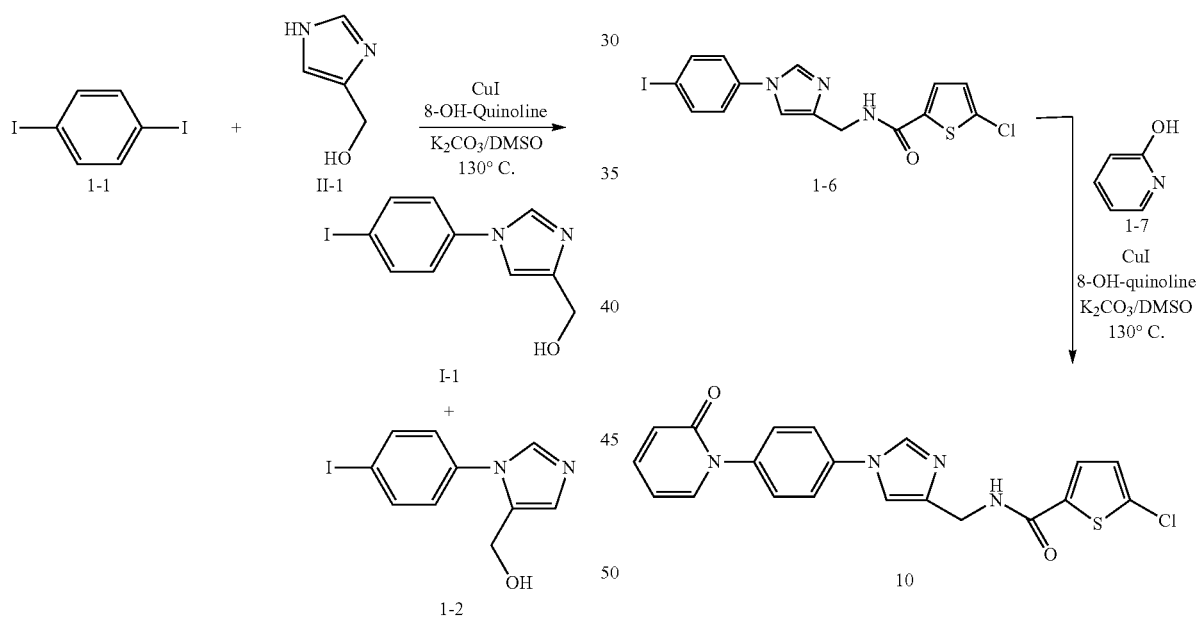

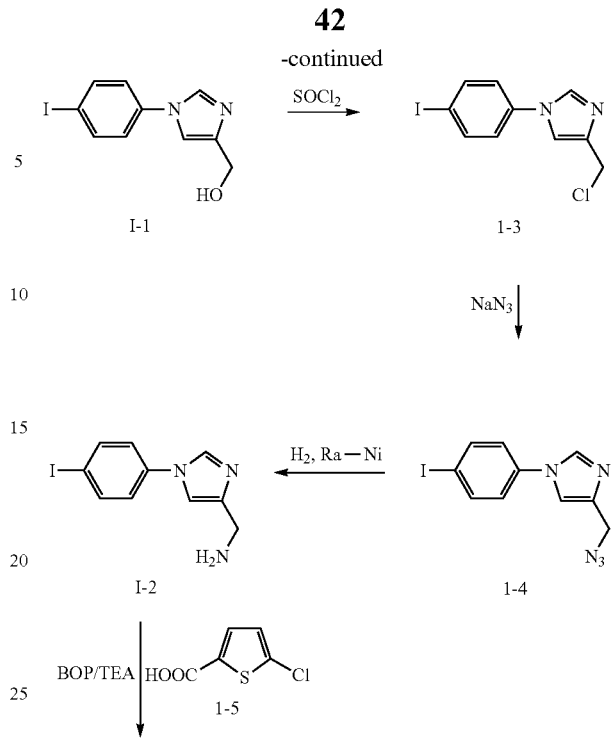

SCHEME 2

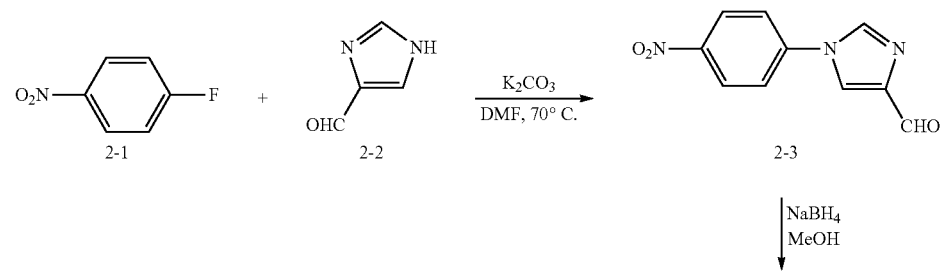

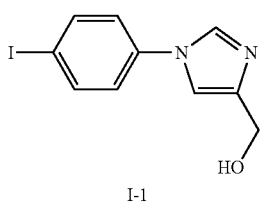

I-1

-continued
1) H₂/Pd—C
2) NaNO₂/HCl
3) NaI
←

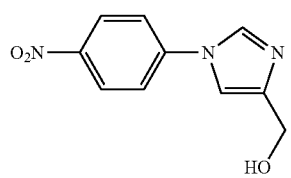

2-4

Step 1:

A mixture of 1,4-diiodobenzene 1-1 (4.00 g, 12.1 mmol), 4-(hydroxymethyl)imidazole II-1 (1.20 g, 12.2 mmol), 8-hydroxyquinoline (0.176 g, 1.21 mmol) and K₂CO₃ (1.69 g, 12.2 mmol) in DMSO (12 mL) was degassed before being charged with CuI (0.230 g, 1.21 mmol). The mixture in a sealed tube was heated at 130° C. overnight. Water and EtOAc were added. The mixture was filtered. The organic layer was separated, then applied to a silica gel column, which was eluted with 0-5% MeOH in CH₂Cl₂ to give 4-hydroxymethyl 1-(4-iodophenyl)imidazole I-1 (0.810 g). MS 301.2 (M+H).

Step 2:

The compound 4-hydroxymethyl 1-(4-iodophenyl)imidazole I-1 (0.810 g, 2.70 mmol) was dissolved in SOCl₂ (6 mL). The solution was stirred at room temperature for 15 min. It was then concentrated in vacuo. The residue was partitioned between EtOAc and 5% aq. NaHCO₃. The organic layer was separated, dried over Na₂SO₄, concentrated in vacuo to give 4-chloromethyl 1-(4-iodophenyl)imidazole 1-3 as a solid (0.780 g). MS 318.9 and 320.9 (M+H, Cl pattern).

Step 3:

The compound 4-chloromethyl 1-(4-iodophenyl)imidazole 1-3 (0.780 g, 2.45 mmol) was dissolved in DMF (10 mL). To the solution, NaN₃ (0.520 g, 8.00 mmol) was added. After being stirred at room temperature overnight, water and EtOAc were added. The organic layer was separated, dried over Na₂SO₄, concentrated in vacuo to give 4-azidomethyl 1-(4-iodophenyl)imidazole 1-4 as a solid (0.725 g). MS 326.0 (M+H)

Step 4:

A solution of 4-azidomethyl 1-(4-iodophenyl)imidazole 1-4 (0.725 g, 2.23 mmol) over Ra—Ni (50% aq. slurry, 300 mg) in MeOH (12 mL) was hydrogenated under balloon H₂ for 3 h. The mixture was filtrated through CELITE. The filtrate was concentrated in vacuo to give 4-aminomethyl 1-(4-iodophenyl)imidazole 1-2 as a solid (0.603 g). MS 300.0 (M+H)

Step 5:

To a mixture of 5-chlorothiophene-2-carboxylic acid 1-5 (0.346 g, 2.13 mmol), 4-aminomethyl 1-(4-iodophenyl)imidazole 1-2 prepared above (0.578 g, 1.93 mmol) and TEA (0.670 mL, 4.82 mmol) in DMF (10 mL), BOP (1.03 g, 2.33 mmol) was added. The mixture was then stirred at room temperature overnight. Water and EtOAc were added. The organic layer was separated, washed with 5% NaHCO₃, dried over Na₂SO₄, concentrated in vacuo to give 5-chloro-N-((1-(4-iodophenyl)-1H-imidazol-4-yl)methyl)thiophene-2-carboxamide 1-6 as a solid (0.832 g), which was found to be pure enough for next reaction. MS 443.9 and 445.9 (M+H, Cl pattern).

Step 6:

A mixture of 5-chloro-N-((1-(4-iodophenyl)-1H-imidazol-4-yl)methyl)thiophene-2-carboxamide 1-6 prepared above (0.270 g, 0.609 mmol), 2-hydroxypyridine 1-7 (0.115 g, 1.21 mmol), 8-hydroxyquinoline (0.041 g, 0.283 mmol) and K₂CO₃ (0.333 g, 2.41 mmol) in DMSO (2 mL) was degassed before being charged with CuI (0.058 g, 0.305 mmol). The mixture in a sealed tube was heated at 130° C. overnight. The mixture was then purified by HPLC to give the title compound 10 (0.080 g). MS 411.0 and 413.0 (M+H, Cl pattern); ¹H NMR (DMSO-d₆, 400 MHz) δ 9.27 (m, 2H), 8.08 (s, 1H), 7.87 (d, 2H), 7.69 (d, 1H), 7.65 (m, 3H), 7.51 (m, 1H), 7.19 (d, 1H), 6.49 (d, 1H), 6.34 (dd, 1H), 4.52 (d, 2H).

Example 2

5-Chloro-N-((1-(4-(3-oxomorpholino)phenyl)-1H-imidazol-4-yl)methyl)thiophene-2-carboxamide (11)

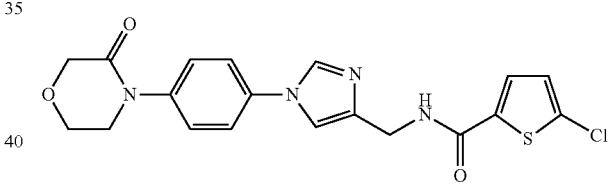

NaH (60%, 3.2 g, 80 mmol) in a flask was washed with hexane. To the flask, cooled in an ice-bath, a solution of ethanolamine (4.4 mL, 73 mmol) in dioxane (40 mL) was added. The mixture was heated at reflux for 10 min until no H₂ gas evolved. The thick slurry was then cooled in an ice-bath, and a solution of ethyl chloroacetate (8.9 g, 73 mmol) in dioxane (15 mL) was added. The reaction mixture was heated at reflux for 1 h. It was then filtered. The filtrate was concentrated in vacuo to give an oil, which was purified by a short silica gel column, eluted with EtOAc/MeOH (95/5) to give 3-morpholinone as a white solid (1.9 g).

A mixture of 5-chloro-N-((1-(4-iodophenyl)-1H-imidazol-4-yl)methyl)thiophene-2-carboxamide 1-6 prepared in Example 1 (33 mg, 0.074 mmol), 3-morpholinone prepared above (22 mg, 0.218 mmol), 8-hydroxyquinoline (7 mg, 0.048 mmol) and K₂CO₃ (30 mg, 0.217 mmol) in DMSO (0.5 mL) was degassed before being charged with CuI (14 mg, 0.073 mmol). The mixture in a sealed tube was heated at 130°

C. overnight. The mixture was then purified by HPLC to give the title compound (3 mg). MS 417.0 and 419.0 (M+H, Cl pattern).

Example 3

5-Chloro-N-((1-(4-(2-oxopyrazin-1(2H)-yl)phenyl)-1H-imidazol-4-yl)methyl)thiophene-2-carboxamide (12)

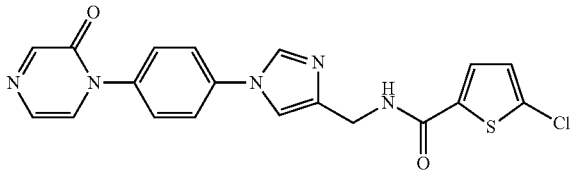 [SMILES: O=C(NCc1cn(-c2ccc(-n3ccncc3=O)cc2)cn1)c1ccc(Cl)s1]

To a solution of glycinamide hydrochloride (1.10 g, 10.0 mmol) in 5 N NaOH (6 mL) at room temperature, glyoxal (40% in $H_2O$, 1.5 mL, 13.1 mmol) was added. The solution was stirred at room temperature overnight. The product was extracted from the aqueous solution with nBuOH, and the nBuOH extract was concentrated in vacuo to give 2-hydroxypyrazine as a white solid (0.20 g).

A mixture of 5-chloro-N-((1-(4-iodophenyl)-1H-imidazol-4-yl)methyl)thiophene-2-carboxamide 1-6 prepared in Example 1 (100 mg, 0.23 mmol), 2-hydroxypyrazine prepared above (43 mg, 0.45 mmol), 8-hydroxyquinoline (15 mg, 0.10 mmol) and $K_2CO_3$ (123 mg, 0.89 mmol) in DMSO (1 mL) was degassed before being charged with CuI (21 mg, 0.11 mmol). The mixture in a sealed tube was heated at 130° C. overnight. The mixture was then purified by HPLC to give the title compound (15 mg). MS 412.0 and 414.0 (M+H, Cl pattern).

Example 4

5-Chloro-N-((1-(4-(6-oxopyridazin-1(6H)-yl)phenyl)-1H-imidazol-4-yl)methyl)thiophene-2-carboxamide (13)

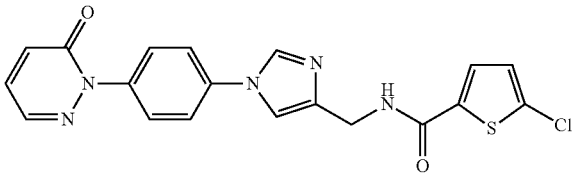 [SMILES: O=C(NCc1cn(-c2ccc(-n3ncccc3=O)cc2)cn1)c1ccc(Cl)s1]

A mixture of 5-chloro-N-((1-(4-iodophenyl)-1H-imidazol-4-yl)methyl)thiophene-2-carboxamide 1-6 prepared in Example 1 (100 mg, 0.23 mmol), 3-hydroxypyridazine (43 mg, 0.45 mmol), 8-hydroxyquinoline (15 mg, 0.10 mmol) and $K_2CO_3$ (123 mg, 0.89 mmol) in DMSO (1 mL) was degassed before being charged with CuI (19 mg, 0.10 mmol). The mixture in a sealed tube was heated at 130° C. overnight.

The mixture was then purified by HPLC to give the title compound (15 mg). MS 412.0 and 414.0 (M+H, Cl pattern).

Example 5

5-chloro-N-((1-(4-(6-methyl-2-oxopyridin-1(2H)-yl)phenyl)-1H-imidazol-4-yl)methyl)thiophene-2-carboxamide (14)

A mixture of 5-chloro-N-((1-(4-iodophenyl)-1H-imidazol-4-yl)methyl)thiophene-2-carboxamide 1-6 (100 mg, 0.22 mmol), 2-hydroxy-6-methylpyridine (60 mg, 0.55 mmol), 8-hydroxyquinoline (20 mg, 0.14 mmol) and $K_2CO_3$ (140 mg, 1.01 mmol) in DMSO (3 mL) was degassed with Ar before being charged with CuI (28 mg, 0.15 mmol). The mixture in a sealed tube was heated at 130° C. overnight. The mixture was then purified by HPLC to give the titled compound (4 mg). MS 425.1 and 427.1 (M+H, Cl pattern).

Example 6

5-Chloro-N-((1-(4-(3-oxothiomorpholino)phenyl)-1H-imidazol-4-yl)methyl)thiophene-2-carboxamide (15)

A mixture of 5-chloro-N-((1-(4-iodophenyl)-1H-imidazol-4-yl)methyl)thiophene-2-carboxamide 1-6 prepared in Example 1 (230 mg, 0.518 mmol), 3-thiomorpholinone (121 mg, 1.03 mmol), 1,2-trans-diaminocyclohexane (26 μL, 0.21 mmol) and $K_3PO_4$ (220 mg, 1.04 mmol) in dioxane (2 mL) was degassed with Ar before being charged with CuI (40 mg, 0.21 mmol). The mixture in a sealed tube was heated at 110° C. overnight. It was then purified by HPLC to give the title compound (58 mg). MS 433.1 and 435.0 (M+H, Cl pattern).

Example 7

5-Chloro-N-((1-(4-(1,1-dioxo-3-oxothiomorpholino)phenyl)-1H-imidazol-4-yl)methyl)thiophene-2-carboxamide (16) and 5-Chloro-N-((1-(4-(1,3-dioxothiomorpholino)phenyl)-1H-imidazol-4-yl)methyl)thiophene-2-carboxamide (17)

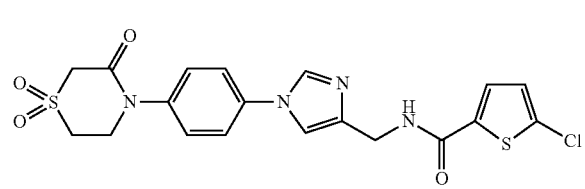

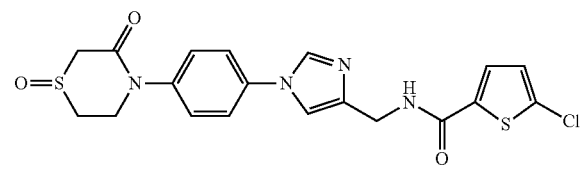

To a solution of 5-chloro-N-((1-(4-(3-oxothiomorpholino)phenyl)-1H-imidazol-4-yl)methyl)thiophene-2-carboxamide prepared in Example 6 (56 mg, 0.13 mmol) in acetone (3 mL) at room temperature, mCPBA (38 mg, 70-77%, 0.15 mmol) was added. It was stirred at room temperature for 1 h. HPLC showed formation of the sulfone and sulfoxide in a ratio of 2 to 1. The solution was concentrated in vacuo, and the residue was purified by HPLC to give the sulfone (6 mg) and the sulfoxide (3 mg). MS 465.0 and 467.0 (M+H, Cl pattern) for the sulfone and 449.1 and 451.0 (M+H, Cl pattern) for the sulfoxide.

Example 8

5-Chloro-N-((1-(4-(2-oxo-tetrahydropyrimidin-1(2H)-yl)phenyl)-1H-imidazol-4-yl)methyl)thiophene-2-carboxamide (18)

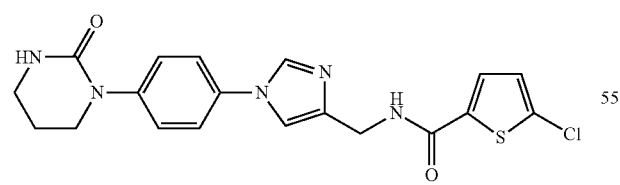

A mixture of 5-chloro-N-((1-(4-iodophenyl)-1H-imidazol-4-yl)methyl)thiophene-2-carboxamide 1-6 prepared in Example 1 (80 mg, 0.18 mmol), tetrahydro-2-pyrimidinone (54 mg, 0.54 mmol), 1,2-trans-diaminocyclohexane (13 μL, 0.11 mmol) and $K_3PO_4$ (100 mg, 0.47 mmol) in dioxane (1 mL) was degassed with Ar before being charged with CuI (20 mg, 0.11 mmol). The mixture in a sealed tube was heated at 110° C. overnight. It was then purified by HPLC to give the title compound (4 mg). MS 416.1 and 418.1 (M+H, Cl pattern).

Example 9

5-Chloro-N-((1-(4-(2-oxoimidazolidin-1-yl)phenyl)-1H-imidazol-4-yl)methyl)thiophene-2-carboxamide (19)

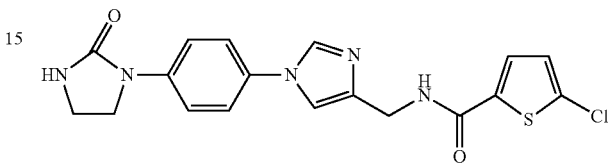

A mixture of 5-chloro-N-((1-(4-iodophenyl)-1H-imidazol-4-yl)methyl)thiophene-2-carboxamide 1-6 prepared in Example 1 (80 mg, 0.18 mmol), ethyleneurea (40 mg, 0.47 mmol), 1,2-trans-diaminocyclohexane (15 μL, 0.12 mmol) and $K_2CO_3$ (100 mg, 0.72 mmol) in DMSO (1 mL) was degassed with Ar before being charged with CuI (20 mg, 0.11 mmol). The mixture in a sealed tube was heated at 110° C. overnight. It was then purified by HPLC to give the title compound (5 mg). MS 402.1 and 404.1 (M+H, Cl pattern).

Example 10

5-Chloro-N-((1-(4-(2,5-dioxopiperazin-1-yl)phenyl)-1H-imidazol-4-yl)methyl)thiophene-2-carboxamide (20)

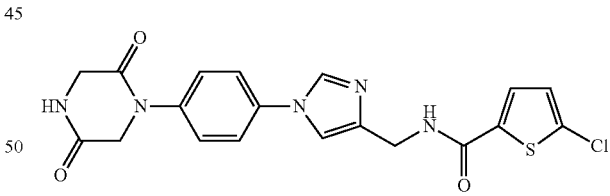

A mixture of 5-chloro-N-((1-(4-iodophenyl)-1H-imidazol-4-yl)methyl)thiophene-2-carboxamide 1-6 prepared in Example 1 (80 mg, 0.18 mmol), glycine anhydride (40 mg, 0.35 mmol), 1,2-trans-diaminocyclohexane (30 μL, 0.24 mmol) and $K_2CO_3$ (100 mg, 0.72 mmol) in DMSO (1 mL) was degassed with Ar before being charged with CuI (20 mg, 0.11 mmol). The mixture in a sealed tube was heated at 110° C. overnight. It was then purified by HPLC to give the title compound (10 mg). MS 430.1 and 432.1 (M+H, Cl pattern).

Example 11
5-Chloro-N-((1-(2-fluoro-4-(2-oxopyridin-1(2H)-yl)phenyl)-1H-imidazol-4-yl)methyl)thiophene-2-carboxamide (21)
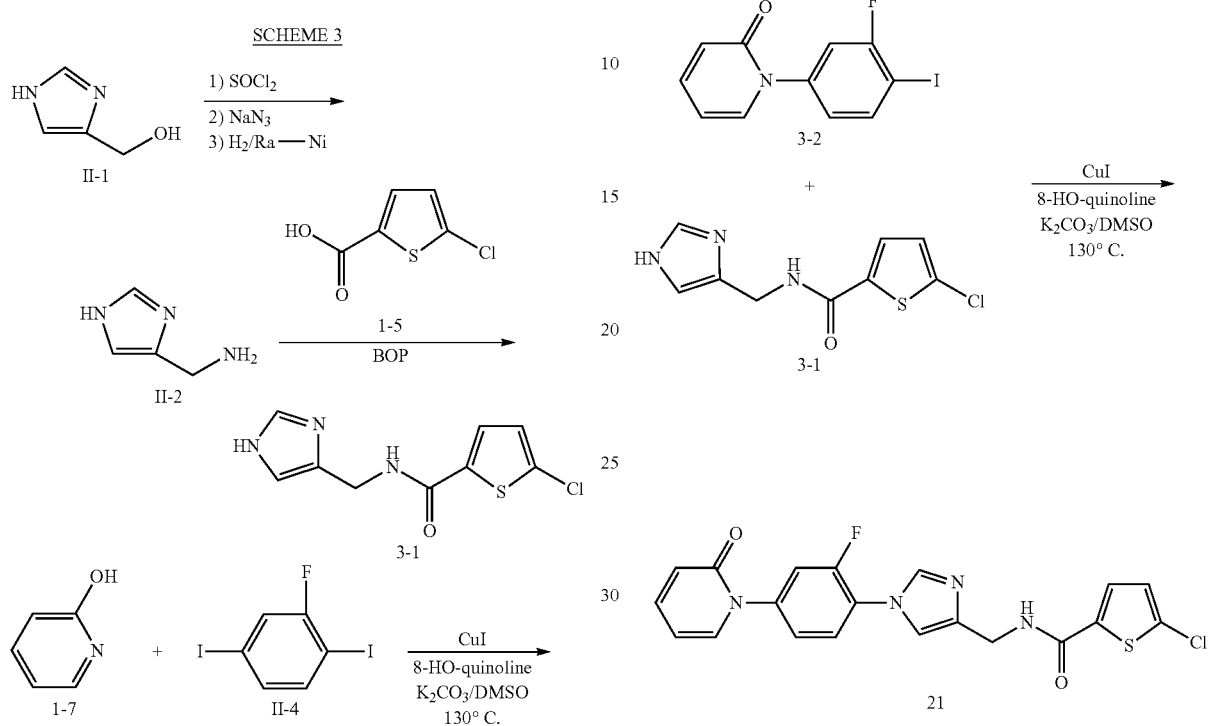
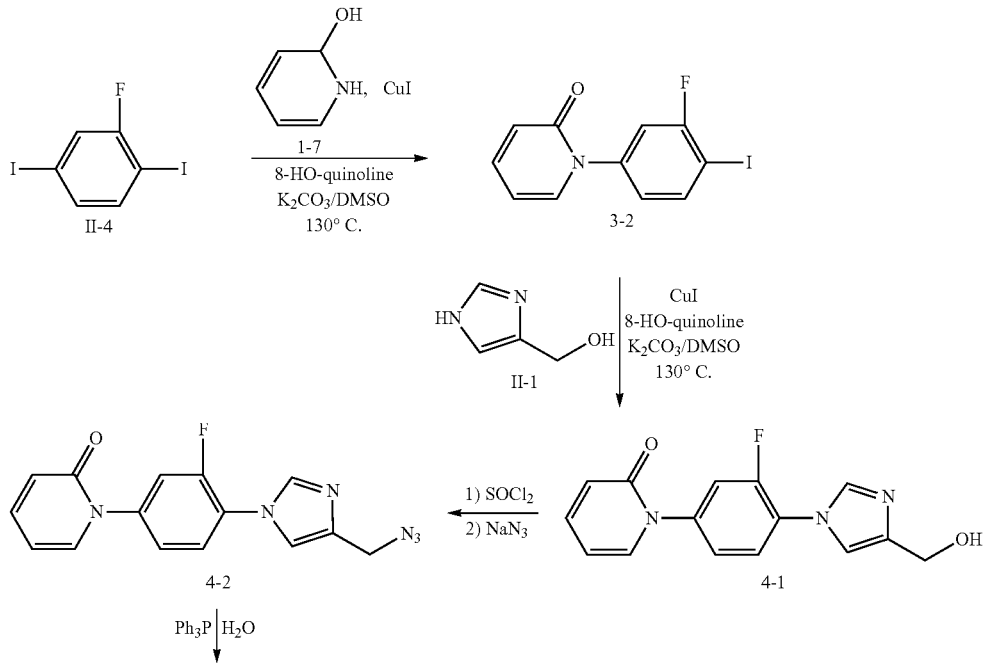

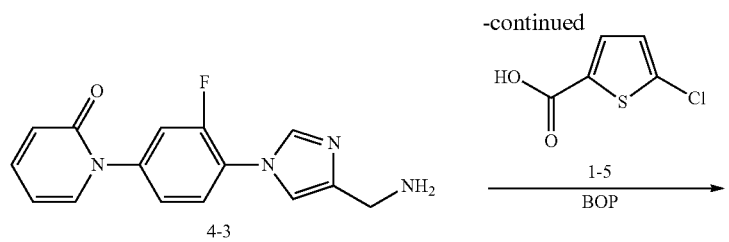
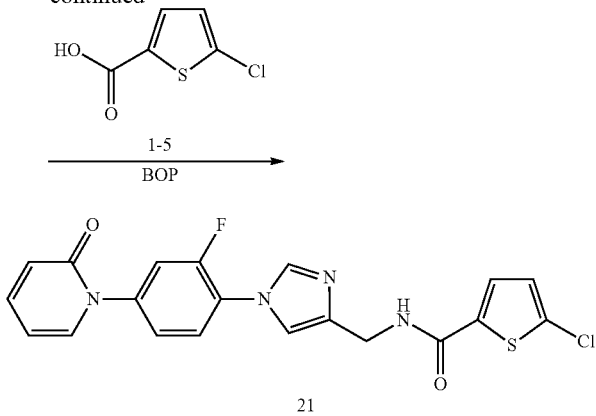

A mixture of 2,5-diiodofluorobenzene II-4 (2.00 g, 5.75 mmol), 2-hydroxypyridine 1-7 (0.546 g, 5.75 mmol), 8-hydroxyquinoline (0.083 g, 0.57 mmol) and K$_2$CO$_3$ (1.00 g, 7.25 mmol) in DMSO (10 mL) was degassed before being charged with CuI (0.109 g, 0.57 mmol). The mixture in a sealed tube was heated at 130° C. overnight. Water and EtOAc were added. The mixture was filtered. The organic layer was separated, then applied to a silica gel column, which was eluted with 0-70% EtOAc in hexane to give 1-iodo-2-fluoro-4-(2-oxopyridin-1(2H)-yl)benzene 3-2 (0.820 g). MS 315.8 (M+H).

To a suspension of 4-hydroxymethylimidazole II-1 (1.09 g, 11.1 mmol) in CH$_3$CN (12 mL), SOCl$_2$ (5 mL) was added. After being stirred at room temperature for 30 min, the suspension became clear. After stirring for additional 2 h, the solution was concentrated in vacuo to give a solid, which was then dissolved in DMF (15 mL). To the solution, NaN$_3$ (2.16 g, 33.2 mmol) was added. After the mixture was stirred at room temperature overnight, water and EtOAc were added, then 5% aq. NaHCO$_3$ was also added. The organic layer was separated, dried over Na$_2$SO$_4$, concentrated in vacuo to give 4-azidomethylimidazole as a solid (0.759 g). MS 124.1 (M+H).

A mixture of 4-azidomethylimidazole prepared above (0.759 g, 6.17 mmol) and Ra—Ni (50% slurry in H$_2$O, 900 mg) in MeOH (15 mL) was hydrogenated under H$_2$ balloon overnight. The mixture was then filtered through CELITE. The filtrate was concentrated in vacuo to give 4-aminomethylimidazole II-2 (0.604 g).

To a solution of 5-chlorothiophene-2-carboxylic acid 1-5 (1.10 g, 6.76 mmol) and TEA (2.0 mL, 14.4 mmol) in DMF (12 mL), BOP (3.30 g, 7.45 mmol) was added. After being mixed for 5 min, the solution was added to the compound 4-aminomethylimidazole II-2 prepared above (0.604 g, 6.22 mmol) in a round bottom flask. The mixture was then stirred at room temperature overnight. It was purified by HPLC to give 5-chloro-N-((1H-imidazol-4-yl)methyl)thiophene-2-carboxamide 3-1 (1.52 g). MS 242.0 and 244.0 (M+H, Cl pattern).

A mixture of 5-chloro-N-((1H-imidazol-4-yl)methyl)thiophene-2-carboxamide 3-1 prepared above (0.940 g, 2.64 mmol), 1-iodo-2-fluoro-4-(2-oxopyridin-1(2H)-yl)benzene 3-2 prepared above (0.820 g, 2.60 mmol), 8-hydroxyquinoline (0.066 g, 0.45 mmol) and K$_2$CO$_3$ (0.630 g, 4.56 mmol) in DMSO (8 mL) was degassed with Ar before being charged with CuI (0.090 g, 0.47 mmol). The mixture in a sealed tube was heated at 130° C. overnight. It was then purified by HPLC to give the title compound (0.480 g). MS 429.0 and 431.0 (M+H, Cl pattern).

Alternatively as shown in Scheme 4, 1-iodo-2-fluoro-4-(2-oxopyridin-1(2H)-yl)benzene 3-2 prepared as above, is treated with 4-hydroxymethylimidazole II-1 in the presence of 8-hydroxyquinoline, and K$_2$CO$_3$ in DMSO. The resulting mixture is degassed before being charged with CuI to give 4-hydroxymethyl-(2-fluoro-4-(2-oxopyridin-1(2H)-yl)phenyl)imidazole 4-1. The compound 4-1 is treated with thionyl chloride to give 4-chloromethyl-(2-fluoro-4-(2-oxopyridin-1 (2H)-yl)phenyl)imidazole which is then treated with NaN$_3$ to result in 4-azidomethyl-(2-fluoro-4-(2-oxopyridin-1(2H)-yl) phenyl)imidazole 4-2. The azide 4-2 is reduced with Ph$_3$P to give 4-aminomethyl-(2-fluoro-4-(2-oxopyridin-1(2H)-yl) phenyl)imidazole 4-3. The compound 4-3 is then treated with 5-chlorothiophene-2-carboxylic acid 1-5 to give the title compound 21.

Example 12

5-Chloro-N-((1-(2-(methylsulfonyl)-4-(2-oxopyridin-1(2H)-yl)phenyl)-1H-imidazol-4-yl)methyl) thiophene-2-carboxamide (22) and 5-chloro-N-((1-(2-(methylsulfinyl)-4-(2-oxopyridin-1(2H)-yl) phenyl)-1H-imidazol-4-yl)methyl)thiophene-2-carboxamide (23)

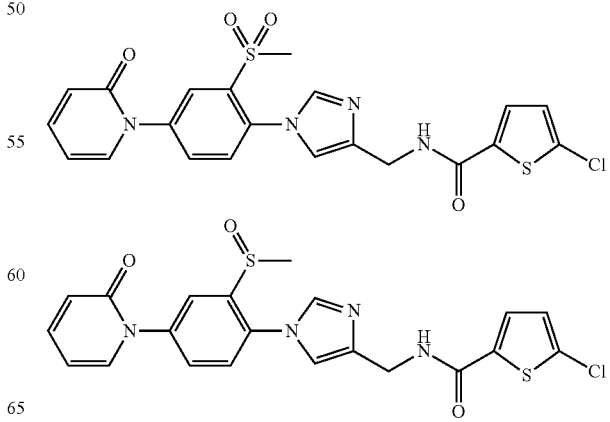

A solution of 5-chloro-N-((1-(2-fluoro-4-(2-oxopyridin-1(2H)-yl)phenyl)-1H-imidazol-4-yl)methyl)thiophene-2-carboxamide 21 prepared in Example 11 (96 mg, 0.22 mmol) and NaSMe (68 mg, 0.97 mmol) in DMSO (2 mL) was heated at 80° C. for 1 h. The mixture was purified by HPLC to give 5-chloro-N-((1-(2-(methylthio)-4-(2-oxopyridin-1(2H)-yl)phenyl)-1H-imidazol-4-yl)methyl)thiophene-2-carboxamide (16 mg). MS 457.0 and 459.0 (M+H, Cl pattern)

To a solution of 5-chloro-N-((1-(2-(methylthio)-4-(2-oxopyridin-1 (2H)-yl)phenyl)-1H-imidazol-4-yl)methyl) thiophene-2-carboxamide prepared above (16 mg, 0.035 mmol) in acetone (1 mL), mCPBA (70%, 12 mg, 0.049 mmol) was added. After being stirred at room temperature for 30 min, the mixture was purified by HPLC to give the sulfoxide (5 mg) and sulfone (3 mg). MS 473.0 and 475.0 (M+H, Cl pattern) for sulfoxide and 489.0 and 491.0 (M+H, Cl pattern) for sulfone.

Example 13

5-Chloro-N-((1-(4-(2-oxopyridin-1(2H)-yl)-2-thiomorpholinophenyl)-1H-imidazol-4-yl)methyl) thiophene-2-carboxamide (24)

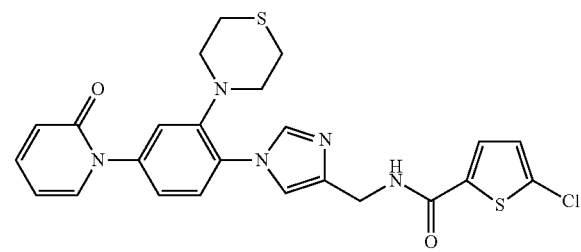 [SMILES: O=C(NCc1cn(-c2ccc(-n3ccccc3=O)cc2N2CCSCC2)cn1)c1ccc(Cl)s1]

A solution of 5-chloro-N-((1-(2-fluoro-4-(2-oxopyridin-1(2H)-yl)phenyl)-1H-imidazol-4-yl)methyl)thiophene-2-carboxamide prepared in Example 11 (70 mg, 0.16 mmol) and thiomorpholine (1 mL) in DMSO (1 mL) was heated at 150° C. for 3 days. The mixture was purified by HPLC to give the title compound (25 mg). MS 512.0 and 514.0 (M+H, Cl pattern).

Example 14

5-Chloro-N-((1-(4-(2-oxopyridin-1(2H)-yl)-2-(1,1-dioxo-thiomorpholin-4-yl)phenyl)-1H-imidazol-4-yl) methyl)thiophene-2-carboxamide (25)

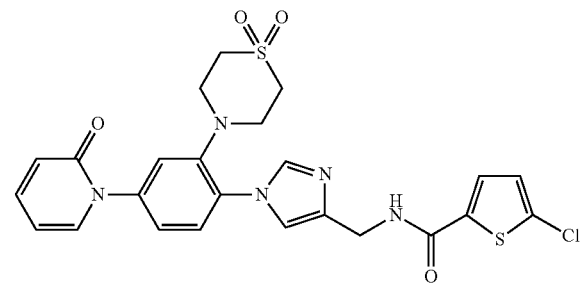 [SMILES: O=C(NCc1cn(-c2ccc(-n3ccccc3=O)cc2N2CCS(=O)(=O)CC2)cn1)c1ccc(Cl)s1]

To a solution of 5-chloro-N-((1-(4-(2-oxopyridin-1(2H)-yl)-2-thiomorpholinophenyl)-1H-imidazol-4-yl)methyl) thiophene-2-carboxamide prepared in Example 13 (22 mg, 0.043 mmol) in acetone (2 mL), mCPBA (70%, 32 mg, 0.13 mmol) was added. After being stirred at room temperature for 2 h, the mixture was purified by HPLC to give the title compound (8 mg). MS 544.1 and 546.1 (M+H, Cl pattern).

Example 15

5-Chloro-N-((1-(2-(3-oxopiperazin-1-yl)-4-(2-oxopyridin-1(2H)-yl)phenyl)-1H-imidazol-4-yl)methyl)thiophene-2-carboxamide (26)

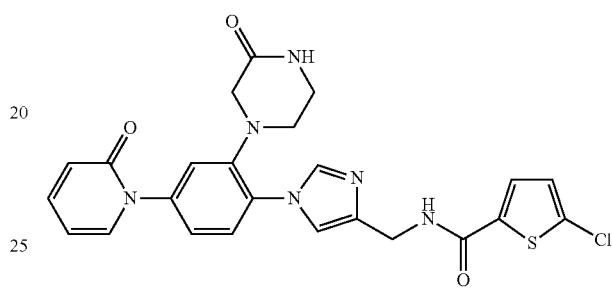

A solution of 5-chloro-N-((1-(2-fluoro-4-(2-oxopyridin-1(2H)-yl)phenyl)-1H-imidazol-4-yl)methyl)thiophene-2-carboxamide prepared in Example 11 (70 mg, 0.16 mmol) and 2-oxopiperazine (565 mg, 5.65 mmol) in DMSO (1 mL) was heated at 150° C. for 2 days. The mixture was purified by HPLC to give the title compound (14 mg). MS 509.0 and 511.0 (M+H, Cl pattern).

Example 16

5-Chloro-N-((1-(2-(2-hydroxyethylamino)-4-(2-oxopyridin-1(2H)-yl)phenyl)-1H-imidazol-4-yl)methyl)thiophene-2-carboxamide (27)

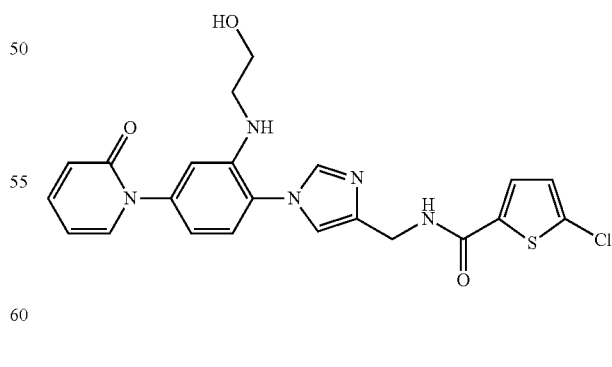

A solution of 5-chloro-N-((1-(2-fluoro-4-(2-oxopyridin-1(2H)-yl)phenyl)-1H-imidazol-4-yl)methyl)thiophene-2-carboxamide prepared in Example 11 (75 mg, 0.17 mmol) and ethanolamine (1.5 mL) in DMSO (1 mL) in a sealed tube was heated at 150° C. overnight. The mixture was purified by HPLC to give the title compound (13 mg). MS 470.0 and 472.0 (M+H, Cl pattern).

Example 17

5-Chloro-N-((1-(2-hydroxy-4-(2-oxopyridin-1(2H)-yl)phenyl)-1H-imidazol-4-yl)methyl)thiophene-2-carboxamide (28)

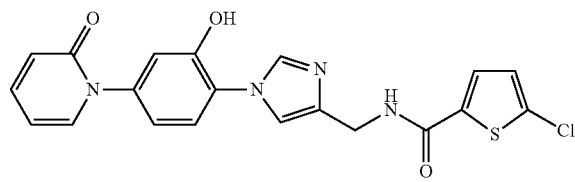 [SMILES: O=C(NCc1cn(-c2ccc(-n3ccccc3=O)cc2O)cn1)c1ccc(Cl)s1]

A solution of 5-chloro-N-((1-(2-fluoro-4-(2-oxopyridin-1(2H)-yl)phenyl)-1H-imidazol-4-yl)methyl)thiophene-2-carboxamide prepared in Example 11 (80 mg, 0.19 mmol) and 5 N aq. NaOH (0.5 mL, 2.5 mmol) in DMSO (2 mL) in a sealed tube was heated at 130° C. overnight. The mixture was purified by HPLC to give the title compound (5 mg). MS 427.0 and 429.0 (M+H, Cl pattern).

Example 18

5-Chloro-N-((1-(2-methoxycarbonyl-4-(2-oxopyridin-1(2H)-yl)phenyl)-1H-imidazol-4-yl)methyl)thiophene-2-carboxamide (29)

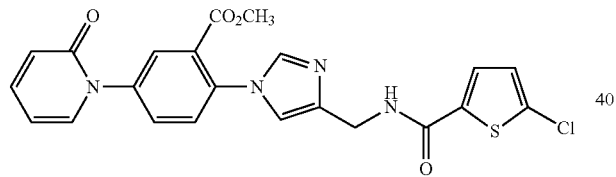

To a solution of 2,5-diiodobenzoic acid (1.00 g, 2.67 mmol) in anhydrous MeOH (15 mL) cooled in an ice-bath, SOCl$_2$ (0.50 mL, 6.85 mmol) was cautiously added (exothermal reaction). After the addition, the solution was heated at reflux overnight. It was then concentrated in vacuo to give methyl 2,5-diiodobenzoate (1.04 g).

A mixture of methyl 2,5-diiodobenzoate prepared above (1.04 g, 2.67 mmol), 2-hydroxypyridine 1-7 (0.254 g, 2.67 mmol), 8-hydroxyquinoline (0.077 g, 0.53 mmol) and K$_3$PO$_4$ (1.13 g, 5.33 mmol) in dioxane (8 mL) was degassed with Ar before being charged with CuI (0.101 g, 0.53 mmol). The mixture in a sealed tube was heated at 130° C. overnight. It was then purified by HPLC to give 2-iodo-5-(2-oxopyridin-1(2H)-yl)benzoic acid (0.220 g). MS 342.0 (M+H).

A mixture of 2-iodo-5-(2-oxopyridin-1(2H)-yl)benzoic acid prepared above (220 mg, 0.65 mmol), 4-hydroxymethylimidazole II-1 (126 mg, 1.29 mmol), 8-hydroxyquinoline (19 mg, 0.13 mmol) and K$_2$CO$_3$ (290 mg, 2.10 mmol) in DMSO (2 mL) was degassed with Ar before being charged with CuI (25 mg, 0.13 mmol). The mixture in a sealed tube was heated at 130° C. overnight. It was then purified by HPLC to give 2-(4-(hydroxymethyl)-1H-imidazol-1-yl)-5-(2-oxopyridin-1(2H)-yl)benzoic acid (92 mg). MS 312.1 (M+H).

To a solution of 2-(4-(hydroxymethyl)-1H-imidazol-1-yl)-5-(2-oxopyridin-1(2H)-yl)benzoic acid prepared above (92 mg, 0.30 mmol) in MeOH (4 mL) and dioxane (2 mL) at room temperature, (trimethylsilyl)diazomethane (2 M in ether, 0.30 mL, 0.60 mmol) was added. After the mixture was stirred at room temperature overnight, more (trimethylsilyl)diazomethane (2 M in ether, 0.40 mL, 0.80 mmol) was added. After stirring for another day, the solution was concentrated in vacuo to give a residue. The residue was dissolved in SOCl$_2$ (4 mL). The solution was stirred at room temperature for 20 min before it was concentrated in vacuo to give a residue, which was then dissolved in DMF (3 mL). To the solution, NaN$_3$ (65 mg, 1.0 mmol) was added. After the mixture was stirred at room temperature for 2 h, water and EtOAc were added, then 5% aq. NaHCO$_3$ was added. The organic layer was separated, dried over Na$_2$SO$_4$, concentrated in vacuo to give methyl 2-(4-(azidomethyl)-1H-imidazol-1-yl)-5-(2-oxopyridin-1(2H)-yl)benzoate (25 mg). MS 351.1 (M+H).

To a solution of methyl 2-(4-(azidomethyl)-1H-imidazol-1-yl)-5-(2-oxopyridin-1(2H)-yl)benzoate prepared above (25 mg, 0.071 mmol) in THF (1 mL) and H$_2$O (0.025 mL, 1.4 mmol), Ph$_3$P (64 mg, 0.24 mmol) was added. After being stirred at room temperature overnight, the mixture was concentrated in vacuo to give methyl 2-(4-(aminomethyl)-1H-imidazol-1-yl)-5-(2-oxopyridin-1(2H)-yl)benzoate as a crude mixture, which was then used in the next transformation. MS 325.1 (M+H).

To a solution of 5-chlorothiophene-2-carboxylic acid 1-5 (40 mg, 0.25 mmol) and TEA (0.068 mL, 0.49 mmol) in DMF (2 mL), BOP (142 mg, 0.32 mmol) was added. After 5 min of mixing, the solution was added to the sample methyl 2-(4-(aminomethyl)-1H-imidazol-1-yl)-5-(2-oxopyridin-1(2H)-yl)benzoate prepared above. The mixture was then stirred at room temperature for 1 h before it was purified by HPLC to give the title compound (4 mg). MS 469.0 and 471.0 (M+H, Cl pattern).

Example 19

5-Chloro-N-((1-(4-(2-thioxopyridin-1(2H)-yl)phenyl)-1H-imidazol-4-yl)methyl)thiophene-2-carboxamide (30)

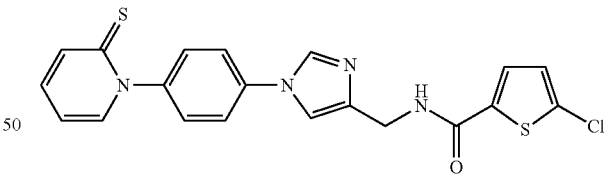

A mixture of 1,4-diiodobenzene 1-1 (2.00 g, 6.06 mmol), 2-hydroxypyridine 1-7 (0.576 g, 6.06 mmol), 8-hydroxyquinoline (0.088 g, 0.61 mmol) and K$_2$CO$_3$ (0.870 g, 6.30 mmol) in DMSO (8 mL) was degassed with Ar before being charged with CuI (0.115 g, 0.61 mmol). The mixture in a sealed tube was heated at 130° C. overnight. Water and EtOAc were added. The mixture was filtered through CELITE. The organic layer was separated, then applied to a silica gel column, which was eluted with 0-70% EtOAc in hexane to give 1-(4-iodophenyl)pyridin-2(1H)-one as a solid (0.760 g). MS 298.0 (M+H).

A mixture of 1-(4-iodophenyl)pyridin-2(1H)-one prepared above (0.760 g, 2.56 mmol), NaHCO$_3$ (2.15 g, 25.6 mmol) and P$_2$S$_5$ (2.27 g, 10.2 mmol) in dioxane (20 mL) was heated at 80° C. overnight. After being cooled to room temperature, water and CH$_2$Cl$_2$ were added. The organic layer was separated, washed with brine, dried over Na$_2$SO$_4$, concentrated in vacuo to give 1-(4-iodophenyl)pyridine-2(1H)-thione as a solid (0.752 g). MS 313.8 (M+H).

A mixture of 1-(4-iodophenyl)pyridine-2(1H)-thione prepared above (65 mg, 0.21 mmol), 5-chloro-N-((1H-imidazol-4-yl)methyl)thiophene-2-carboxamide 3-1 prepared in Example 11 (65 mg, 0.18 mmol), 8-hydroxyquinoline (10 mg, 0.069 mmol) and K$_2$CO$_3$ (75 mg, 0.54 mmol) in DMSO (2 mL) was degassed with Ar before being charged with CuI (27 mg, 0.14 mmol). The mixture in a sealed tube was heated at 130° C. overnight. It was then purified by HPLC to give the title compound (15 mg). MS 427.0 and 429.0 (M+H, Cl pattern).

Example 20

N-((1-(4-(2-oxopyridin-1(2H)-yl)phenyl)-1H-imidazol-4-yl)methyl)-1H-indole-6-carboxamide (31)

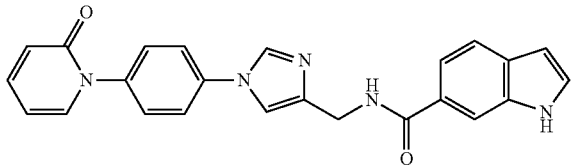 [SMILES: O=C(NCc1cn(-c2ccc(-n3ccccc3=O)cc2)cn1)c1ccc2cc[nH]c2c1]

To a solution of indole-6-carboxylic acid (85 mg, 0.528 mmol), 4-aminomethyl 1-(4-iodophenyl)imidazole 1-2 prepared in Example 1 (136 mg, 0.455 mmol) and TEA (0.150 mL, 1.08 mmol) in DMF (4 mL), BOP (280 mg, 0.633 mmol) was added. After the mixture was stirred at room temperature overnight, water and EtOAc were added. The organic layer was separated, washed with 5% aq. NaHCO$_3$, dried over Na$_2$SO$_4$, concentrated in vacuo to give N-((1-(4-iodophenyl)-1H-imidazol-4-yl)methyl)-1H-indole-6-carboxamide as a crude sample, which was used in the next reaction without further purification. MS 443.0 (M+H).

A mixture of N-((1-(4-iodophenyl)-1H-imidazol-4-yl)methyl)-1H-indole-6-carboxamide prepared above, 2-hydroxypyridine 1-7 (130 mg, 1.37 mmol), 8-hydroxyquinoline (30 mg, 0.21 mmol) and K$_2$CO$_3$ (246 mg, 1.78 mmol) in DMSO (2 mL) was degassed before being charged with CuI (43 mg, 0.23 mmol). The mixture in a sealed tube was heated at 130° C. overnight. It was then purified by HPLC to give the title compound (50 mg). MS 410.1 (M+H).

Example 21

5-Ethynyl-N-((1-(4-(2-oxopyridin-1(2H)-yl)phenyl)-1H-imidazol-4-yl)methyl)thiophene-2-carboxamide (32)

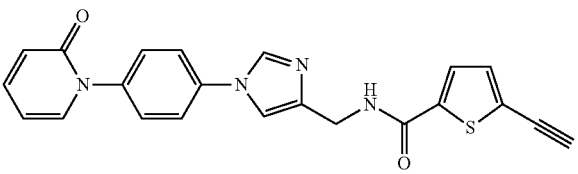 [SMILES: C#Cc1ccc(C(=O)NCc2cn(-c3ccc(-n4ccccc4=O)cc3)cn2)s1]

A mixture of ethyl 5-bromo-thiophene-2-carboxylate (500 mg, 2.13 mmol), trimethylsilylacetylene (0.445 mL, 3.2 mmol), Pd(PPh$_3$)$_4$ (15 mg) and CuI (10 mg) in diisopropylamine (10 mL) was heated at 80° C. for 2 h. After being cooled to room temperature, the mixture was filtered through CELITE, and the filtrate was poured into water. The product was extracted with EtOAc. The EtOAc solution was washed with brine, dried over MgSO$_4$, concentrated in vacuo to give ethyl 5-(2-trimethylsilyl-ethyn-1-yl)-thiophene-2-carboxylate (529 mg). MS 253 (M+H).

To a solution of ethyl 5-(2-trimethylsilyl-ethyn-1-yl)-thiophene-2-carboxylate prepared above (529 mg, 2.10 mmol) in THF (20 mL), 1N aq. LiOH (7.0 mL, 7.0 mmol) was added. After the mixture was stirred at 40° C. overnight, it was poured into water. The aqueous solution was acidified with 1N HCl to pH 1. The product was extracted with EtOAc. The EtOAc solution was washed with brine, dried over MgSO$_4$, concentrated in vacuo to give 5-ethynyl-thiophene-2-carboxylic acid (316 mg). MS 153 (M+H).

A mixture of 1-(4-iodophenyl)pyridin-2(1H)-one prepared in Example 19 (1.00 g, 3.37 mmol), 4-hydroxymethylimidazole II-1 (0.330 g, 3.37 mmol), 8-hydroxyquinoline (0.073 g, 0.50 mmol) and K$_2$CO$_3$ (1.00 g, 7.25 mmol) in DMSO (7 mL) was degassed with Ar before being charged with CuI (0.100 g, 0.52 mmol). The mixture in a sealed tube was heated at 130° C. overnight. Water and EtOAc were added. The mixture was filtered through CELITE. The organic layer was separated, dried over Na$_2$SO$_4$, concentrated in vacuo. The residue was purified by HPLC to give 1-(4-(4-(hydroxymethyl)-1H-imidazol-1-yl)phenyl)pyridin-2(1H)-one (335 mg). MS 268 (M+H).

To a suspension of 1-(4-(4-(hydroxymethyl)-1H-imidazol-1-yl)phenyl)pyridin-2(1H)-one prepared above (335 mg, 1.25 mmol) in CH$_3$CN (20 mL), SOCl$_2$ (5.0 mL) was added. After the mixture was stirred at room temperature for 2 h, it was concentrated in vacuo. The residue was then dissolved in DMF (20 mL). To the solution, NaN$_3$ (244 mg, 3.75 mmol) was added. After the mixture was stirred at room temperature overnight, water and EtOAc were added. The organic layer was separated, washed with 5% aq. NaHCO$_3$, dried over Na$_2$SO$_4$, concentrated in vacuo to give 1-(4-(4-(azidomethyl)-1H-imidazol-1-yl)phenyl)pyridin-2(1H)-one (203 mg). MS 293 (M+H).

To a solution of 1-(4-(4-(azidomethyl)-1H-imidazol-1-yl)phenyl)pyridin-2(1H)-one prepared above (203 mg, 0.695 mmol) in MeOH (6 mL) and EtOAc (6 mL), SnCl$_2$ 2H$_2$O (343 mg, 1.52 mmol) was added. After the mixture was heated to reflux for 1 h, it was concentrated in vacuo. The residue was purified by HPLC to give 1-(4-(4-(aminomethyl)-1H-imidazol-1-yl)phenyl)pyridin-2(1H)-one (145 mg). MS 267 (M+H).

To a solution of 5-ethynyl-thiophene-2-carboxylic acid (83 mg, 0.54 mmol) and TEA (0.15 mL, 1.1 mmol) in DMF (4 mL), HATU (228 mg, 0.60 mmol) was added. After being stirred at room temperature for 30 min, a solution of 1-(4-(4-(aminomethyl)-1H-imidazol-1-yl)phenyl)pyridin-2(1H)-one prepared above (145 mg, 0.54 mmol) and TEA (0.15 mL, 1.1 mmol) in DMF (8 mL) was added. The mixture was stirred at room temperature overnight. It was then purified by HPLC to give the title compound (65 mg). MS 401 (M+H).

Example 22

(E)-5-chloro-N-((1-(4-(2-(cyanoimino)pyridin-1(2H)-yl)phenyl)-1H-imidazol-4-yl)methyl)thiophene-2-carboxamide (33)

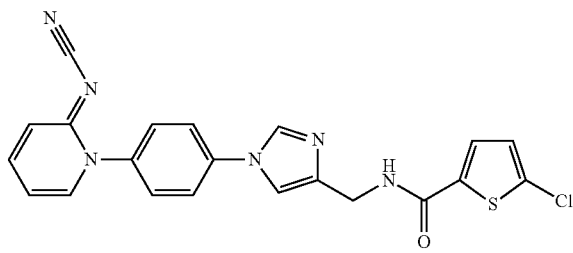 [SMILES: N#C/N=c1\ccccn1-c1ccc(-n2cnc(CNC(=O)c3ccc(Cl)s3)c2)cc1]

To a solution of 1-(4-iodophenyl)pyridine-2(1H)-thione (180 mg, 0.575 mmol) in CH₃CN (15 mL), CH₃I (0.50 mL, 8.0 mmol) was added. After being stirred at room temperature overnight, the mixture was concentrated in vacuo to give a solid. The solid was dissolved in CH₃CN (5 mL). To the solution, cyanamide (200 mg, 4.76 mmol) and hydrazine monohydrate (0.100 mL, 2.06 mmol) were added. After being stirred at room temperature for 2 h, the mixture was purified by HPLC to give (E)-(1-(4-iodophenyl)pyridin-2(1H)-ylidene)cyanamide (25 mg).

A mixture of (E)-(1-(4-iodophenyl)pyridin-2(1H)-ylidene)cyanamide (25 mg, 0.078 mmol), 5-Chloro-N-((1H-imidazol-4-yl)methyl)thiophene-2-carboxamide 3-1 (65 mg, 0.18 mmol), 8-hydroxyquinoline (10 mg, 0.069 mmol) and K₂CO₃ (75 mg, 0.54 mmol) in DMSO (1 mL) was degassed with Ar before being charged with CuI (15 mg, 0.079 mmol). The mixture in a sealed tube was heated at 130° C. overnight. It was then purified by HPLC to give the titled compound (10 mg). MS 435.1 and 437.0 (M+H, Cl pattern).

Example 23

(E)-5-chloro-N-((1-(4-(2-(methylimino)pyridin-1(2H)-yl)phenyl)-1H-imidazol-4-yl)methyl)thiophene-2-carboxamide (34)

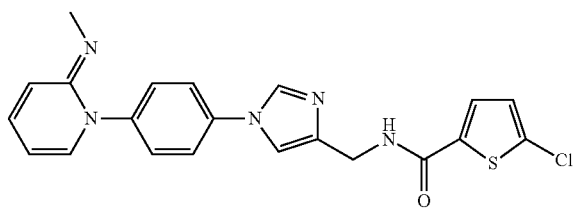 [SMILES: C/N=c1\ccccn1-c1ccc(-n2cnc(CNC(=O)c3ccc(Cl)s3)c2)cc1]

To a solution of 1-(4-iodophenyl)pyridine-2(1H)-thione (98 mg, 0.31 mmol) in CH₃CN (5 mL), CH₃I (0.25 mL, 4.0 mmol) was added. After being stirred at room temperature overnight, the mixture was concentrated in vacuo to give a solid. The solid was dissolved in MeOH (7 mL). To the solution, CH₃NH₂ (2M in THF, 0.80 mL, 1.6 mmol) was added. After being stirred at room temperature overnight, the mixture was purified by HPLC to give (E)-N-(1-(4-iodophenyl)pyridin-2(1H)-ylidene)methanamine (59 mg).

A mixture of (E)-N-(1-(4-iodophenyl)pyridin-2(1H)-ylidene)methanamine (59 mg, 0.14 mmol), 5-Chloro-N-((1H-imidazol-4-yl)methyl)thiophene-2-carboxamide 3-1 (63 mg, 0.18 mmol), 8-hydroxyquinoline (10 mg, 0.069 mmol) and K₂CO₃ (100 mg, 0.72 mmol) in DMSO (1 mL) was degassed with Ar before being charged with CuI (15 mg, 0.079 mmol). The mixture in a sealed tube was heated at 130° C. overnight. It was then purified by HPLC to give the titled compound (15 mg). MS 424.1 and 426.1 (M+H, Cl pattern).

Example 24

(E)-5-chloro-N-((1-(4-(2-(4-methoxyphenylimino)pyridin-1(2H)-yl)phenyl)-1H-imidazol-4-yl)methyl)thiophene-2-carboxamide (35)

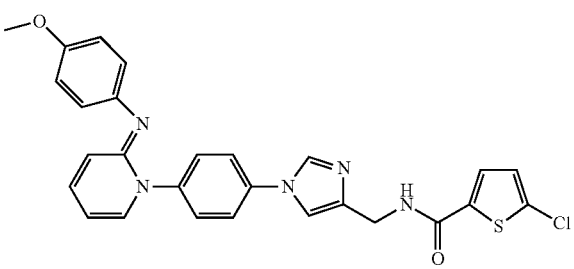 [SMILES: COc1ccc(/N=c2\ccccn2-c2ccc(-n3cnc(CNC(=O)c4ccc(Cl)s4)c3)cc2)cc1]

To a solution of 1-(4-iodophenyl)pyridine-2(1H)-thione (192 mg, 0.61 mmol) in CH₃CN (5 mL), CH₃I (0.40 mL, 6.4 mmol) was added. After being stirred at room temperature overnight, the mixture was concentrated in vacuo to give a solid. The solid was dissolved in DMF (3 mL). To the solution, p-anisidine (317 mg, 2.6 mmol) was added. After being stirred at 100° C. overnight, the mixture was purified by HPLC to give (E)-N-(1-(4-iodophenyl)pyridin-2(1H)-ylidene)-4-methoxybenzenamine (90 mg).

A mixture of (E)-N-(1-(4-iodophenyl)pyridin-2(1H)-ylidene)-4-methoxybenzenamine (90 mg, 0.17 mmol), 5-Chloro-N-((1H-imidazol-4-yl)methyl)thiophene-2-carboxamide 3-1 (62 mg, 0.17 mmol), 8-hydroxyquinoline (14 mg, 0.096 mmol) and K₂CO₃ (100 mg, 0.72 mmol) in DMSO (2 mL) was degassed with Ar before being charged with CuI (20 mg, 0.10 mmol). The mixture in a sealed tube was heated at 130° C. overnight. It was then purified by HPLC to give the titled compound (25 mg). MS 516.0 and 518.1 (M+H, Cl pattern).

Example 25

(E)-N-((1-(4-(2-(acetylimino)pyridin-1(2H)-yl)phenyl)-1H-imidazol-4-yl)methyl)-5-chlorothiophene-2-carboxamide (36)

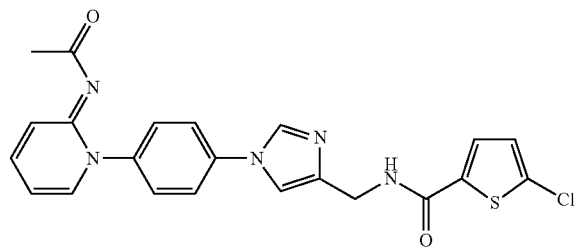 [SMILES: CC(=O)/N=c1\ccccn1-c1ccc(-n2cnc(CNC(=O)c3ccc(Cl)s3)c2)cc1]

To a solution of 1-(4-iodophenyl)pyridine-2(1H)-thione (384 mg, 1.23 mmol) in CH₃CN (10 mL), CH₃I (0.80 mL, 12.8 mmol) was added. After being stirred at room temperature overnight, the mixture was concentrated in vacuo to give a solid. The solid was dissolved in DMF (6 mL). To the solution, NH₃ in MeOH (7N, 3.0 mL, 21.0 mmol) and triethylamine (1.5 mL, 10.8 mmol) were added. After being stirred at room temperature overnight, the mixture was purified by HPLC to give a solid. The solid was dissolved in pyridine (3 mL) and CH₂Cl₂ (3 mL). To the solution, acetyl chloride (0.200 mL, 2.8 mmol) was added. After being stirred at room temperature overnight, the mixture was purified by HPLC to give (E)-N-(1-(4-iodophenyl)pyridin-2(1H)-ylidene)acetamide (120 mg).

A mixture of (E)-N-(1-(4-iodophenyl)pyridin-2(1H)-ylidene)acetamide (120 mg, 0.27 mmol), 5-Chloro-N-((1H-imidazol-4-yl)methyl)thiophene-2-carboxamide 3-1 (109 mg, 0.30 mmol), 8-hydroxyquinoline (15 mg, 0.10 mmol) and K₂CO₃ (100 mg, 0.72 mmol) in DMSO (2 mL) was degassed with Ar before being charged with CuI (24 mg, 0.12 mmol). The mixture in a sealed tube was heated at 130° C. for 5 h. It was then purified by HPLC to give the titled compound (8 mg). MS 452.0 and 454.0 (M+H, Cl pattern).

Example 26

4-chloro-1-methyl-N-((1-(4-(2-oxopyridin-1(2H)-yl)phenyl)-1H-imidazol-4-yl)methyl)-1H-pyrrole-2-carboxamide (37)

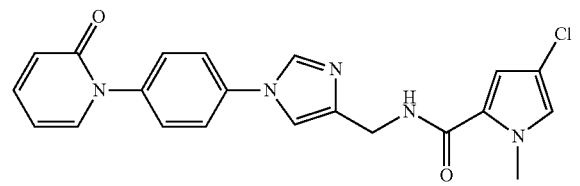 [SMILES: Cn1cc(Cl)cc1C(=O)NCc1cn(-c2ccc(-n3ccccc3=O)cc2)cn1]

A mixture of 1,4-diiodobenzene 1-1 (4.00 g, 12.1 mmol), 2-hydroxypyridine 1-7 (1.15 g, 12.1 mmol), 8-hydroxyquinoline (176 mg, 1.21 mmol) and K₂CO₃ (1.74 g, 12.6 mmol) in DMSO (16 mL) was degassed with Ar before being charged with CuI (230 mg, 1.21 mmol). The mixture in a sealed tube was heated at 130° C. overnight. After being cooled to room temperature, H₂O and EtOAc were added. It was filtered through celite. The organic phase was separated, dried over Na₂SO₄, concentrated in vacuo. The residue was purified by a silica gel column, eluted with EtOAc in hexanes (0-70% EtOAc) to give 1-(4-iodophenyl)pyridin-2(1H)-one (1.30 g).

To a solution of 1-methyl-2-pyrrolecarboxylic acid (1.03 g, 8.22 mmol) in MeOH (5 mL) and dioxane (5 mL) at room temperature, trimethylsilyldiazomethane (2M in ether, 5.0 mL, 10.0 mmol) was added. After being stirred at room temperature for 1 h, the mixture was concentrated in vacuo to give methyl 1-methyl-2-pyrrolecarboxylate as a volatile oil (1.14 g).

To a solution of methyl 1-methyl-2-pyrrolecarboxylate (1.14 g, 8.22 mmol) in ether (10 mL) at 0° C., SO₂Cl₂ (0.800 mL, 9.96 mmol) was added. After being stirred at room temperature for 15 min, the mixture was concentrated in vacuo. The residue was purified by a silica gel column, eluted with 5% EtOAc in hexane to give methyl 4-chloro-1-methyl-1H-pyrrole-2-carboxylate (0.13 g). The fractions containing methyl 5-chloro-1-methyl-1H-pyrrole-2-carboxylate were further purified by HPLC to give the 5-chloro-isomer.

To a solution of methyl 4-chloro-1-methyl-1H-pyrrole-2-carboxylate (130 mg, 0.75 mmol) in MeOH (4 mL), aq. 1N NaOH (3 mL) was added. After being stirred at room temperature overnight, the mixture was acidified with 1N HCl to pH 1-2. The product was extracted with EtOAc. The EtOAc phase was separated, dried over Na₂SO₄, concentrated in vacuo to give 4-chloro-1-methyl-1H-pyrrole-2-carboxylic acid as a solid (111 mg).

To a solution of 4-chloro-1-methyl-1H-pyrrole-2-carboxylic acid (55 mg, 0.34 mmol) and triethylamine (0.100 mL, 0.72 mmol) in DMF (2 mL), BOP (217 mg, 0.49 mmol) was added. After 5 min of stirring, a solution of 4-aminomethylimidazole II-2 (100 mg, 1.03 mmol) in DMF (2 mL) was added. After being stirred at room temperature overnight, the mixture was purified by HPLC to give N-((1H-imidazol-4-yl)methyl)-4-chloro-1-methyl-1H-pyrrole-2-carboxamide (81 mg).

A mixture of N-((1H-imidazol-4-yl)methyl)-4-chloro-1-methyl-1H-pyrrole-2-carboxamide (81 mg, 0.23 mmol), 1-(4-iodophenyl)pyridin-2(1H)-one (100 mg, 0.33 mmol), 8-hydroxyquinoline (15 mg, 0.10 mmol) and K₂CO₃ (193 mg, 1.40 mmol) in DMSO (2 mL) was degassed with Ar before being charged with CuI (21 mg, 0.11 mmol). The mixture in a sealed tube was heated at 130° C. overnight. It was then purified by HPLC to give the titled compound (25 mg). MS 408.1 and 410.1 (M+H, Cl pattern).

Example 27

5-chloro-1-methyl-N-((1-(4-(2-oxopyridin-1(2H)-yl)phenyl)-1H-imidazol-4-yl)methyl)-1H-pyrrole-2-carboxamide (38)

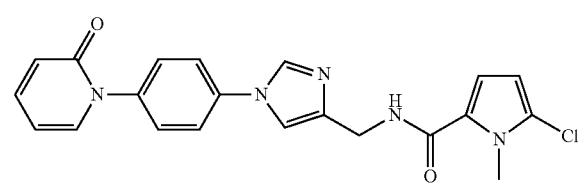

The titled compound was prepared analogously to preparation of 4-chloro-1-methyl-N-((1-(4-(2-oxopyridin-1(2H)-yl)phenyl)-1H-imidazol-4-yl)methyl)-1H-pyrrole-2-carboxamide of Example 26. MS 408.1 and 410.1 (M+H, Cl pattern).

Example 28

5-chloro-N-((1-(4-(1,1-dioxothiomorpholino)phenyl)-1H-imidazol-4-yl)methyl)thiophene-2-carbxamide (39)

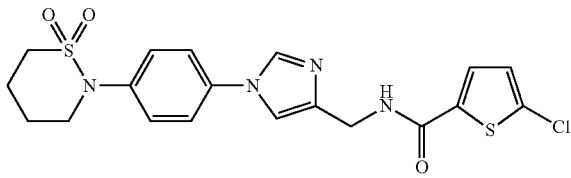 [SMILES: O=C(NCc1cn(-c2ccc(N3CCCCS3(=O)=O)cc2)cn1)c1ccc(Cl)s1]

A mixture of 5-chloro-N-((1-(4-iodophenyl)-1H-imidazol-4-yl)methyl)thiophene-2-carboxamide 1-6 (56 mg, 0.10 mmol), 1,4-butanesultam (52 mg, 0.38 mmol), 8-hydroxyquinoline (6 mg, 0.040 mmol) and K₂CO₃ (50 mg, 0.36 mmol) in DMSO (1 mL) was degassed before being charged with CuI (10 mg, 0.052 mmol). The mixture in a sealed tube was heated at 130° C. overnight. The mixture was then purified by HPLC to give the titled compound (10 mg). MS 451.1 and 453.1 (M+H, Cl pattern).

Example 29

5-chloro-N-((1-(3-fluoro-4-(2-oxopyridin-1(2H)-yl)phenyl)-1H-imidazol-4-yl)methyl)thiophene-2-carboxamide (40)

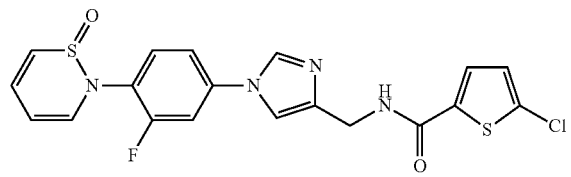 [SMILES: O=C(NCc1cn(-c2ccc(N3C=CC=CS3=O)c(F)c2)cn1)c1ccc(Cl)s1]

A mixture of 2,5-diiodofluorobenzene II-4 (2.50 g, 7.18 mmol), 4-hydroxymethylimidazole hydrochloride (0.967 g, 7.18 mmol), 8-hydroxyquinoline (0.104 g, 0.717 mmol) and K₂CO₃ (2.00 g, 14.5 mmol) in DMSO (12 mL) was degassed with Ar before being charged with CuI (0.136 g, 0.716 mmol). The mixture in a sealed tube was heated at 130° C. overnight. After being cooled to room temperature, H₂O and EtOAc were added. It was filtered through celite. The organic phase was separated, dried over Na₂SO₄, concentrated in vacuo. The residue was purified by a silica gel column, eluted with MeOH in CH₂Cl₂ (0-5% MeOH) to give (1-(3-fluoro-4-iodophenyl)-1H-imidazol-4-yl)methanol (0.39 g).

To a suspension of (1-(3-fluoro-4-iodophenyl)-1H-imidazol-4-yl)methanol (0.39 g, 1.23 mmol) in CH₃CN (7 mL), SOCl₂ (2.5 mL) was added. Upon the addition, the suspension became clear. It was then concentrated in vacuo. The residue was dissolved in DMF (7 mL), NaN₃ (0.32 g, 4.92 mmol) was added. The mixture was stirred at room temperature overnight. H₂O and EtOAc were added. The organic phase was separated, washed with 5% NaHCO₃, dried over Na₂SO₄, concentrated in vacuo. The residue was dissolved in MeOH (6 mL), Ra—Ni (50% slurry in H2O, ~200 mg) was added. The mixture was hydrogenated under balloon H₂ for 2 h. It was then filtered through celite. The filtrate was concentrated in vacuo to give (1-(3-fluoro-4-iodophenyl)-1H-imidazol-4-yl)methanamine as a solid (0.268 g).

To a solution of 5-chloro-2-thiophenecarboxylic acid 1-5 (165 mg, 1.01 mmol) and triethylamine (0.300 mL, 2.16 mmol) in DMF (5 mL), BOP (472 mg, 1.07 mmol) was added. After 5 min of stirring, a solution of (1-(3-fluoro-4-iodophenyl)-1H-imidazol-4-yl)methanamine (268 mg, 0.845 mmol) in DMF (4 mL) was added. The mixture was stirred at room temperature overnight. H₂O and EtOAc were added. The organic phase was separated, washed with 5% NaHCO₃, dried over Na₂SO₄, concentrated in vacuo. The residue was purified by HPLC to give 5-chloro-N-((1-(3-fluoro-4-iodophenyl)-1H-imidazol-4-yl)methyl)thiophene-2-carboxamide (83 mg).

A mixture of 5-chloro-N-((1-(3-fluoro-4-iodophenyl)-1H-imidazol-4-yl)methyl)thiophene-2-carboxamide (83 mg, 0.14 mmol), 2-hydroxypyridine 1-7 (30 mg, 0.31 mmol), 8-hydroxyquinoline (10 mg, 0.069 mmol) and K₂CO₃ (50 mg, 0.36 mmol) in DMSO (1 mL) was degassed with Ar before being charged with CuI (15 mg, 0.079 mmol). The mixture was heated at 130° C. in a sealed tube for 4 h. It was then purified by HPLC to give the titled compound (8 mg). MS 429.0 and 431.0 (M+H, Cl pattern).

Example 30

5-chloro-N-((1-(4-(3-methoxy-2-oxopyridin-1(2H)-yl)phenyl)-1H-imidazol-4-yl)methyl)thiophene-2-carboxamide (41)

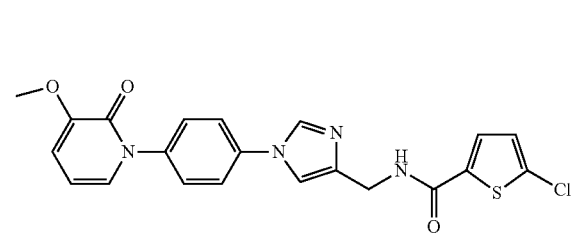 [SMILES: COc1cccn(-c2ccc(-n3cnc(CNC(=O)c4ccc(Cl)s4)c3)cc2)c1=O]

A mixture of 5-chloro-N-((1-(4-iodophenyl)-1H-imidazol-4-yl)methyl)thiophene-2-carboxamide 1-6 (150 mg, 0.34 mmol), 3-methoxy-2-hydroxypyridine (85 mg, 0.68 mmol), 8-hydroxyquinoline (20 mg, 0.14 mmol) and K₂CO₃ (100 mg, 0.72 mmol) in DMSO (2 mL) was degassed with Ar before being charged with CuI (25 mg, 0.13 mmol). The mixture in a sealed tube was heated at 130° C. for 4 h. The mixture was then purified by HPLC to give the titled compound (99 mg). MS 441.0 and 443.0 (M+H, Cl pattern)

Example 31

5-chloro-N-((1-(4-(3-hydroxy-2-oxopyridin-1(2H)-yl)phenyl)-1H-imidazol-4-yl)methyl)thiophene-2-carboxamide (42)

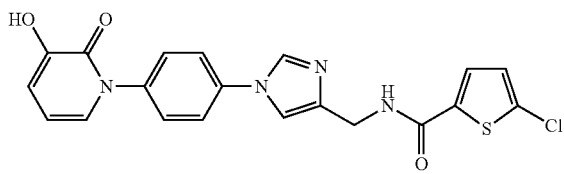 [SMILES: O=C(NCc1cn(-c2ccc(-n3cccc(O)c3=O)cc2)cn1)c1ccc(Cl)s1]

To a solution of 5-chloro-N-((1-(4-(3-methoxy-2-oxopyridin-1(2H)-yl)phenyl)-1H-imidazol-4-yl)methyl)thiophene-2-carboxamide (75 mg, 0.14 mmol) in CH$_2$Cl$_2$ (4 mL), BBr$_3$ (0.365 mL, 3.8 mmol) was added. The mixture was stirred at room temperature for 1 h. It was concentrated in vacuo. The residue was purified by HPLC to give the titled compound (40 mg). MS 427.0 and 429.0 (M+H, Cl pattern).

Example 32

5-chloro-N-((1-(4-(3-fluoro-2-oxopyridin-1(2H)-yl)phenyl)-1H-imidazol-4-yl)methyl)thiophene-2-carboxamide (43)

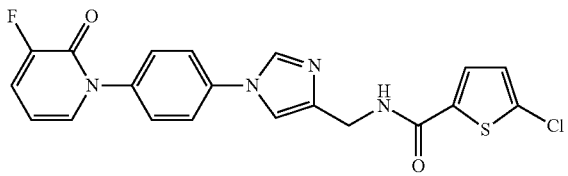 [SMILES: Cc1cccn(-c2ccc(-n3cnc(CNC(=O)c4ccc(Cl)s4)c3)cc2)c1=O]

A mixture of 5-chloro-N-((1-(4-iodophenyl)-1H-imidazol-4-yl)methyl)thiophene-2-carboxamide 1-6 (66 mg, 0.15 mmol), 3-fluoro-2-hydroxypyridine (46 mg, 0.40 mmol), 8-hydroxyquinoline (10 mg, 0.069 mmol) and K$_2$CO$_3$ (50 mg, 0.36 mmol) in DMSO (1 mL) was degassed with Ar before being charged with CuI (15 mg, 0.079 mmol). The mixture in a sealed tube was heated at 130° C. overnight. The mixture was then purified by HPLC to give the titled compound (8 mg). MS 429.0 and 431.0 (M+H, Cl pattern).

Example 33

5-chloro-N-((1-(4-(3-methyl-2-oxopyridin-1(2H)-yl)phenyl)-1H-imidazol-4-yl)methyl)thiophene-2-carboxamide (44)

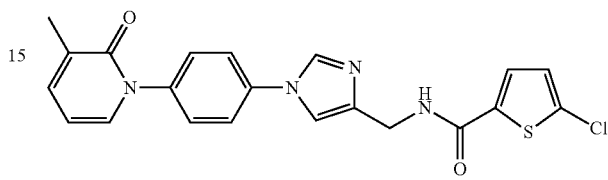

A mixture of 5-chloro-N-((1-(4-iodophenyl)-1H-imidazol-4-yl)methyl)thiophene-2-carboxamide 1-6 (66 mg, 0.15 mmol), 2-hydroxy-3-methylpyridine (45 mg, 0.41 mmol), 8-hydroxyquinoline (10 mg, 0.069 mmol) and K$_2$CO$_3$ (50 mg, 0.36 mmol) in DMSO (1 mL) was degassed with Ar before being charged with CuI (15 mg, 0.079 mmol). The mixture in a sealed tube was heated at 130° C. overnight. The mixture was then purified by HPLC to give the titled compound (10 mg). MS 425.0 and 427.0 (M+H, Cl pattern).

Example 34

5-chloro-N-((1-(4-(5-methyl-2-oxopyridin-1(2H)-yl)phenyl)-1H-imidazol-4-yl)methyl)thiophene-2-carboxamide (45)

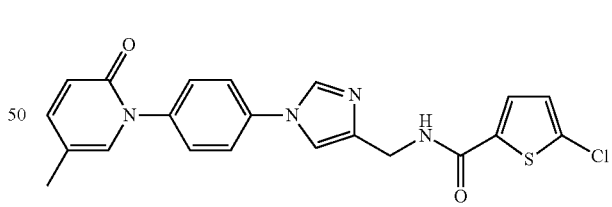

A mixture of 5-chloro-N-((1-(4-iodophenyl)-1H-imidazol-4-yl)methyl)thiophene-2-carboxamide 1-6 (56 mg, 0.13 mmol), 2-hydroxy-5-methylpyridine (45 mg, 0.41 mmol), 8-hydroxyquinoline (10 mg, 0.069 mmol) and K$_2$CO$_3$ (50 mg, 0.36 mmol) in DMSO (1 mL) was degassed with Ar before being charged with CuI (15 mg, 0.079 mmol). The mixture in a sealed tube was heated at 130° C. overnight. The mixture was then purified by HPLC to give the titled compound (8 mg). MS 425.0 and 427.0 (M+H, Cl pattern).

Example 35

5-chloro-N-((1-(4-(4-hydroxy-2-oxopyridin-1(2H)-yl)phenyl)-1H-imidazol-4-yl)methyl)thiophene-2-carboxamide (46)

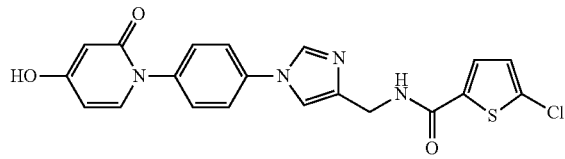 [SMILES: O=C(NCc1cn(-c2ccc(-n3ccc(O)cc3=O)cc2)cn1)c1ccc(Cl)s1]

A mixture of 5-chloro-N-((1-(4-iodophenyl)-1H-imidazol-4-yl)methyl)thiophene-2-carboxamide 1-6 (66 mg, 0.15 mmol), 2,4-dihydroxypyridine (45 mg, 0.41 mmol), 8-hydroxyquinoline (10 mg, 0.069 mmol) and $K_2CO_3$ (50 mg, 0.36 mmol) in DMSO (1 mL) was degassed with Ar before being charged with CuI (15 mg, 0.079 mmol). The mixture in a sealed tube was heated at 130° C. overnight. The mixture was then purified by HPLC to give the titled compound (6 mg). MS 427.0 and 429.0 (M+H, Cl pattern).

Example 36

5-chloro-N-((1-(4-(2,4-dioxo-3,4-dihydropyrimidin-1(2H)-yl)phenyl)-1H-imidazol-4-yl)methyl)thiophene-2-carboxamide (47)

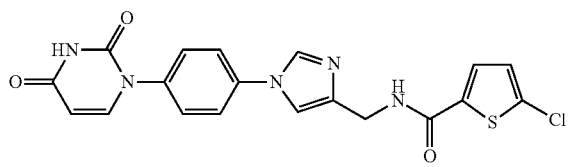 [SMILES: O=C(NCc1cn(-c2ccc(-n3ccc(=O)[nH]c3=O)cc2)cn1)c1ccc(Cl)s1]

A mixture of 5-chloro-N-((1-(4-iodophenyl)-1H-imidazol-4-yl)methyl)thiophene-2-carboxamide 1-6 (66 mg, 0.15 mmol), uracil (46 mg, 0.41 mmol), 8-hydroxyquinoline (10 mg, 0.069 mmol) and $K_2CO_3$ (50 mg, 0.36 mmol) in DMSO (1 mL) was degassed with Ar before being charged with CuI (15 mg, 0.079 mmol). The mixture in a sealed tube was heated at 130° C. overnight. The mixture was then purified by HPLC to give the titled compound (25 mg). MS 428.0 and 430.0 (M+H, Cl pattern).

Example 37

N-((1-(4-(4-amino-2-oxopyrimidin-1(2H)-yl)phenyl)-1H-imidazol-4-yl)methyl)-5-chlorothiophene-2-carboxamide (48)

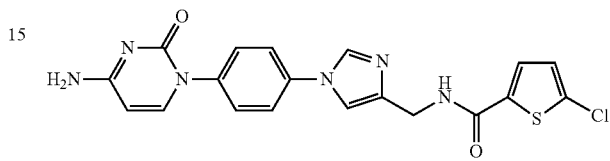

A mixture of 5-chloro-N-((1-(4-iodophenyl)-1H-imidazol-4-yl)methyl)thiophene-2-carboxamide 1-6 (66 mg, 0.15 mmol), cytosine (46 mg, 0.41 mmol), 8-hydroxyquinoline (10 mg, 0.069 mmol) and $K_2CO_3$ (50 mg, 0.36 mmol) in DMSO (1 mL) was degassed with Ar before being charged with CuI (15 mg, 0.079 mmol). The mixture in a sealed tube was heated at 130° C. overnight. The mixture was then purified by HPLC to give the titled compound (10 mg). MS 427.1 and 429.1 (M+H, Cl pattern).

Example 38

5-chloro-N-((1-(4-(3-methyl-2,4-dioxo-3,4-dihydropyrimidin-1(2H)-yl)phenyl)-1H-imidazol-4-yl)methyl)thiophene-2-carboxamide (49)

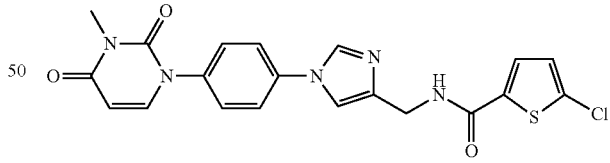

A mixture of 5-chloro-N-((1-(4-iodophenyl)-1H-imidazol-4-yl)methyl)thiophene-2-carboxamide 1-6 (66 mg, 0.15 mmol), 3-methyluracil (60 mg, 0.48 mmol), 8-hydroxyquinoline (10 mg, 0.069 mmol) and $K_2CO_3$ (60 mg, 0.43 mmol) in DMSO (1 mL) was degassed with Ar before being charged with CuI (15 mg, 0.079 mmol). The mixture in a sealed tube was heated at 130° C. overnight. The mixture was then purified by HPLC to give the titled compound (15 mg). MS 442.2 and 444.2 (M+H, Cl pattern).

Example 39

N-((1-(4-(4-amino-5-fluoro-2-oxopyrimidin-1(2H)-yl)phenyl)-1H-imidazol-4-yl)methyl)-5-chlorothiophene-2-carboxamide (50)

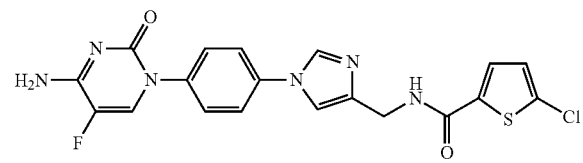 [SMILES: Nc1nc(=O)n(-c2ccc(-n3cnc(CNC(=O)c4ccc(Cl)s4)c3)cc2)cc1F]

A mixture of 5-chloro-N-((1-(4-iodophenyl)-1H-imidazol-4-yl)methyl)thiophene-2-carboxamide 1-6 (80 mg, 0.18 mmol), 5-fluorocytosine (60 mg, 0.46 mmol), 8-hydroxyquinoline (12 mg, 0.083 mmol) and K₂CO₃ (60 mg, 0.43 mmol) in DMSO (2 mL) was degassed with Ar before being charged with CuI (15 mg, 0.079 mmol). The mixture in a sealed tube was heated at 130° C. overnight. The mixture was then purified by HPLC to give the titled compound (15 mg). MS 445.2 and 447.2 (M+H, Cl pattern).

Example 40

N-((1-(4-(4-acetamido-2-oxopyrimidin-1(2H)-yl)phenyl)-1H-imidazol-4-yl)methyl)-5-chlorothiophene-2-carboxamide (51)

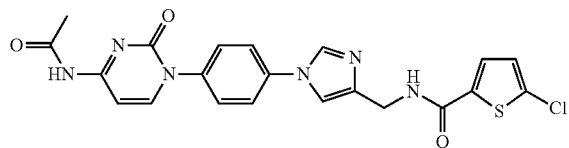 [SMILES: CC(=O)Nc1ccn(-c2ccc(-n3cnc(CNC(=O)c4ccc(Cl)s4)c3)cc2)c(=O)n1]

A mixture of 5-chloro-N-((1-(4-iodophenyl)-1H-imidazol-4-yl)methyl)thiophene-2-carboxamide 1-6 (80 mg, 0.18 mmol), N4-acetylcytosine (65 mg, 0.42 mmol), 8-hydroxyquinoline (12 mg, 0.083 mmol) and K₂CO₃ (60 mg, 0.43 mmol) in DMSO (2 mL) was degassed with Ar before being charged with CuI (15 mg, 0.079 mmol). The mixture in a sealed tube was heated at 130° C. overnight. The mixture was then purified by HPLC to give the titled compound (3 mg). MS 469.3 and 471.2 (M+H, Cl pattern).

Example 41

5-chloro-N-((1-(4-(2-oxopiperidin-1-yl)phenyl)-1H-imidazol-4-yl)methyl)thiophene-2-carboxamide (52)

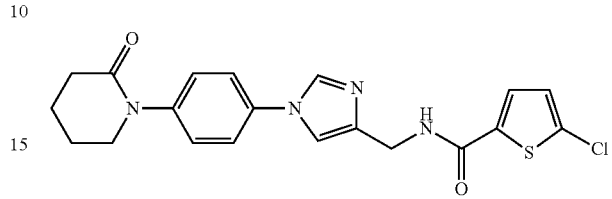

A mixture of 1-(4-(4-(aminomethyl)-1H-imidazol-1-yl)phenyl)pyridin-2(1H)-one hydrochloride (60 mg, 0.20 mmol) and Pd—C (10%, 31 mg) in MeOH (6 mL) was hydrogenated under balloon H₂ overnight. It was then filtered through celite. The filtrate was concentrated in vacuo to give 1-(4-(4-(aminomethyl)-1H-imidazol-1-yl)phenyl)piperidin-2-one (54 mg).

To a solution of 5-chloro-thiophene-2-carboxylic acid 1-5 (43 mg, 0.26 mmol) and triethylamine (0.200 mL, 1.43 mmol) in DMF (2 mL), BOP (130 mg, 0.29 mmol) was added. After 5 min of stirring, the solution was added to a solid sample of 1-(4-(4-(aminomethyl)-1H-imidazol-1-yl)phenyl)piperidin-2-one (54 mg, 0.18 mmol) in a flask. After being stirred at room temperature for 2 h, the mixture was purified by HPLC to give the titled compound (45 mg). MS 415.1 and 417.1 (M+H, Cl pattern).

Example 42

5-chloro-N-((1-(4-(2-oxopyridin-1(2H)-yl)-2-(2-(piperidin-1-yl)ethoxy)phenyl)-1H-imidazol-4-yl)methyl)thiophene-2-carboxamide (53)

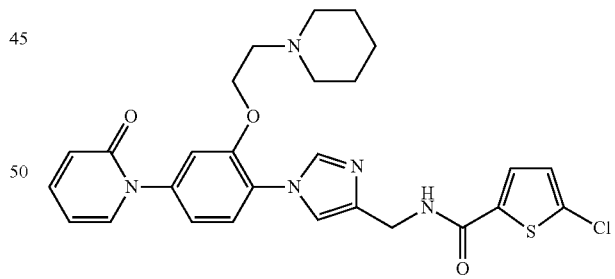

A mixture of 2-fluoro-4-iodoaniline (3.00 g, 12.6 mmol), 2-hydroxypyridine 1-7 (1.20 g, 12.6 mmol), 8-hydroxyquinoline (0.184 g, 1.26 mmol) and K₂CO₃ (3.49 g, 25.3 mmol) in DMSO (20 mL) was degassed with Ar before being charged with CuI (0.241 g, 1.27 mmol). The mixture in a sealed tube was heated at 130° C. overnight. After being cooled down to room temperature, H₂O and nBuOH were added. The organic phase was separated, concentrated in vacuo to give 1-(4-amino-3-fluorophenyl)pyridin-2(1H)-one as a solid (2.31 g).

To a solution of trifluoroacetic anhydride (10 mL, 71 mmol) in CH₂Cl₂ (25 mL) cooled at 0° C., H₂O₂ (50% aq., 4.4 mL, 72 mmol) was added dropwise. After stirring at 0° C. for 1 h, the sample of 1-(4-amino-3-fluorophenyl)pyridin-2(1H)-one (2.31 g, 11.3 mmol) was added in solid form portion by portion. After addition, the mixture was gradually removed from 0° C. to room temperature, and it was stirred at room temperature overnight. The solvent was removed in vacuo. To the residue, H₂O was added to induce precipitation, which was collected and dried on vacuum to give 1-(3-fluoro-4-nitrophenyl)pyridin-2(1H)-one (1.37 g).

To a suspension of 1-(3-fluoro-4-nitrophenyl)pyridin-2(1H)-one (0.70 g, 2.99 mmol) in anhydrous THF (6 mL) at room temperature, a pre-mixed solution of 1-piperidineethanol (0.40 mL, 3.02 mmol) and NaH (60%, 157 mg, 3.92 mmol) in anhydrous THF (8 mL) was added. After addition, the suspension became clear. The mixture was stirred at room temperature overnight. HPLC showed that the reaction was incomplete. Another pre-mixed solution of 1-piperidineethanol (0.40 mL, 3.02 mmol) and NaH (60%, 157 mg, 3.92 mmol) in anhydrous THF (5 mL) was added. After 1 h of stirring, the reaction was completed. H₂O and EtOAc were added. The organic phase was separated, washed with 5% NaHCO₃, dried over Na₂SO₄, concentrated in vacuo to give 1-(4-nitro-3-(2-(piperidin-1-yl)ethoxy)phenyl)pyridin-2(1H)-one (0.74 g).

A mixture of 1-(4-nitro-3-(2-(piperidin-1-yl)ethoxy)phenyl)pyridin-2(1H)-one (0.37 g, 1.08 mmol) and Pd—C (10%, 65 mg) in MeOH (15 mL) containing 6N HCl (0.5 mL) was hydrogenated on a Parr shaker under 45 psi of H₂ overnight. It was then filtered through celite. The filtrate was concentrated in vacuo to five 1-(4-amino-3-(2-(piperidin-1-yl)ethoxy)phenyl)pyridin-2(1H)-one (0.44 g).

To a solution of 1-(4-amino-3-(2-(piperidin-1-yl)ethoxy)phenyl)pyridin-2(1H)-one (0.44 g, 1.08 mmol) in conc. HCl (3 mL) at 0° C., a solution of NaNO₂ (75 mg, 1.08 mmol) in H₂O (2 mL) was added dropwise. After 30 min of stirring at 0° C., NaI (0.76 g, 5.07 mmol) in H₂O (2 mL) was added. After being stirred at 0° C. for 30 min, the mixture was removed to room temperature and was stirred at room temperature for 4 h. The solution was basified with 5 N NaOH to pH 10-12. The product was extracted with EtOAc, washed with 5% NaHCO₃, dried over Na₂SO₄, concentrated in vacuo. The residue was purified by HPLC to give 1-(4-iodo-3-(2-(piperidin-1-yl)ethoxy)phenyl)pyridin-2(1H)-one (116 mg).

A mixture of 1-(4-iodo-3-(2-(piperidin-1-yl)ethoxy)phenyl)pyridin-2(1H)-one (116 mg, 0.22 mmol), N-((1H-imidazol-4-yl)methyl)-5-chlorothiophene-2-carboxamide 3-1 (85 mg, 0.24 mmol), 8-hydroxyquinoline (14 mg, 0.10 mmol) and K₂CO₃ (200 mg, 1.45 mmol) in DMSO (3 mL) was degassed with Ar before being charged with CuI (19 mg, 0.10 mmol). The mixture in a sealed tube was heated at 130° C. overnight. It was then purified by HPLC to give the titled compound (10 mg). MS 538.2 and 540.2 (M+H, Cl pattern).

Example 43

N-((1-(4-(2-oxopyridin-1(2H)-yl)phenyl)-1H-imidazol-4-yl)methyl)-1H-indole-5-carboxamide (54)

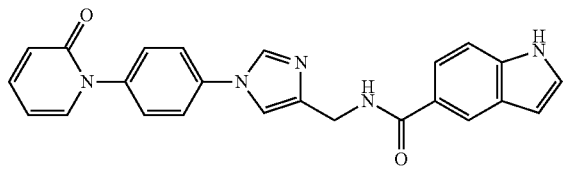 [SMILES: O=C(NCc1cn(-c2ccc(-n3ccccc3=O)cc2)cn1)c1ccc2[nH]ccc2c1]

To a solution of indole-5-carboxylic acid (40 mg, 0.25 mmol) and triethylamine (0.150 mL, 1.08 mmol) in DMF (2 mL), BOP (135 mg, 0.30 mmol) was added. After 5 min of stirring, 1-(4-(4-(aminomethyl)-1H-imidazol-1-yl)phenyl)pyridin-2(1H)-one hydrochloride (53 mg, 0.18 mmol) was added. The mixture was stirred at room temperature overnight. It was then purified by HPLC to give the titled compound (30 mg). MS 410.2 (M+H).

Example 44

5-chloro-N-((2-(methylthio)-1-(4-(2-oxopyridin-1(2H)-yl)phenyl)-1H-imidazol-4-yl)methyl)thiophene-2-carboxamide (55)

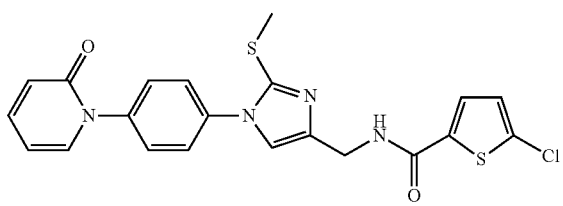 [SMILES: CSc1nc(CNC(=O)c2ccc(Cl)s2)cn1-c1ccc(-n2ccccc2=O)cc1]

To a suspension of ethyl 2-mercapto-1H-imidazole-4-carboxylate (4.00 g, 23.3 mmol) in acetone (30 mL) at room temperature, MeI (6 mL, 96.3 mmol) was added. During first 10 min of stirring, the suspension became clear, then it turned cloudy as product began to precipitate out. After being stirred at room temperature overnight, the precipitate was collected, dried on vacuum to give ethyl 2-(methylthio)-1H-imidazole-4-carboxylate (3.47 g).

A mixture of 1,4-diiodobenzene 1-1 (4.00 g, 12.1 mmol), ethyl 2-(methylthio)-1H-imidazole-4-carboxylate (2.26 g, 12.1 mmol), 8-hydroxyquinoline (270 mg, 1.86 mmol) and K₂CO₃ (3.40 g, 24.6 mmol) in DMSO (12 mL) was degassed with Ar before being charged with CuI (345 mg, 1.82 mmol). The mixture in a sealed tube was heated at 130° C. for 3 days. After cooling down, H₂O and EtOAc were added. After being filtered through celite, the organic phase was separated, dried over Na₂SO₄, concentrated in vacuo. The residue was purified by a silica gel column, eluted with EtOAc in hexane (10-35% EtOAc) to give ethyl 1-(4-iodophenyl)-2-(methylthio)-1H-imidazole-4-carboxylate (0.49 g).

To a solution of ethyl 1-(4-iodophenyl)-2-(methylthio)-1H-imidazole-4-carboxylate (0.49 g, 1.26 mmol) in anhydrous THF (10 mL) at room temperature, LiBH₄ (2M in THF, 3.2 mL, 6.4 mmol) was added. The mixture was stirred at room temperature overnight. H₂O and EtOAc were added. The organic phase was separated, washed with 5% NaHCO₃, dried over Na₂SO₄, concentrated in vacuo to give (1-(4-iodophenyl)-2-(methylthio)-1H-imidazol-4-yl)methanol (0.41 g).

To a solution of (1-(4-iodophenyl)-2-(methylthio)-1H-imidazol-4-yl)methanol (0.41 g, 1.18 mmol) in anhydrous dioxane (10 mL), diphenylphosphoryl azide (0.80 mL, 3.71 mmol) and DBU (0.600 mL, 4.02 mmol) were added. The mixture in a sealed tube was heated at 110° C. for 3 h. After being cooled down, H₂O and EtOAc were added. The organic phase was separated, washed with 5% NaHCO₃, dried over Na₂SO₄, concentrated in vacuo. The residue was purified by a silica gel column, eluted with EtOAc in hexane (0-20% EtOAc) to give 4-(azidomethyl)-1-(4-iodophenyl)-2-(methylthio)-1H-imidazole (0.39 g).

To a solution of 4-(azidomethyl)-1-(4-iodophenyl)-2-(methylthio)-1H-imidazole (0.26 g, 0.70 mmol) in EtOAc (10 mL), Tin(II) chloride dihydrate (0.63 g, 2.8 mmol) was added. The mixture was heated at reflux for 10 min. After being cooled down, 1N NaOH (10 mL) was added. The white precipitate was filtered off through celite. The EtOAc phase was separated, dried over $Na_2SO_4$, concentrated in vacuo to give (1-(4-iodophenyl)-2-(methylthio)-1H-imidazol-4-yl)methanamine (127 mg).

To a solution of 5-chloro-thiophene-2-carboxylic acid 1-5 (72 mg, 0.44 mmol) and triethylamine (0.150 mL, 1.10 mmol) in DMF (5 mL), BOP (235 mg, 0.53 mmol) was added. After 5 min of stirring, the solution was added to the sample of (1-(4-iodophenyl)-2-(methylthio)-1H-imidazol-4-yl) methanamine (127 mg, 0.37 mmol) in a flask. After being stirred at room temperature overnight, $H_2O$ and EtOAc were added. The organic phase was separated, washed with 5% $NaHCO_3$, dried over $Na_2SO_4$, concentrated in vacuo. The residue was dissolved in $CH_3CN$ (8 mL), $H_2O$ (10 mL) was added to induce precipitation, which was collected and dried on vacuum to give 5-chloro-N-((1-(4-iodophenyl)-2-(methylthio)-1H-imidazol-4-yl)methyl)thiophene-2-carboxamide (56 mg).

A mixture of 5-chloro-N-((1-(4-iodophenyl)-2-(methylthio)-1H-imidazol-4-yl)methyl)thiophene-2-carboxamide (56 mg, 0.11 mmol), 2-hydroxypyridine (30 mg, 0.32 mmol), 8-hydroxyquinoline (8 mg, 0.055 mmol) and $K_2CO_3$ (100 mg, 0.72 mmol) in DMSO (1 mL) was degassed with Ar before being charged with CuI (15 mg, 0.079 mmol). The mixture in a sealed tube was heated at 130° C. overnight. It was then purified by HPLC to give the titled compound (22 mg). MS 457.0 and 459.0 (M+H, Cl pattern).

Example 45

5-chloro-N-((2-(methylsulfonyl)-1-(4-(2-oxopyridin-1(2H)-yl)phenyl)-1H-imidazol-4-yl)methyl) thiophene-2-carboxamide (56) and 5-chloro-N((2-(methylsulfinyl)-1-(4-(2-oxopyridin-1(2H)-yl) phenyl)-1H-imidazol-4-yl)methyl)thiophene-2-carboxamide (57)

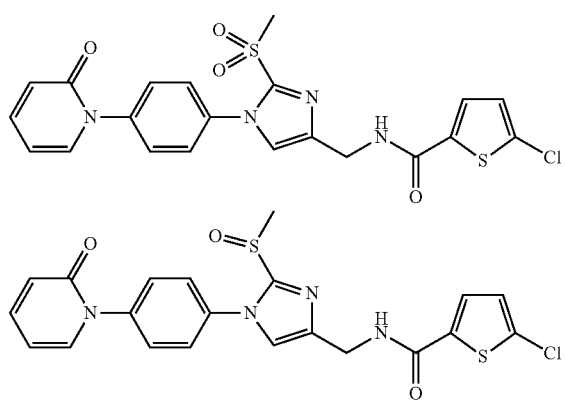

To a solution of 5-chloro-N-((2-(methylthio)-1-(4-(2-oxopyridin-1(2H)-yl)phenyl)-1H-imidazol-4-yl)methyl) thiophene-2-carboxamide (42 mg, 0.092 mmol) in DMF (3 mL), a solution of oxone (155 mg, 0.50 mmol) in $H_2O$ (2 mL) was added. The mixture was stirred at room temperature overnight. It was then purified by HPLC to give both the sulfone (6 mg) and sulfoxide (5 mg) products. MS 489.0 and 491.0 (M+H, Cl pattern, for sulfone); 473.0 and 475.0 (M+H, Cl pattern, for sulfoxide).

Example 46

5-chloro-N-((1-(4-(3-hydroxy-2-oxopyrazin-1(2H)-yl)phenyl)-1H-imidazol-4-yl)methyl)thiophene-2-carboxamide (58)

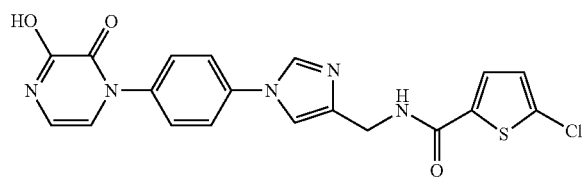 [SMILES: O=C(NCc1cn(-c2ccc(-n3ccnc(O)c3=O)cc2)cn1)c1ccc(Cl)s1]

A mixture of 5-chloro-N-((1-(4-iodophenyl)-1H-imidazol-4-yl)methyl)thiophene-2-carboxamide 1-6 (80 mg, 0.18 mmol), pyrazine-2,3-diol (50 mg, 0.44 mmol), 8-hydroxyquinoline (12 mg, 0.083 mmol) and $K_2CO_3$ (100 mg, 0.72 mmol) in DMSO (1 mL) was degassed with Ar before being charged with CuI (15 mg, 0.079 mmol). The mixture in a sealed tube was heated at 130° C. for 4 h. The mixture was then purified by HPLC to give the titled compound (5 mg). MS 428.0 and 430.0 (M+H, Cl pattern).

Example 47

5-chloro-N-((1-(4-(3-(2-hydroxyethoxy)-2-oxopyridin-1(2H)-yl)phenyl)-1H-imidazol-4-yl)methyl) thiophene-2-carboxamide (59)

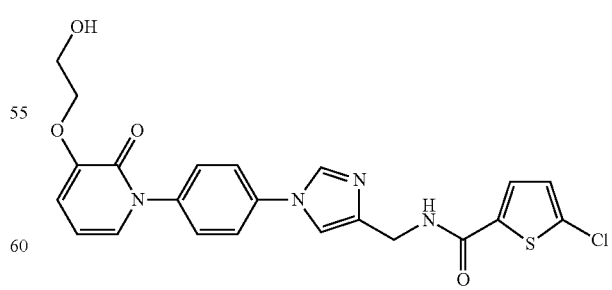

A mixture of 5-chloro-N-((1-(4-(3-hydroxy-2-oxopyridin-1(2H)-yl)phenyl)-1H-imidazol-4-yl)methyl)thiophene-2-carboxamide (30 mg, 0.070 mmol), 2-bromoethanol (0.020 mL, 0.28 mmol) and $Cs_2CO_3$ (90 mg, 0.28 mmol) in DMSO (1 mL) was stirred at 60° C. for 1 h. It was then purified by HPLC to give the titled compound (5 mg). MS 471.0 and 473.0 (M+H, Cl pattern).

Example 48

5-chloro-N-((1-(4-(4-ethyl-2,3-dioxopiperazin-1-yl)phenyl)-1H-imidazol-4-yl)methyl)thiophene-2-carboxamide (60)

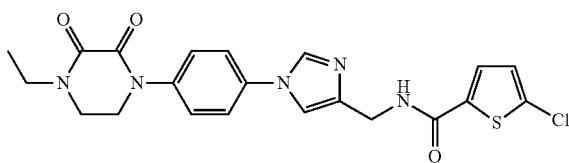 [SMILES: CCN1CCN(c2ccc(-n3cnc(CNC(=O)c4ccc(Cl)s4)c3)cc2)C(=O)C1=O]

A mixture of 5-chloro-N-((1-(4-iodophenyl)-1H-imidazol-4-yl)methyl)thiophene-2-carboxamide 1-6 (70 mg, 0.16 mmol), N-ethylpiperazine-2,3-dione (45 mg, 0.32 mmol), N,N'-dimethylethylenediamine (0.020 mL, 0.19 mmol) and K$_2$CO$_3$ (65 mg, 0.47 mmol) in DMSO (1 mL) and dioxane (1 mL) was degassed with Ar before being charged with CuI (20 mg, 0.10 mmol). The mixture in a sealed tube was heated at 110° C. overnight. The mixture was then purified by HPLC to give the titled compound (10 mg). MS 458.1 and 460.1 (M+H, Cl pattern).

Example 49

N-((1-(4-(2-(carbamoylimino)pyridin-1(2H)-yl)phenyl)-1H-imidazol-4-yl)methyl)-5-chlorothiophene-2-carboxamide (61)

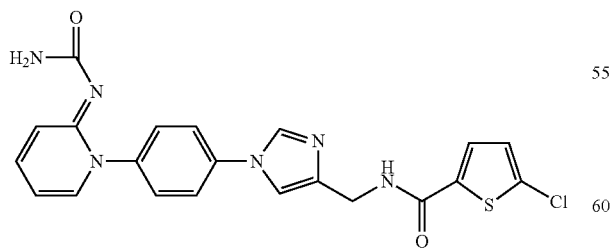

A solution of (E)-5-chloro-N-((1-(4-(2-cyanamidopyridin-1(2H)-yl)phenyl)-1H-imidazol-4-yl)methyl)thiophene-2-carboxamide (5 mg, 0.011 mmol) in TFA (0.30 mL) and H$_2$O (0.030 mL) was stirred at room temperature for 4 h. The solvents were removed in vacuo. The residue was purified by HPLC to give the titled compound (2 mg). MS 453.0 and 455.1 (M+H, Cl pattern).

Example 50

5-Chloro-N-((2-methyl-1-(4-(2-oxopyridin-1(2H)-yl)phenyl)-1H-imidazol-4-yl)methyl)thiophene-2-carboxamide (62)

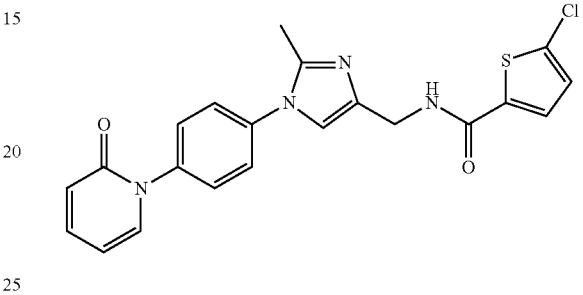

SCHEME 5

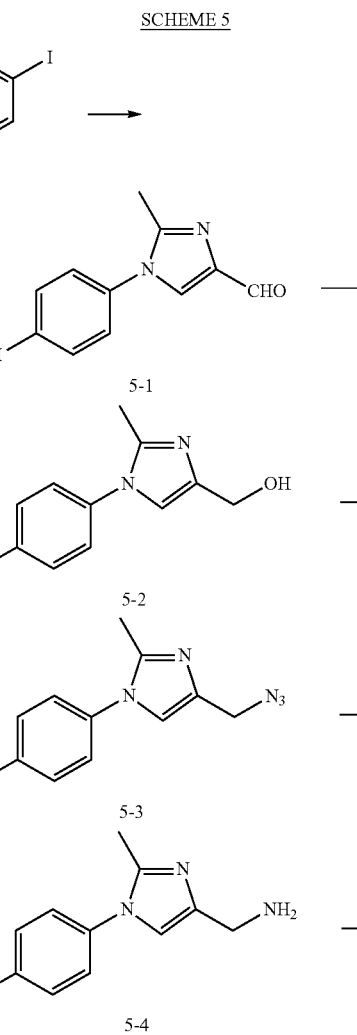

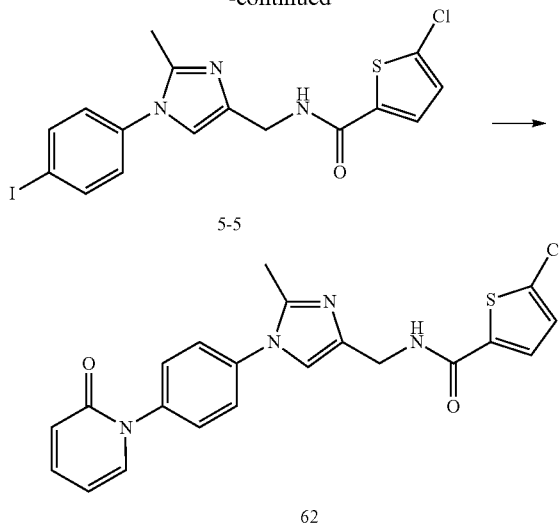

Step 1:

The mixture of 1,4-diiodobenzene 1-1 (600 mg, 1.8 mmol), 2-methyl-1H-imidazole-4-carbaldehyde (200 mg, 1.8 mmol), $K_2CO_3$ (503 mg, 3.6 mmol), CuI (105 mg, 0.55 mmol) and 8-hydroxyquinoline (80 mg, 0.55 mol) in 5 mL DMSO and 5 mL dioxane in a sealed tube was stirred for 2 days at 120° C. It was cooled to rt, and to it was added 60 mL water. The mixture was stirred for 30 min and filtered through a celite layer. The filtrate was concentrated in vacuo and subjected to reverse phase preparative HPLC to isolate 1-(4-iodophenyl)-2-methyl-1H-imidazole-4-carbaldehyde 5-1. MS found for $C_{11}H_9IN_2O(M+H)$+313.0.

Step 2:

The compound prepared in above step (140 mg, 0.45 mmol) was dissolved in 5 mL methanol and stirred at rt. To it was added $NaBH_4$ (26 mg, 0.67 mmol). The mixture was stirred for 30 min and subjected to preparative HPLC to isolate (1-(4-iodophenyl)-2-methyl-1H-imidazol-4-yl)methanol 5-2. MS found for $C_{11}K_{11}N_2O(M+H)$+315.0.

Step 3:

The compound prepared in above step (126 mg, 0.40 mmol) was dissolved in 4 mL dry acetonitrile. To it was added 2 mL thionyl chloride. The mixture was stirred for 40 min and concentrated in vacuo. The dry residue was then dissolved in 4 mL dry DMF. To it was added sodium azide (>5 eq). The mixture was stirred at rt for 1 hr and diluted with EtOAc. It was washed with brine four times, dried and concentrated in vacuo to give crude 4-(azidomethyl)-1-(4-iodophenyl)-2-methyl-1H-imidazole 5-3. MS found for $C_{11}H_{10}IN_5$ (M+H)+ 340.0.

Step 4:

The above prepared crude compound was dissolved in 2 mL ethanol and 2 mL acetic acid. Iron powder (10 eq) was added in. The mixture was stirred in 90° C. bath for 30 min. It was diluted with 20 mL water. The mixture was well stirred and filtered thru a celite layer. The filtrate was concentrated in vacuo and subjected to preparative HPLC to isolate (1-(4-iodophenyl)-2-methyl-1H-imidazol-4-yl)methanamine 5-4. MS found for $C_{11}H_{12}IN_3$ (M+H)+314.0.

Step 5:

The above prepared compound was dissolved in 50 mL methanol and treated with MP-carbonate (10 eq). The mixture was gently stirred for 1 hr and filtered. The filtrate was concentrated in vacuo to give the corresponding free amine (40 mg, 0.13 mmol). It was dissolved in 2 mL DMF. To it was added DIEA (16 µL, 0.15 mmol) and stirred at RT. In the meantime, 5-chlorothiophene-2-carboxylic acid 1-5 (24 mg, 0.15 mmol) was dissolved in 2 mL dry DMF. To it was added DIEA (16 µL, 0.15 mmol) and HATU (57 mg, 0.15 mmol). The mixture was stirred for 10 min. It was added to the stirred solution of the free amine in DMF. The mixture was stirred for 20 min and subjected to preparative HPLC to isolate 5-chloro-N-((1-(4-iodophenyl)-2-methyl-1H-imidazol-4-yl)methyl)thiophene-2-carboxamide 5-5. MS found for $C_{16}H_{13}ClIN_3OS(M+H)$+458.0, 460.0.

Step 6:

The above prepared compound (30 mg, 0.07 mmol) was dissolved in 2 mL DMSO in a sealed tube. To it were added 2-hydroxypyridine 1-7 (20 mg, 0.21 mmol), potassium carbonate (48 mg, 0.35 mmol), CuI (8 mg, 0.04 mmol) and 8-hydroxyquinoline (6 mg, 0.04 mmol). The mixture was stirred in 130° C. bath for overnight. The mixture was filtered and subjected to reverse phase preparative HPLC to isolate the title compound. MS found for $C_{21}H_{17}ClN_4O_2S$ (M+H)+ 425.1, 427.1.

Example 51

5-Chloro-N-((5-methyl-1-(4-(2-oxopyridin-1(2H)-yl) phenyl)-1H-imidazol-4-yl)methyl)thiophene-2-carboxamide (63)

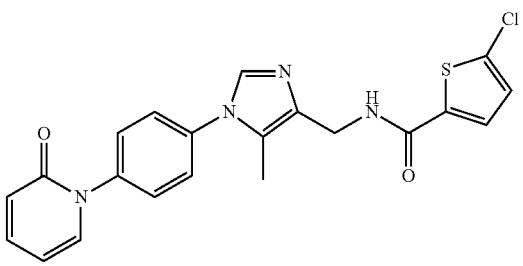 [SMILES: Cc1c(CNC(=O)c2ccc(Cl)s2)ncn1-c1ccc(-n2ccccc2=O)cc1]

SCHEME 6

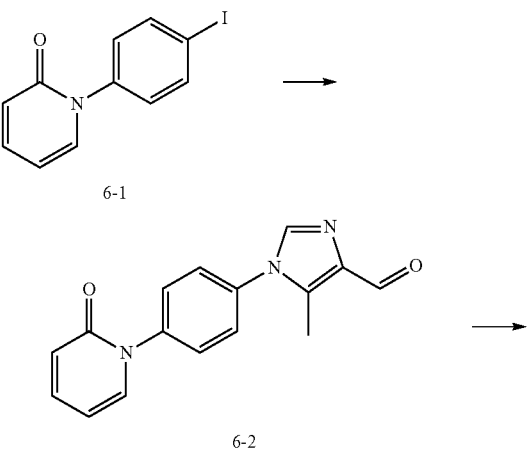

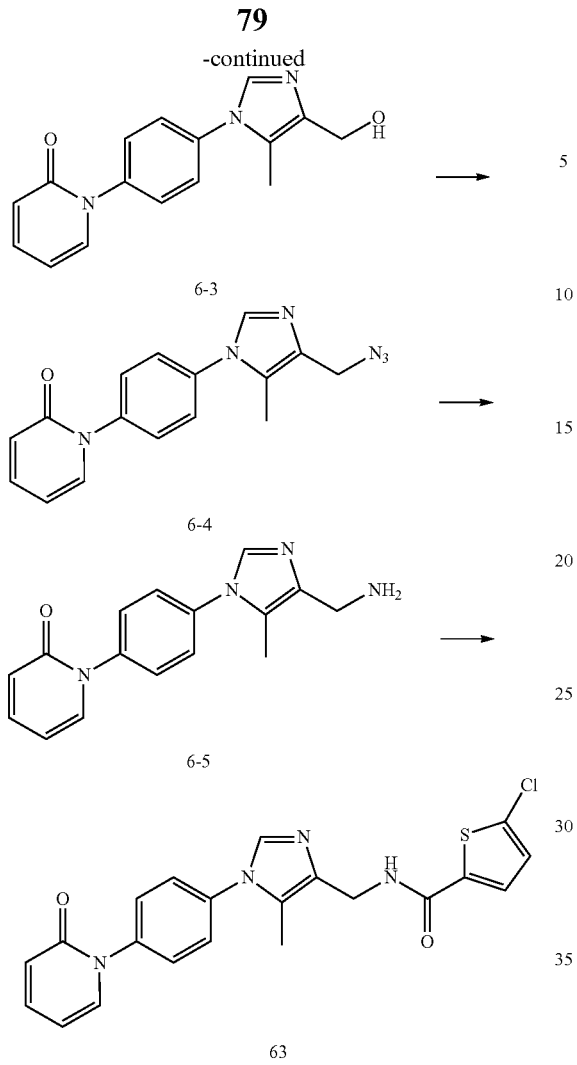

6-3

6-4

6-5

63

Step 1:
1-(4-Iodophenyl)pyridin-2(1H)-one 6-1 (200 mg, 0.67 mmol) was dissolved in 4 mL DMSO in a sealed tube. To it were added 5-methyl-1H-imidazole-4-carbaldehyde (300 mg, 2.7 mmol), K$_2$CO$_3$ (470 mg, 3.4 mmol), CuI (65 mg, 0.34 mmol) and 8-hydroxyquinoline (50 mg, 0.34 mol). The mixture was stirred at 130° C. for 16 hrs. The mixture was diluted with 100 mL acetonitrile, well stirred, and filtered through a celite layer. The filtrate was concentrated and subjected to prep HPLC to isolate 5-methyl-1-(4-(2-oxopyridin-1(2H)-yl)phenyl)-1H-imidazole-4-carbaldehyde 6-2. MS found for C$_{16}$H$_{13}$N$_3$O$_2$ (M+H)+280.1.

Step 2:
The above prepared compound (120 mg, 0.43 mmol) was stirred in 10 mL methanol at RT. NaBH$_4$ (25 mg, 0.64 mmol) was added. The mixture was stirred for 1 hr and subjected to prep HPLC to isolate 1-(4-(4-(hydroxymethyl)-5-methyl-1H-imidazol-1-yl)phenyl)pyridin-2(1H)-one 6-3. MS found for C$_{16}$H$_{15}$N$_3$O$_2$ (M+H)+283.1.

Step 3:
The above prepared compound (80 mg, 0.28 mmol) was stirred in 4 mL acetonitrile and 4 mL thionyl chloride. The mixture was stirred for 1 hr and concentrated in vacuo. The dry residue was then dissolved in 3 mL DMSO. To it was added sodium azide (10 eq). The mixture was stirred for 10 min and subjected to prep HPLC to isolate 1-(4-(4-(azidomethyl)-5-methyl-1H-imidazol-1-yl)phenyl)pyridin-2(1H)-one 6-4. MS found for C$_{16}$H$_{14}$N$_6$O(M+H)+307.1.

Step 4:
The above prepared compound (48 mg, 0.16 mmol) was dissolved in 1.5 mL ethanol and 3 mL acetic acid. To it was added iron powder (45 mg, 0.80 mmol). The mixture was stirred at 80° C. for 20 min and diluted with water. It was filtered and subjected to prep HPLC to isolate 1-(4-(4-(aminomethyl)-5-methyl-1H-imidazol-1-yl)phenyl)pyridin-2(1H)-one 6-5. MS found for C$_{16}$H$_{16}$N$_4$O(M+H)+281.1.

Step 5:
The above prepared compound was dissolved in 30 mL methanol and treated with MP-carbonate (10 eq). The mixture was gently stirred for 1 hr and filtered. The filtrate was concentrated in vacuo to give the corresponding free amine (45 mg, 0.16 mmol). It was dissolved in 3 mL DMF. To it was added DIEA (36 µL, 0.20 mmol) and stirred at RT. In the meantime, 5-chlorothiophene-2-carboxylic acid 1-5 (32 mg, 0.20 mmol) was dissolved in 3 mL dry DMF. To it was added DIEA (36 µL, 0.20 mmol) and HATU (76 mg, 0.20 mmol). The mixture was stirred for 10 min. It was added to the stirred solution of the free amine in DMF. The mixture was stirred for 1 hr and subjected to preparative HPLC to isolate the title compound. MS found for C$_{21}$H$_{17}$ClN$_4$O$_2$S(M+H)+425.1, 427.1.

Example 52

5-chloro-N-((1-(4-(5-fluoro-2-oxopyridin-1(2H)-yl)phenyl)-2-(methylsulfinyl)-1H-imidazol-4-yl)methyl)thiophene-2-carboxamide (64) and 5-chloro-N-((1-(4-(5-fluoro-2-oxopyridin-1(2H)-yl)phenyl)-2-(methylsulfonyl)-1H-imidazol-4-yl)methyl)thiophene-2-carboxamide (65)

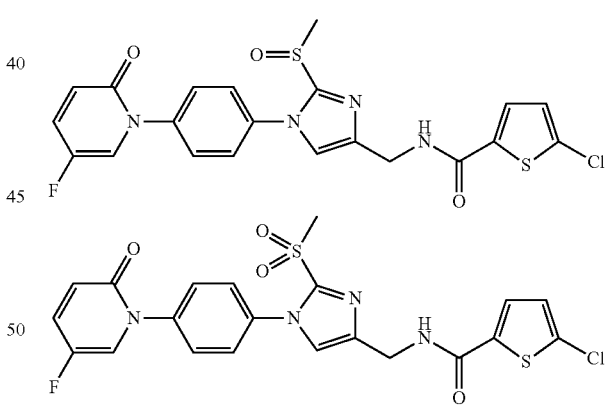

A mixture of 5-chloro-N-((1-(4-iodophenyl)-2-(methylthio)-1H-imidazol-4-yl)methyl)thiophene-2-carboxamide (50 mg, 0.10 mmol), 5-fluoro-2-hydroxypyridine (30 mg, 0.26 mmol), 8-hydroxyquinoline (10 mg, 0.069 mmol) and K$_2$CO$_3$ (70 mg, 0.50 mmol) in DMSO (2 mL) was degassed with Ar before being charged with CuI (14 mg, 0.073 mmol). The mixture in a sealed tube was heated at 130° C. overnight. After being cooled down to room temperature, H$_2$O (5 mL) was added to induce precipitation, which was collected and dried on vacuum to give a solid (38 mg).

To a solution of the solid (38 mg, 0.080 mmol) in DMF (3 mL), a solution of oxone (145 mg, 0.47 mmol) in H$_2$O (2 mL) was added. The mixture was stirred at room temperature overnight. It was then purified by HPLC to give both the sulfone (5 mg) and sulfoxide (4 mg) products. MS 507.0 and 509.0 (M+H, Cl pattern, for sulfone); 491.0 and 493.0 (M+H, Cl pattern, for sulfoxide).

Example 53

5-chloro-N-((1-(4-(3-fluoro-2-oxopyridin-1(2H)-yl)phenyl)-2-(methylsulfinyl)-1H-imidazol-4-yl)methyl)thiophene-2-carboxamide (66) and 5-chloro-N-((1-(4-(3-fluoro-2-oxopyridin-1(2H)-yl)phenyl)-2-(methylsulfonyl)-1H-imidazol-4-yl)methyl)thiophene-2-carboxamide (67)

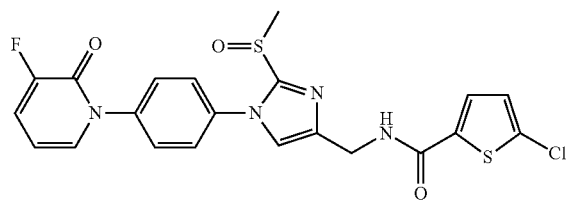

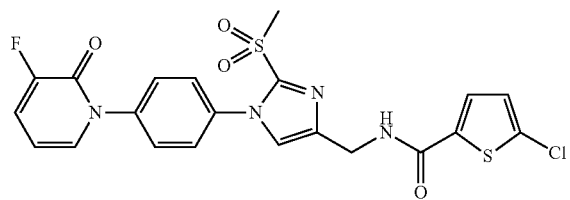

A mixture of 5-chloro-N-((1-(4-iodophenyl)-2-(methylthio)-1H-imidazol-4-yl)methyl)thiophene-2-carboxamide (50 mg, 0.10 mmol), 3-fluoro-2-hydroxypyridine (30 mg, 0.26 mmol), 8-hydroxyquinoline (10 mg, 0.069 mmol) and K$_2$CO$_3$ (70 mg, 0.50 mmol) in DMSO (2 mL) was degassed with Ar before being charged with CuI (28 mg, 0.15 mmol). The mixture in a sealed tube was heated at 130° C. overnight. After being cooled down to room temperature, H$_2$O (5 mL) was added to induce precipitation, which was collected and dried on vacuum to give a solid (34 mg).

To a solution of the solid (34 mg, 0.072 mmol) in DMF (4 mL), a solution of oxone (200 mg, 0.65 mmol) in H$_2$O (3 mL) was added. The mixture was stirred at room temperature overnight. It was then purified by HPLC to give both the sulfone (2 mg) and sulfoxide (4 mg) products. MS 507.0 and 509.0 (M+H, Cl pattern, for sulfone); 491.0 and 493.0 (M+H, Cl pattern, for sulfoxide).

Example 54

5-chloro-N-((1-(4-(5-fluoro-2-oxopyridin-1(2H)-yl)phenyl)-1H-imidazol-4-yl)methyl)thiophene-2-carboxamide (68)

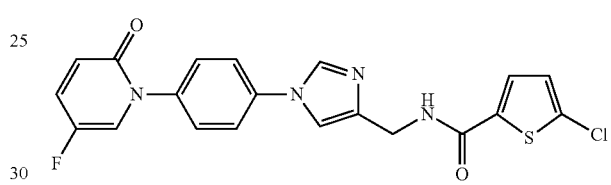

A mixture of 5-chloro-N-((1-(4-iodophenyl)-1H-imidazol-4-yl)methyl)thiophene-2-carboxamide 1-6 (66 mg, 0.15 mmol), 5-fluoro-2-hydroxypyridine (46 mg, 0.40 mmol), 8-hydroxyquinoline (10 mg, 0.069 mmol) and K$_2$CO$_3$ (50 mg, 0.36 mmol) in DMSO (1 mL) was degassed with Ar before being charged with CuI (15 mg, 0.079 mmol). The mixture in a sealed tube was heated at 130° C. overnight. The mixture was then purified by HPLC to give the titled compound (6 mg). MS 429.0 and 431.0 (M+H, Cl pattern).

The compounds in the following Table 1 may be prepared using methods similar to those above.

TABLE 1

| No. | Structure | Name |
|---|---|---|
| 69 | ![structure] | 5-chloro-N-((1-(2-(2-methoxyethoxy)-4-(2-oxopyridin-1(2H)-yl)phenyl)-1H-imidazol-4-yl)methyl)thiophene-2-carboxamide |

TABLE 1-continued

| No. | Structure | Name |
|---|---|---|
| 70 | 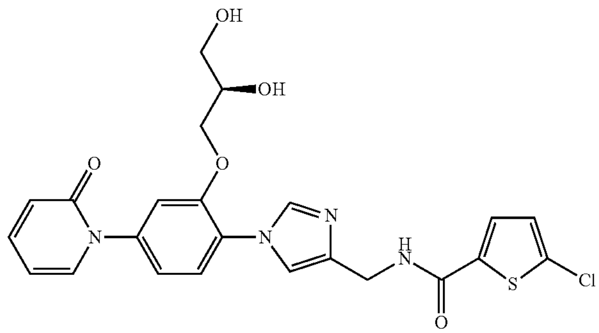 [SMILES: O=C(NCc1cn(-c2ccc(-n3ccccc3=O)cc2OC[C@H](O)CO)cn1)c1ccc(Cl)s1] | (R)-5-chloro-N-((1-(2-(2,3-dihydroxypropoxy)-4-(2-oxopyridin-1(2H)-yl)phenyl)-1H-imidazol-4-yl)methyl)thiophene-2-carboxamide |
| 71 | 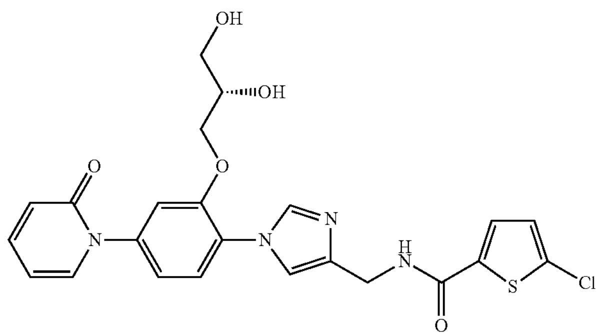 [SMILES: O=C(NCc1cn(-c2ccc(-n3ccccc3=O)cc2OC[C@@H](O)CO)cn1)c1ccc(Cl)s1] | (S)-5-chloro-N-((1-(2-(2,3-dihydroxypropoxy)-4-(2-oxopyridin-1(2H)-yl)phenyl)-1H-imidazol-4-yl)methyl)thiophene-2-carboxamide |
| 72 | 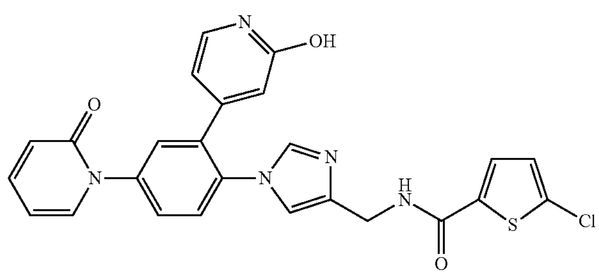 [SMILES: O=C(NCc1cn(-c2ccc(-n3ccccc3=O)cc2-c2ccnc(O)c2)cn1)c1ccc(Cl)s1] | 5-chloro-N-((1-(2-(2-hydroxypyridin-4-yl)-4-(2-oxopyridin-1(2H)-yl)phenyl)-1H-imidazol-4-yl)methyl)thiophene-2-carboxamide |
| 73 | 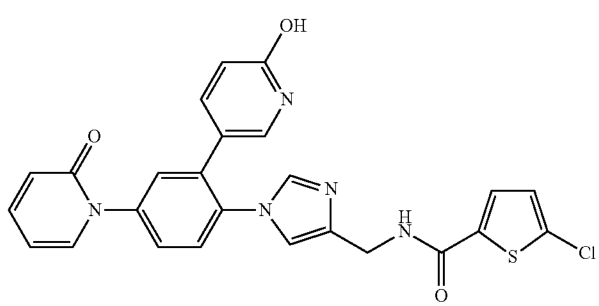 [SMILES: O=C(NCc1cn(-c2ccc(-n3ccccc3=O)cc2-c2ccc(O)nc2)cn1)c1ccc(Cl)s1] | 5-chloro-N-((1-(2-(6-hydroxypyridin-3-yl)-4-(2-oxopyridin-1(2H)-yl)phenyl)-1H-imidazol-4-yl)methyl)thiophene-2-carboxamide |
| 74 | 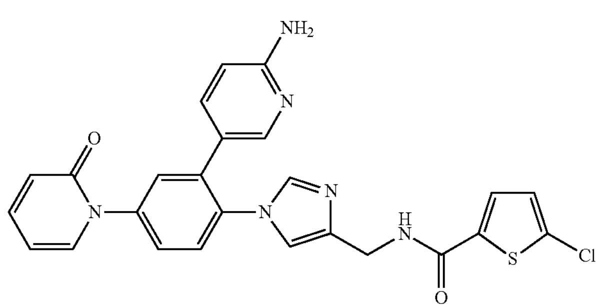 [SMILES: Nc1ccc(-c2cc(-n3ccccc3=O)ccc2-n2cnc(CNC(=O)c3ccc(Cl)s3)c2)cn1] | N-((1-(2-(6-aminopyridin-3-yl)-4-(2-oxopyridin-1(2H)-yl)phenyl)-1H-imidazol-4-yl)methyl)-5-chlorothiophene-2-carboxamide |

TABLE 1-continued

| No. | Structure | Name |
|---|---|---|
| 75 | 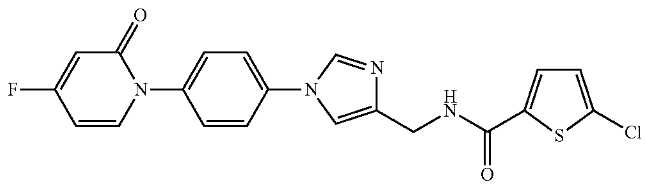 [SMILES: O=C(NCc1cn(-c2ccc(-n3ccc(F)cc3=O)cc2)cn1)c1ccc(Cl)s1] | 5-chloro-N-((1-(4-(4-fluoro-2-oxopyridin-1(2H)-yl)phenyl)-1H-imidazol-4-yl)methyl)thiophene-2-carboxamide |
| 76 | 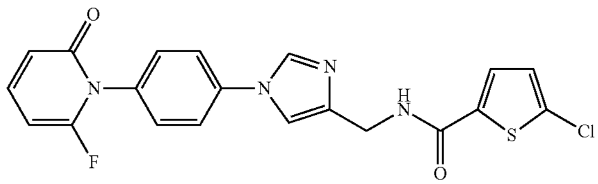 [SMILES: O=C(NCc1cn(-c2ccc(-n3c(F)cccc3=O)cc2)cn1)c1ccc(Cl)s1] | 5-chloro-N-((1-(4-(6-fluoro-2-oxopyridin-1(2H)-yl)phenyl)-1H-imidazol-4-yl)methyl)thiophene-2-carboxamide |
| 77 | 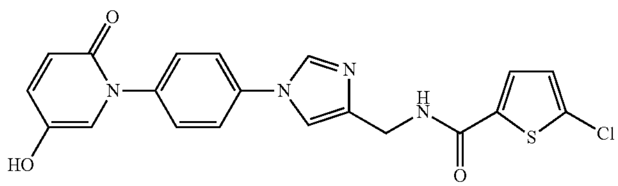 [SMILES: O=C(NCc1cn(-c2ccc(-n3cc(O)ccc3=O)cc2)cn1)c1ccc(Cl)s1] | 5-chloro-N-((1-(4-(5-hydroxy-2-oxopyridin-1(2H)-yl)phenyl)-1H-imidazol-4-yl)methyl)thiophene-2-carboxamide |
| 78 | 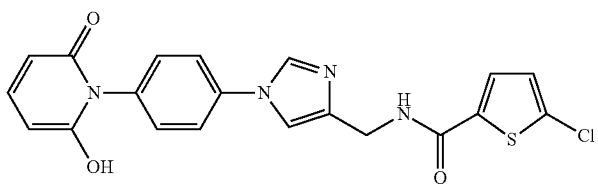 [SMILES: O=C(NCc1cn(-c2ccc(-n3c(O)cccc3=O)cc2)cn1)c1ccc(Cl)s1] | 5-chloro-N-((1-(4-(6-hydroxy-2-oxopyridin-1(2H)-yl)phenyl)-1H-imidazol-4-yl)methyl)thiophene-2-carboxamide |

Example 55

This example illustrates methods for evaluating the compounds of the invention, along with results obtained for such assays. The in vitro and in vivo human Factor Xa activities of the inventive compounds can be determined by various procedures known in the art, such as a test for their ability to inhibit the activity of human plasma Factor Xa. The potent affinities for human Factor Xa inhibition exhibited by the inventive compounds can be measured by an $IC_{50}$ value (in nM). The $IC_{50}$ value is the concentration (in nM) of the compound required to provide 50% inhibition of human Factor Xa proteolytic activity. The smaller the $IC_{50}$ value, the more active (potent) is a compound for inhibiting Factor Xa activity.

An in vitro assay for detecting and measuring inhibition activity against Factor Xa is as follows:
$IC_{50}$ and Ki Determinations:
Substrate:
  The substrate S-2765 (Z-D-Arg-Gly-Arg-pNA.HCl) was obtained from Diapharma (West Chester, Ohio).
Enzyme:
  The human plasma protein factor Xa was purchased from Haematologic Technologies (Essex Junction, Vt.).
Methods:
  $IC_{50}$ Determinations
  All assays, which are performed in 96-well microtiter plates, measure proteolytic activity of the enzyme (factor Xa) by following cleavage of a paranitroanilide peptide substrate. The assay buffer used for proteolytic assays was Tris buffered saline (20 mM Tris, 150 mM NaCl, 5 mM $CaCl_2$, 0.1% Bovine serum albumin (BSA), 5% Dimethly Sulfoxide (DMSO) pH 7.4). In a 96-well microtiter plate, inhibitor was serially diluted to give a range of final concentrations from 0.01 nM to 10 µM. Duplicate sets of wells were assayed and control wells without inhibitor were included. Enzyme was added to each well, (factor Xa concentration=1 nM), the plate was shaken for 5 seconds and then incubated for 5 minutes at room temperature. S2765 was added (100 µM final) and the plate was shaken for 5 seconds (final volume in each well was 200 µl). The degree of substrate hydrolysis was measured at 405 nm on a Thermomax plate reader (Molecular Devices, Sunnyvale, Calif.) for 2 minutes. The initial velocities of substrate cleavage (mOD/min), for each range of inhibitor concentrations, were fitted to a four parameter equation using Softmax data analysis software. The parameter C, derived from the resulting curve-fit, corresponded to the concentration for half maximal inhibition ($IC_{50}$).

$K_i$ Determination
  The assay buffer for this series of assays was Hepes buffered saline (20 mM Hepes, 150 mM NaCl, 5 mM $CaCl_2$, 0.1% PEG-8000, pH 7.4). In a 96-well microtiter plate, inhibitor was serially diluted in a duplicate set of wells to give a range of final concentrations from 5 µM to 3 µM. Controls without inhibitor (8 wells) were included. The enzyme, factor Xa (final concentration=1 nM) was added to the wells. The substrate S-2765 (final concentration=200 µM) was added and the degree of substrate hydrolysis was measured at 405 nm on a Thermomax plate reader for 5 minutes, using Softmax software. Initial velocities (mOD/min) were analyzed by non-linear least squares regression in the Plate $K_i$ software (BioKin Ltd, Pullman, Wash.) [Kusmic, et al., *Analytical*

*Biochemistry* 281: 62-67, 2000]. The model used for fitting the inhibitor dose-response curves was the Morrison equation. An apparent $K_i$ ($K_i^*$) was determined. The overall $K_i$ was calculated using the following equation:

$$Ki = \frac{Ki^*}{1 + \frac{[S]}{Km}}$$

where [S] is substrate concentration (200 μM) and $K_m$, the Michaelis constant for S2765.

The following examples exhibited Factor Xa $IC_{50}$ values less than or equal to 100 nM: 10-12, 14, 15, 18, 21-27, 30, 32, 33-36, 39-45, 47-53, 55-59, 61-62, and 64-67.

The following examples exhibited Factor Xa $IC_{50}$ values greater than 100 nM and less than 500 nM: 17, 19, 28, and 46.

The following examples exhibited Factor Xa $IC_{50}$ values greater than or equal to 500 nM: 13, 16, 20, 29, 31, 37-38, 54, 60, and 63.

Example 56

Compound 10 was used in the rat investigation. An intravenous (IV) and oral (PO) dose of Compound 10 (1.0 and 10 mg/kg, respectively) was prepared. The IV dose was solubilized in 50% PEG300 to yield a final concentration of 1.0 mg/mL with a final pH of 5.13. The PO dose was suspended in 0.5% methylcellulose at a concentration of 2.0 mg/mL with a final pH of 2.70.

For the dog and monkey study, Compound 10 was also used. An IV and PO dose of Compound 10 (1.0 and 5.0 mg/kg, respectively) was prepared. The IV dose was formulated similarly to that used in the rat study (50% PEG300 in water). The PO dose was suspended in 0.5% methylcellulose at a concentration of 1.0 mg/mL with a final pH of approximately 3.50.

Study Design

A total of six male Sprague-Dawley rats (n=3/dosing group) from Charles River Laboratories (Hollister, Calif.), three male beagle dogs from Marshall BioResources (North Rose, N.Y.) and three male rhesus monkeys were utilized. All surgical procedures in rat (femoral and jugular vein catheterizations) were performed 8 days prior to utilization in the study and rats were acclimated in-house 5 days prior to utilization. Dogs were acclimated in-house at least seven days prior to utilization and were returned to the colony at the completion of the study. Monkey studies were conducted by an off-site contract laboratory.

All animals were fasted from the afternoon prior to study initiation to two hours post-dose (approximately 18 hours). Water was provided ad libitum. All animal rooms were on a 12 hour light-dark cycles (6 A.M. to 6 P.M.). On the morning of experimentation, animals were weighed. Rat femoral and jugular (IV only) vein blood lines were exteriorized and attached to access ports. Dogs were weighed and shaved at blood sampling and IV dosing sites (along both cephalic and saphenous veins).

All animals were dosed based on individual weights with a PO gavage volume of 5.0 mL/kg and an IV bolus dose volume of 1.0 mL/kg. Blood samples were obtained on 3.8% TSC (1:10 dilution) over a 24, 56, and 96 hour period post-dosing for the rat, dog, and monkey, respectively. Blood samples were centrifuged for platelet poor plasma, and resulting plasma was stored at −20° C. until sample analysis. Rat urine samples were collected on 200 μL of 2% boric acid from animals in the IV group at 0 (overnight), 10, and 24 hours post-dose. At collection times, urine volume and water consumption was recorded. Urine samples were stored at −20° C. until sample analysis.

Sample Analysis

Plasma and urine samples were analyzed for Compound 10 concentration using a liquid chromatography tandem mass spectrometry (LC/MS/MS). In brief, plasma and urine samples were processed in a 96-well Captiva™ filter plate (0.2 μm, Varian, Inc., Palo Alto, Calif.). Aliquots of plasma samples were precipitated with acetonitrile containing 500 ng/mL of N-(2-(5-chloropyridin-2-ylcarbaomoyl)-4-methoxyphenyl)-4-(N,N-dimethylcarbamimidoyl)-2-fluorobenzamide, an internal standard. Aliquots of urine samples were diluted with plasma before mixing with acetonitrile containing internal standard. The mixture was vortexed and refrigerated at 4° C. for 30 minutes to allow complete protein precipitation. The mixture was filtered into a 96-well collection plate. The filtrate was injected onto a Sciex API3000 LC/MS/MS equipped with a turbo-ion spray source. Compound 10 and N-(2-(5-chloropyridin-2-ylcarbaomoyl)-4-methoxyphenyl)-4-(N,N-dimethylcarbamimidoyl)-2-fluorobenzamide were separated on a Thermo Hypersil-Keystone Betasil $C_{18}$ column (4.6×100 mm, 5um; Fisher Scientific, Houston, Tex.). A mobile phase gradient mixture of 90% mobile phase A (0.5% formic acid in water) and 10% mobile phase B (0.5% formic acid in 90% acetonitrile) to 40% mobile phase B (programmed over 2.8 minutes). The peak areas of the m/z 411→250 product ion (Compound 10) were measured against those of the m/z 470→342 product ion (N-(2-(5-chloropyridin-2-ylcarbaomoyl)-4-methoxyphenyl)-4-(N,N-dimethylcarbamimidoyl)-2-fluorobenzamide) in positive ion mode. The analytical range was 0.500 to 10,000 ng/mL.

Data Analysis

Sample Compound 10 concentrations below the lower limit of quantitation (LLQ) were reported as <0.500 ng/mL. These values were treated as zero for pharmacokinetic calculations.

Compound 10 pharmacokinetic parameter values were calculated by noncompartmental analysis of the plasma concentration-time data using Watson LIMS software (version 7.1). Terminal elimination rate constant (k) was calculated as the absolute value of the slope of linear regression of the natural logarithm (ln) of plasma concentration versus time during the terminal phase of the plasma concentration-time profile. Apparent terminal half-life (TO values were calculated as ln(2)/k. Area under the plasma concentration-time profile (AUC) values were estimated using the linear trapezoidal rule. $AUC_{all}$ values were calculated from time 0 to the time of the last detectable concentration. $AUC_{(0-inf)}$ values were calculated as the sum of the corresponding $AUC_{all}$ and the last detectable concentration divided by k. Systemic clearance (CL) was calculated from IV Dose/$AUC_{(0-inf)}$. Volume of distribution (Vz) was calculated from IV Dose/[k●$AUC_{0-inf}$]. Volume of distribution at steady-state (Vss) was calculated from CL*Mean Residence Time. Maximum plasma concentrations ($C_{max}$) and time to reach $C_{max}$ ($T_{max}$) were recorded as observed. Percentage oral bioavailability was calculated by taking the ratio of dose-normalized AUC $_{(0-inf)}$ values (AUC/D) following PO and IV administration. The results are shown in Tables 2-3 and the Figures below.

TABLE 2

Pharmacokinetic parameters of Compound 10 in rat, dog, and monkey after intravenous administration determined by noncompartmental analysis

| | | Mean ± SD | | |
|---|---|---|---|---|
| Parameter | Unit | Rat | Dog | Monkey |
| Dose | mg/kg | 1 | 1 | 1 |
| $T_{1/2}$ | hr | 2.86 ± 1.40 | | |
| $AUC_{all}$ | ng * hr/mL | 5376 ± 1186 | 1615 ± 360 | 12550 ± 5995 |
| $AUC_{(0-inf)}$ | ng * hr/mL | 5404 ± 1163 | 1622 ± 363 | 12560 ± 5998 |
| Vz | L/kg | 0.757 ± 0.328 | 2.73 ± 2.45 | 2.31 ± 1.71 |
| CL | mL/min/kg | 3.19 ± 0.734 | 10.7 ± 2.69 | 1.66 ± 1.06 |
| Vss | L/kg | 0.368 ± 0.026 | 0.843 ± 0.288 | 0.353 ± 0.059 |
| Dose excreted unchanged in urine | % | 0.248 ± 0.019 | | |

Noncompartmental analysis was performed using Watson LIMS software (version 7.1).
$T_{1/2}$: Terminal half-life
AUC: Area under the plasma concentration vs. time curve
Vz: Volume of distribution
CL: Systemic clearance
Vss: Volume of distribution at steady-state

TABLE 3

Pharmacokinetic parameters of Compound 10 in rat, dog, and monkey after oral administration determined by noncompartmental analysis

| | | Mean ± SD | | |
|---|---|---|---|---|
| Parameter | Unit | Rat | Dog | Monkey |
| Dose | mg/kg | 10 | 5 | 5 |
| $T_{1/2}$ | hr | 2.72 ± 0.29 | | |
| $T_{max}$ | hr | 0.250 ± 0.00 | 0.583 ± 0.382 | 2.00 ± 0.00 |
| $C_{max}$ | ng/mL | 28890 ± 2084 | 2717 ± 474 | 6041 ± 1877 |
| $AUC_{all}$ | ng * hr/mL | 68510 ± 12510 | 5464 ± 1471 | 42140 ± 17240 |
| $AUC_{(0-inf)}$ | ng * hr/mL | 68590 ± 12490 | 5475 ± 1475 | 42150 ± 17250 |
| AUC/D | kg * hr/mL | 6859 ± 1249 | 1095 ± 295 | 8430 ± 3449 |
| F | % | 127 ± 23.1 | 68.5 ± 15.5 | 71.6 ± 18.1 |

Noncompartmental analysis was performed using Watson LIMS software (version 7.1).
$T_{1/2}$: Terminal half-life
$T_{max}$: Time to reach maximal plasma concentration
$C_{max}$: Maximal plasma concentration
AUC: Area under the plasma concentration vs. time curve
% F: Absolute bioavailability The present invention provides a number of embodiments. It is apparent that the examples may be altered to provide other embodiments of this invention. Therefore, it will be appreciated that the scope of this invention is to be defined by the appended claims rather than by the specific embodiments, which have been represented by way of example.

What is claimed is:

1. A method for treating a condition in a mammal characterized by undesired thrombosis comprising administering to said mammal a therapeutically effective amount of a compound of the formula:

or a pharmaceutically acceptable salt thereof.

2. The method in accordance with claim 1, wherein the condition is selected from the group consisting of acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation, and conditions requiring the fitting of prosthetic devices.

3. A method for inhibiting the coagulation of a blood sample comprising contacting said sample with a compound of the formula:

or a pharmaceutically acceptable salt thereof.

4. The method in accordance with claim 1, wherein the pharmaceutically acceptable salt is a pharmaceutically acceptable acid addition salt.

5. The method in accordance with claim 4 wherein the acid addition salt is derived from an inorganic acid.

6. The method in accordance with claim 5, wherein the inorganic acid is selected from the group consisting of hydrochloric, hydrobromic, nitric, carbonic, monohydrogencarbonic, phosphoric, monohydrogenphosphoric, dihydrogenphosphoric, sulfuric, monohydrogensulfuric, hydriodic, and phosphorous acids.

7. The method in accordance with claim 5, wherein the inorganic acid is phosphoric acid.

8. The method in accordance with claim 4, wherein the acid addition salt is derived from an organic acid.

9. The method in accordance with claim 8, wherein the organic acid is selected from the group consisting of acetic, propionic, isobutyric, malonic, benzoic, succinic, suberic, fumaric, mandelic, phthalic, benzenesulfonic, p-tolylsulfonic, citric, tartaric, and methanesulfonic acids.

10. The method in accordance with claim 8, wherein the organic acid is methanesulfonic acid.

11. The method in accordance with claim 1, wherein the method is for treating deep venous thrombosis.

12. A method for treating a condition in a mammal characterized by undesired thrombosis comprising administering to said mammal a therapeutically effective amount of a mesylate salt of a compound of the formula:

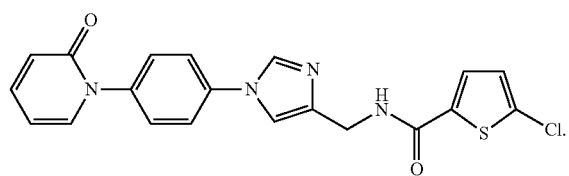 [SMILES: O=C(NCc1cn(-c2ccc(-n3ccccc3=O)cc2)cn1)c1ccc(Cl)s1]

13. The method in accordance with claim 12, wherein the condition is selected from the group consisting of acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation, and conditions requiring the fitting of prosthetic devices.

14. The method in accordance with claim 12, wherein the method is for treating deep venous thrombosis.

\* \* \* \* \*